(12) United States Patent
Yamashita et al.

(10) Patent No.: US 12,390,108 B2
(45) Date of Patent: Aug. 19, 2025

(54) BRAIN FUNCTIONAL CONNECTIVITY CORRELATION VALUE ADJUSTMENT METHOD, BRAIN FUNCTIONAL CONNECTIVITY CORRELATION VALUE ADJUSTMENT SYSTEM, BRAIN ACTIVITY CLASSIFIER HARMONIZATION METHOD, BRAIN ACTIVITY CLASSIFIER HARMONIZATION SYSTEM, AND BRAIN ACTIVITY BIOMARKER SYSTEM

(71) Applicant: ADVANCED TELECOMMUNICATIONS RESEARCH INSTITUTE INTERNATIONAL, Kyoto (JP)

(72) Inventors: Ayumu Yamashita, Soraku-gun (JP); Okito Yamashita, Soraku-gun (JP); Hiroshi Imamizu, Soraku-gun (JP); Mitsuo Kawato, Soraku-gun (JP)

(73) Assignee: ADVANCED TELECOMMUNICATIONS RESEARCH INSTITUTE INTERNATIONAL, Kyoto (JP)

( * ) Notice: Subject to any disclaimer, the term of this patent is extended or adjusted under 35 U.S.C. 154(b) by 965 days.

(21) Appl. No.: 17/284,051

(22) PCT Filed: Oct. 9, 2019

(86) PCT No.: PCT/JP2019/039751
§ 371 (c)(1),
(2) Date: Apr. 9, 2021

(87) PCT Pub. No.: WO2020/075737
PCT Pub. Date: Apr. 16, 2020

(65) Prior Publication Data
US 2021/0401289 A1 Dec. 30, 2021

(30) Foreign Application Priority Data

Oct. 11, 2018 (JP) .............................. 2018-192842
Feb. 27, 2019 (JP) .............................. 2019-034887

(51) Int. Cl.
*A61B 5/00* (2006.01)
*A61B 5/055* (2006.01)
*G06T 7/00* (2017.01)

(52) U.S. Cl.
CPC ............ *A61B 5/0042* (2013.01); *A61B 5/055* (2013.01); *A61B 5/7264* (2013.01);
(Continued)

(58) Field of Classification Search
CPC ..... A61B 5/0042; A61B 5/055; A61B 5/7264; A61B 2576/026; A61B 5/165;
(Continued)

(56) References Cited

U.S. PATENT DOCUMENTS

| | | |
|---|---|---|
| 2009/0118602 A1 | 5/2009 | Kawasaki et al. |
| 2015/0272461 A1 | 10/2015 | Morimoto et al. |
| 2020/0163609 A1 | 5/2020 | Lisi et al. |

FOREIGN PATENT DOCUMENTS

| | | |
|---|---|---|
| JP | 2011-184 A | 1/2011 |
| JP | 2015-62817 A | 4/2015 |

(Continued)

OTHER PUBLICATIONS

Yu, M., Linn, K. A., Cook, P. A., Phillips, M. L., McInnis, M., Fava, M., . . . & Sheline, Y. I. (2018). Statistical harmonization corrects site effects in functional connectivity measurements from multi-site fMRI data. Human brain mapping, 39(11), 4213-4227. (Year: 2018).*

(Continued)

*Primary Examiner* — Keith M Raymond
*Assistant Examiner* — Johnathan Maynard
(74) *Attorney, Agent, or Firm* — Birch, Stewart, Kolasch & Birch, LLP

(57) ABSTRACT

A harmonization system for a brain activity classifier harmonizing brain measurement data obtained at a plurality of sites to realize a discrimination process based on brain functional imaging: obtains data, for a plurality of traveling subjects as common objects of measurements at each of the plurality of measurement sites, resulting from measurements of brain activities of a predetermined plurality of brain regions of each of the traveling subjects; calculates, for each of the traveling subjects, prescribed elements of a brain functional connectivity matrix representing the temporal correlation of brain activities of a set of the plurality of brain regions; using a generalized linear mixed model, calculates measurement bias data 3108 for each element of the brain functional connectivity matrix, as a fixed effect at each measurement site with respect to an average of the corresponding element across the plurality of measurement sites and across the plurality of traveling subjects; and thereby executes a harmonizing process.

11 Claims, 43 Drawing Sheets

(52) U.S. Cl.
CPC ...... *G06T 7/0016* (2013.01); *A61B 2576/026* (2013.01); *G06T 2207/10088* (2013.01); *G06T 2207/30016* (2013.01)

(58) Field of Classification Search
CPC . A61B 5/7267; A61B 5/14542; A61B 5/7203; G06T 7/0016; G06T 2207/10088; G06T 2207/30016; G06T 2207/20081; G06T 7/0012; G16H 20/70; G16H 50/20; G16H 20/00; G16H 20/10; G16H 50/70; G16H 30/40; G16H 50/30; G06N 20/00; G06N 20/20; G06N 7/01; G06F 18/211; G06F 18/2415; G06F 2123/02; G06F 18/2136; G06F 18/23; G01R 33/4806; G01R 33/5608; G01R 33/58; G06V 2201/03

See application file for complete search history.

(56) References Cited

FOREIGN PATENT DOCUMENTS

| | | | |
|---|---|---|---|
| JP | 2017-196523 A | | 11/2017 |
| WO | WO 2006/132313 A1 | | 12/2006 |
| WO | WO 2017/090590 A1 | | 6/2017 |

OTHER PUBLICATIONS

Shimizu, Y., Yoshimoto, J., Toki, S., Takamura, M., Yoshimura, S., Okamoto, Y., . . . & Doya, K. (2015). Toward probabilistic diagnosis and understanding of depression based on functional MRI data analysis with logistic group LASSO. PloS one, 10(5), e0123524. (Year: 2015).*

Fortin, J. P., Parker, D., Tunç, B., Watanabe, T., Elliott, M. A., Ruparel, K., . . . & Shinohara, R. T. (2017). Harmonization of multi-site diffusion tensor imaging data. Neuroimage, 161, 149-170. (Year: 2017).*

Johnson, W. E., Li, C., & Rabinovic, A. (2007). Adjusting batch effects in microarray expression data using empirical Bayes methods. Biostatistics, 8(1), 118-127. (Year: 2007).*

Scikit-learn user guide. Release 0.19.2. (2018). https://scikit-learn.org/0.19//_downloads/scikit-learn-docs.pdf. Chapters 3.1 and 4.15, 151-281, 931-1001. (Year: 2018).*

Fortin, J. P., Cullen, N., Sheline, Y. I., Taylor, W. D., Aselcioglu, I., Cook, P. A., . . . & Shinohara, R. T. (2018). Harmonization of cortical thickness measurements across scanners and sites. Neuroimage, 167, 104-120. (Year: 2018).*

Yamashita, A., Yahata, N., Itahashi, T., Lisi, G., Yamada, T., Ichikawa, N., . . . & Imamizu, H. (2018). Harmonization of resting-state functional MRI data across multiple imaging sites via the separation of site differences into sampling bias and measurement bias. bioRxiv preprint. DOI:10.1101/440875. (Year: 2018).*

Glasser et al., "The Human Connectome Project's Neuroimaging Approach", Nat Neurosci., Aug. 26, 2016, vol. 19, No. 9, pp. 1175-1187, total 31 pages.

Kamitani et al., "Decoding the visual and subjective contents of the human brain", Nat Neurosci, May 2005, vol. 8, No. 5, pp. 679-685.

Noble et al., "Multisite reliability of MR-based functional connectivity", NeuroImage, 2017, vol. 146, pp. 959-970.

Pearlson, "Multisite Collaborations and Large Databases in Psychiatric Neuroimaging: Advantages, Problems, and Challenges", Schizophrenia Bulletin, 2009, vol. 35, No. 1, pp. 1-2.

Abraham et al., "Deriving reproducible biomarkers from multi-site resting-state data: An Autism-based example," NeuroImage, vol. 147, 2017 (Available online Nov. 16, 2016), pp. 736-745.

Extended European Search Report for corresponding European Application No. 19870503.0, dated Jun. 27, 2022.

Hawco et al., "A longitudinal phantom reliability study of multicenter T1-weighted, DTI, and resting state of fMRI data," Psychiatry Research: Neuroimaging, vol. 282, 2018 (Available online Jun. 9, 2018), pp. 134-142.

Thomas et al., "An application of item response theory to fMRI data: Prospects and pitfalls," Psychiatry Research: Neuroimaging, vol. 212, May 1, 2013, pp. 167-174.

* cited by examiner

| SITE/5 | | |
|---|---|---|
| SITE NAME | | |
| CONDITION/5 | | |
| MEASUREMENT DEVICE | MANUFACTURER'S NAME | |
| | MODEL No. | |
| | NUMBER OF RECEIVING COILS | |
| | ... | |
| MEASUREMENT CONDITIONS | DIRECTION OF PHASE ENCODING (P→A, A→P) | |
| | IMAGE TYPE | |
| | IMAGING SEQUENCE | |
| | EYES OPEN/CLOSED | |
| | ... | |

(B)

| SUBJECT ANONYMIZED/5 | | | |
|---|---|---|---|
| CONDITION/5 | | | |
| SEX | | | |
| AGE | | | |
| HEALTHY/DISEASE | | | |
| DIAGNOZED DISEASE NAME | | | |
| MEDICATION PROFILE | (RELATIVE DATE) | MEDICATION 1 | MEDICATION 2 |
| | (RELATIVE DATE) | ... | ... |
| DIAGNOSIS HISTORY | (RELATIVE DATE) | DIAGNOSIS | DIAGNOSIS |
| | (RELATIVE DATE) | ... | ... |

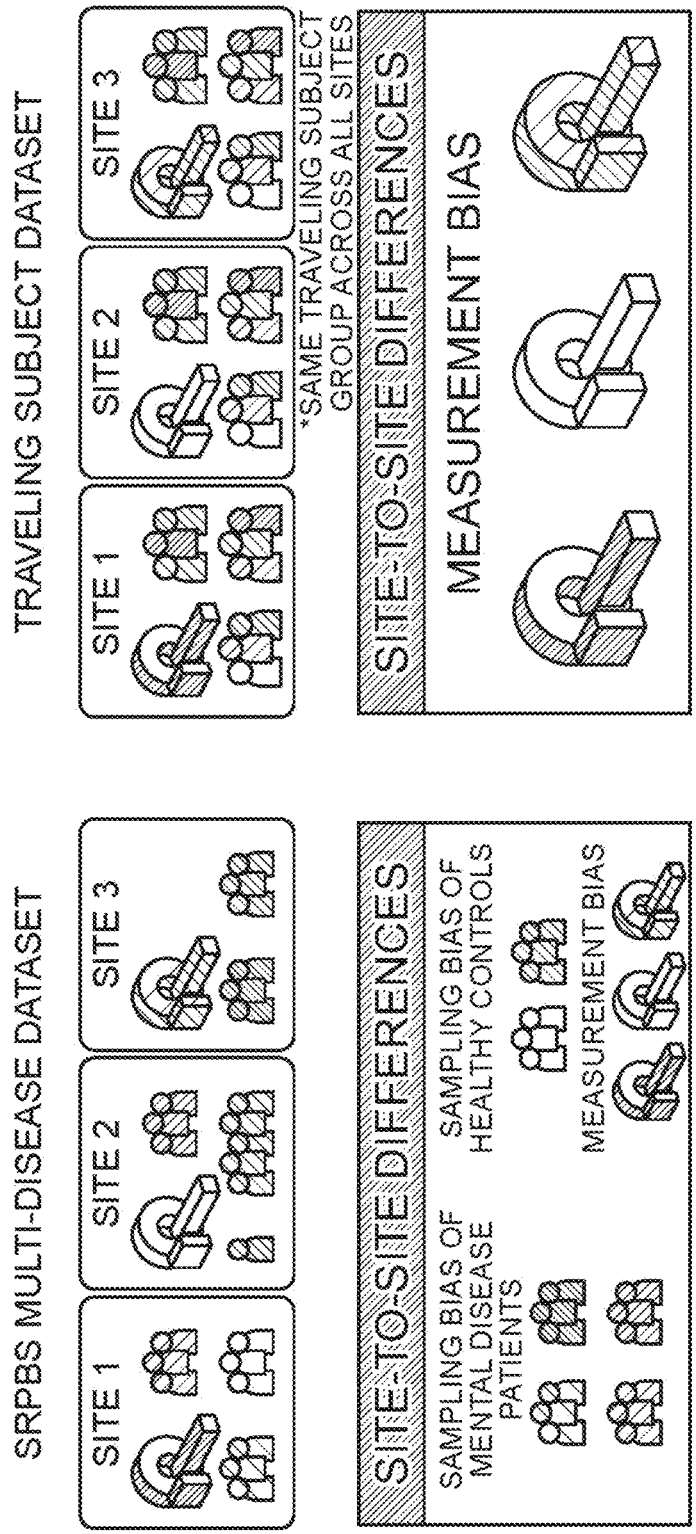

Fig. 15

DEMOGRAPHIC CHARACTERISTICS OF PATIENTS IN SRPBS MULTI-DISEASE DATASET

| SITE | HC | | | MDD | | | ASD | | | OCD | | | SCZ | | | ALL | | |
|---|---|---|---|---|---|---|---|---|---|---|---|---|---|---|---|---|---|---|
| | NUMBER OF PARTICIPANTS | MALE FEMALE | AGE (yr) | NUMBER OF PARTICIPANTS ADJUSTMENT | MALE FEMALE | AGE (yr) | NUMBER OF PARTICIPANTS | MALE FEMALE | AGE (yr) | NUMBER OF PARTICIPANTS | MALE FEMALE | AGE (yr) | NUMBER OF PARTICIPANTS | MALE FEMALE | AGE (yr) | NUMBER OF PARTICIPANTS | MALE FEMALE | AGE (yr) *1 |
| ATR Tim Trio (ATT) | 31 | 28/3 | 23.0±1.9 | 0 | - | - | 0 | - | - | 0 | - | - | 0 | - | - | 31 | 28/3 | 23.0±1.9 ✓ |
| ATR Verio (ATV) | 77 | 60/17 | 22.6±2.0 | 0 | - | - | 0 | - | - | 0 | - | - | 0 | - | - | 77 | 60/17 | 22.6±2.0 ✓ |
| Hiroshima Univ. Hospital (HUH) | 66 | 29/37 | 34.6±13.0 | 57 | 25/32 | 43.3±12.2 | 0 | - | - | 0 | - | - | 0 | - | - | 123 | 54/69 | 39.6±13.3 - |
| Hiroshima Kajikawa Hospital (HKH) | 29 | 12/17 | 46.4±9.5 | 23 | 10/13 | 43.6±11.6 | 0 | - | - | 0 | - | - | 0 | - | - | 52 | 22/30 | 44.6±10.5 ✓ |
| Center of Innovation in Hiroshima Univ. (COI) | 10 | 5/5 | 43.5±10.5 | 36 | 18/20 | 44.0±11.0 | 0 | - | - | 0 | - | - | 0 | - | - | 46 | 23/25 | 43.9±11.4 ✓ |
| Kyoto Prefectural University of Medicine (KPM) | 52 | 28/24 | 29.1±7.3 | 0 | - | - | 0 | - | - | 65 | 30/35 | 31.9±9.8 | 0 | - | - | 117 | 58/59 | 30.6±8.8 - |
| Kyoto University (KUT) | 35 | 16/17 | 36.3±8.9 | 9 | 3/4 | 45.2±15.9 | 0 | - | - | 0 | - | - | 22 | 10/11 | 40.4±8.4 | 34/32 | 38.9±10.2 ✓ |
| Showa University (SWA) | 40 | 32/8 | 30.9±8.5 | 0 | - | - | 46 | 45/4 | 32.0±8.1 | 0 | - | - | 12 | 11/1 | 41.8±9.2 | 101 | 88/13 | 33.2±8.9 ✓ |
| University of Tokyo (UTO) | 142 | 72/70 | 39.7±11.0 | 34 | 16/18 | 39.5±8.9 | 0 | - | - | 0 | - | - | 14 | 7/7 | 33.3±14.0 | 190 | 95/95 | 31.6±11.5 ✓ |
| Summary | 482 | 284/198 | 30.6±10.9 | 161 | 74/87 | 42.6±11.7 | 46 | 45/4 | 32.0±8.1 | 65 | 30/35 | 31.9±9.8 | 48 | 29/19 | 39.7±10.8 | 805 | 462/343 | 33.7±11.9 - |

*1: PARTICIPANTS WERE SCANNED USING STANDARDIZED PROTOCOLS

Fig. 16

| RESTING STATE fMRI IMAGING PROTOCOL IN SRPBS MULTI-DISEASE DATASET | | | | | | | | | |
|---|---|---|---|---|---|---|---|---|---|
| SITE | ATR TimTrio | ATR Verio | Center of Innovation in Hiroshima University | Hiroshima Univ. Hospital | Hiroshima Kajikawa Hospital | Kyoto Prefectural Univ. of Medicine University | Showa University | Kyoto University TimTrio | University of Tokyo |
| ABBREVIATION | ATT | ATV | COI | HUH | HKH | KPM | SWA | KUT | UTO |
| MRI SCANNER | Siemens TimTrio | Siemens Verio | Siemens Verio | GE Signal HDxt | Siemens Spectra | Philips Achieva | Siemens Verio | Siemens TimTrio | GE MR750w |
| STATIC MAGNETIC FIELD STRENGTH | 3.0 T | 3.0 T | 3.0 T | 3.0 T | 3.0 T | 3.0 T | 3.0 T | 3.0 T | 3.0 T |
| NUMBER OF RECEIVING COILS | 12 | 12 | 12 | 8 | 12 | 8 | 12 | 32 | 24 |
| FIELD OF VIEW (mm) | 212×212 | 212×212 | 212×212 | 256×256 | 192×192 | 192×192 | 212×212 | 212×212 | 212×212 |
| MATRIX | 64×64 | 64×64 | 64×64 | 64×64 | 64×64 | 64×64 | 64×64 | 64×64 | 64×64 |
| SLICE NUMBER | 40 or 39 | 39 | 40 | 32 | 38 | 39 | 40 | 40 | 40 |
| VOLUME NUMBER | 240 | 240 | 240 | 143 | 107 | 194 | 240 | 240 | 240 |
| IN-PLANE RESOLUTION | 3.3125×3.3125 | 3.3125×3.3125 | 3.3125×3.3125 | 4.0×4.0 | 3.0×3.0 | 3.0×3.0 | 3.3125×3.3125 | 3.3125×3.3125 | 3.3125×3.3125 |
| SLICE THICKNESS (mm) | 3.2 | 3.2 | 3.2 | 3.2 | 3.0 | 3.0 | 3.2 | 3.2 | 3.2 |
| SLICE GAP (mm) | 0.8 | 0.8 | 0.8 | 0 | 0 | 0 | 0.8 | 0.8 | 0.8 |
| TR (ms) | 2,500 | 2,500 | 2,500 | 2,000 | 2,700 | 2,000 | 2,500 | 2,500 | 2,500 |
| TE (ms) | 30 | 30 | 30 | 27 | 31 | 30 | 30 | 30 | 30 |
| TOTAL SCAN TIME (min's) | 10:00 | 10:00 | 10:00 | 5:00 | 5:00 | 6:30 | 10:00 | 10:00 | 10:00 |
| FLIP ANGLE (deg) | 80 | 80 | 80 | 90 | 90 | 80 | 80 | 80 | 80 |
| SLICE GETTING ORDER | Ascending | Ascending | Ascending | Ascending | Ascending | Ascending | Ascending | Ascending | Ascending |
| PHASE ENCODING DIRECTION | PA | PA | PA | PA | AP | AP | PA | PA | PA |
| EYES CLOSED (Closed)/ FIXATE (Fixate) | Fixate | Fixate | Fixate | Fixate | Fixate | Fixate | Fixate | Fixate | Fixate |

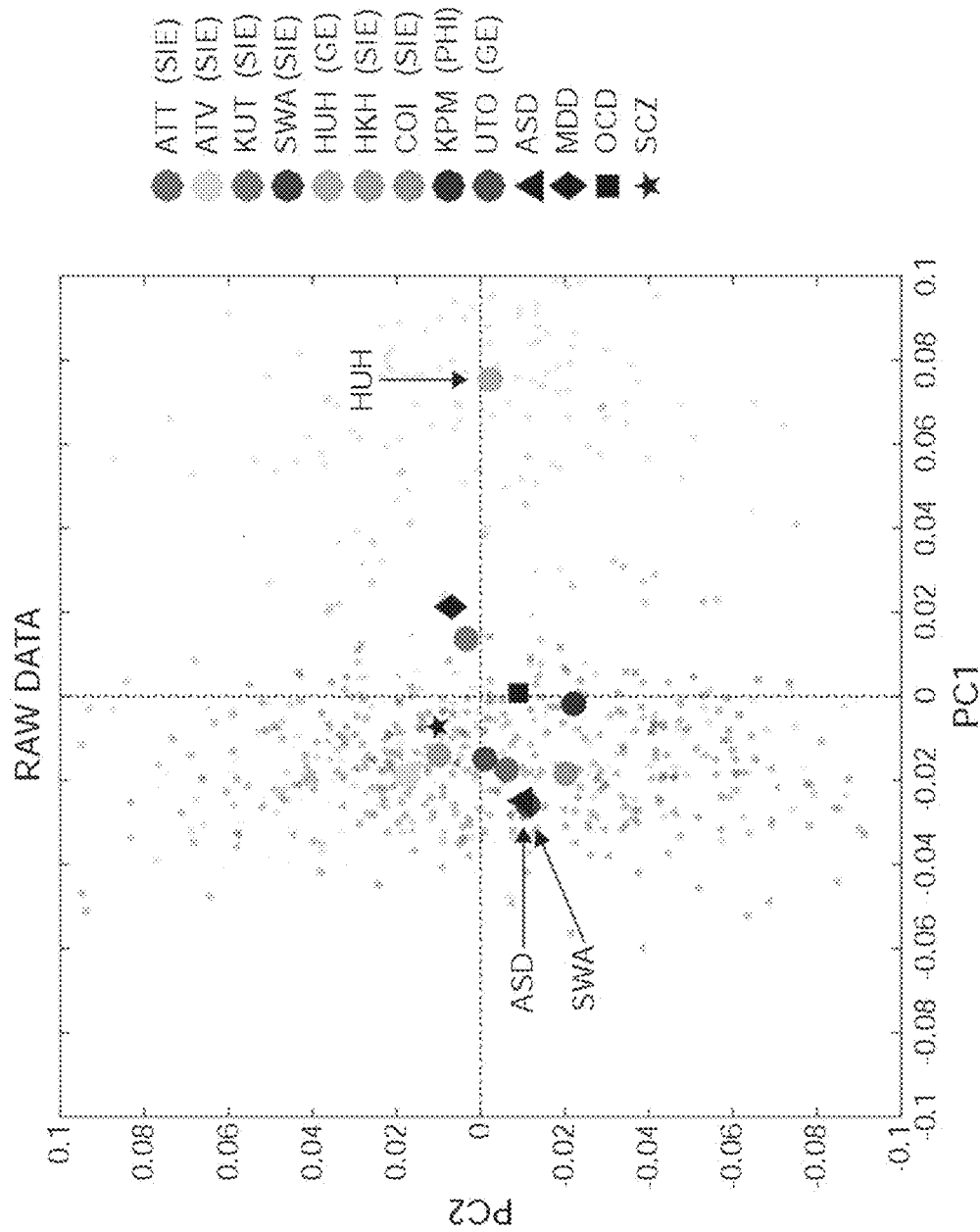

Fig. 30

DEMOGRAPHIC CHARACTERISTICS OF PATIENTS INCLUDED IN TRAINING DATASET

| SITE | HEALTHY CONTROL (HC) | | | | MDD PATIENTS (MDD) | | | | SUM | | | |
|---|---|---|---|---|---|---|---|---|---|---|---|---|
| | NUMBER OF PARTICIPANTS | MALE/FEMALE | AGE | BDI | NUMBER OF PARTICIPANTS | MALE/FEMALE | AGE | BDI | NUMBER OF PARTICIPANTS | MALE/FEMALE | AGE | BDI |
| SITE 1 (COI) | 124 (123) | 46/78 | 51.9±13.4 | 8.2±6.3 | 70 (70) | 31/39 | 45.0±12.5 | 26.2±9.9 | 194 (193) | 77/117 | 49.4±13.5 | 14.7±11.7 |
| SITE 2 (KUT) | 169 (139) | 100/69 | 35.9±13.6 | 6.0±5.4 | 17 (17) | 11/6 | 43.9±13.3 | 27.7±10.1 | 186 (156) | 111/75 | 36.7±13.7 | 8.3±9.1 |
| SITE 3 (SWA) | 101 (97) | 86/15 | 28.4±7.9 | 4.4±3.8 | 0 | - | - | - | 101 (97) | 86/15 | 28.4±7.9 | 4.4±3.8 |
| SITE 4 (UTO) | 170 (24) | 78/92 | 35.6±17.5 | 6.7±6.5 | 62 (32) | 36/26 | 38.7±11.6 | 20.4±11.4 | 232 (56) | 114/118 | 36.4±16.2 | 14.5±11.8 |
| TOTAL | 564 (383) | 310/254 | 38.0±16.1 | 6.3±5.6 | 149 (119) | 78/71 | 42.3±12.5 | 24.9±10.7 | 713 (502) | 388/325 | 38.9±15.5 | 10.7±10.6 |

Fig. 31

DEMOGRAPHIC CHARACTERISTICS OF PATIENTS INCLUDED IN INDEPENDENT VALIDATION DATASET

| SITE | HEALTHY CONTROLS (HC) | | | | MDD PATIENTS (MDD) | | | | SUM | | | |
|---|---|---|---|---|---|---|---|---|---|---|---|---|
| | NUMBER OF PARTICIPANTS | MALE/ FEMALE | AGE | BDI | NUMBER OF PARTICIPANTS | MALE/ FEMALE | AGE | BDI | NUMBER OF PARTICIPANTS | MALE/ FEMALE | AGE | BDI |
| SITE 5 (HKH) | 29 (29) | 12/17 | 45.4± 9.5 | 5.1±4.6 | 33 (33) | 20/13 | 44.8± 11.5 | 28.5±8.7 | 62 (62) | 32/30 | 46.1± 10.5 | 17.6±13.7 |
| SITE 6 (HRC) | 49 (49) | 13/36 | 41.7± 11.7 | 9.1±8.5 | 16 (16) | 6/10 | 40.5± 11.5 | 35.3±9.5 | 65 (65) | 19/46 | 41.4± 11.5 | 15.6±14.3 |
| SITE 7 (HUH) | 66 (66) | 29/37 | 34.6± 13.0 | 6.9±5.9 | 57 (57) | 32/25 | 43.3± 12.2 | 30.9±9.0 | 123 (123) | 61/62 | 38.6± 13.3 | 18.0±14.1 |
| SITE 8 (UYA) | 120 (120) | 50/70 | 45.9± 19.5 | 7.1±5.6 | 79 (78) | 36/43 | 50.3± 13.6 | 29.7±10.7 | 199 (198) | 86/113 | 47.6± 17.5 | 16.0±13.6 |
| TOTAL | 264 (264) | 104/160 | 42.2± 16.5 | 7.2±6.3 | 185 (184) | 94/91 | 46.3± 13.0 | 30.3±9.9 | 449 (448) | 198/251 | 43.9± 15.3 | 16.7±13.9 |

PREDICTION PERFORMANCE OF BDI SCORES
(TRAINING DATASET)

PREDICTION PERFORMANCE OF BDI SCORES
(INDEPENDENT VALIDATION DATASET)

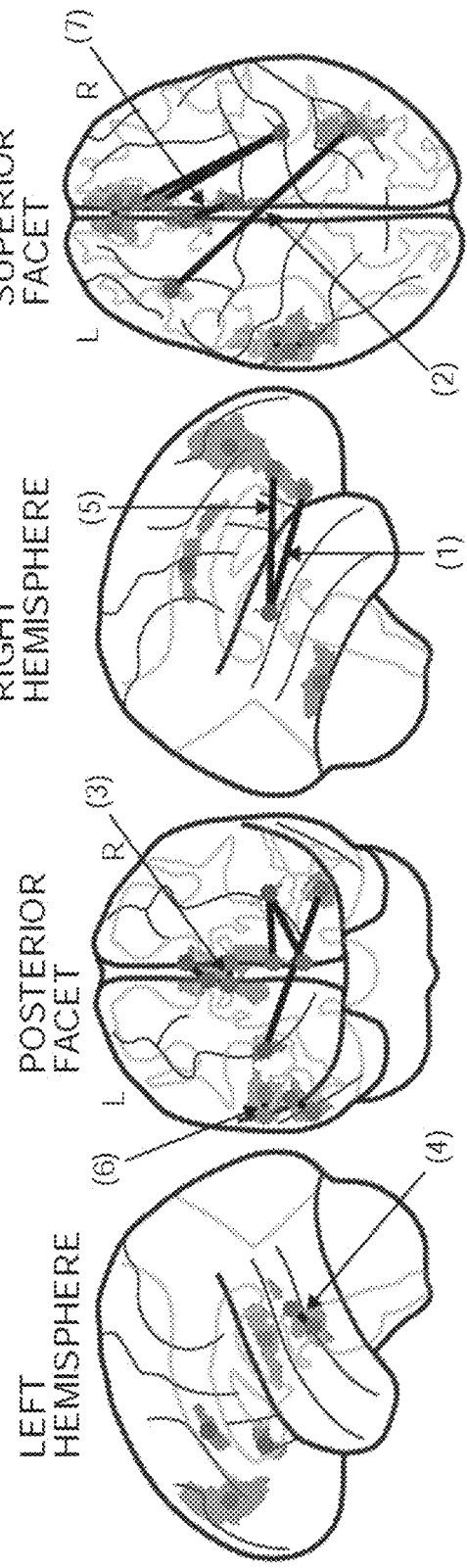

Fig. 42

| | COMMON FUNCTIONAL CONNECTIVITIES AND WEIGHTS IN BDI SCORE REGRESSION MODEL | | | | | | |
|---|---|---|---|---|---|---|---|
| | ROI1 | | | ROI2 | | | |
| ID | GLASSER'S NAMES OF REGIONS | AAL LABEL | NETWORK | GLASSER'S NAMES OF REGIONS | AAL LABEL | NETWORK | WEIGHT |
| 1 | R.52 | R.Insula | SALIENCE | R.s32 | R.Frontal_Med_Orb | DEFAULT MODE | -4.84 |
| 2 | L.FOP5 | L.Insula | SALIENCE | R.FFC | R.Fusiform | UNKNOWN | 4.12 |
| 3 | L.9m | L.Frontal_Sup_Medial | DEFAULT MODE | R.9m | R.Frontal_Sup_Medial | DEFAULT MODE | -4.02 |
| 4 | L.STSvp | L.Temporal_Mid | DEFAULT MODE | L.TE1m | L.Temporal_Mid | DEFAULT MODE | -3.80 |
| 5 | R.52 | R.Insula | SALIENCE | R.a24 | R.Cingulum_Ant | DEFAULT MODE | -1.71 |
| 6 | L.PBelt | L.Temporal_Sup | AUDITORY | L.A4 | L.Temporal_Sup | AUDITORY | -0.78 |
| 7 | L.a24pr | L.Cingulum_Mid | SALIENCE | R.p24pr | R.Cingulum_Mid | SALIENCE | -0.17 |

BRAIN FUNCTIONAL CONNECTIVITY CORRELATION VALUE ADJUSTMENT METHOD, BRAIN FUNCTIONAL CONNECTIVITY CORRELATION VALUE ADJUSTMENT SYSTEM, BRAIN ACTIVITY CLASSIFIER HARMONIZATION METHOD, BRAIN ACTIVITY CLASSIFIER HARMONIZATION SYSTEM, AND BRAIN ACTIVITY BIOMARKER SYSTEM

TECHNICAL FIELD

The present invention relates to a technique of adjusting brain functional connectivity correlation values measured by brain function imaging by a plurality of devices, a method of harmonizing brain activity classifiers using brain function imaging, a system for harmonizing brain activity classifiers and brain activity biomarker system. The present application claims the convention priority on Japanese Patent Application No. 2018-192842 filed on Oct. 11, 2018 and Japanese Patent Application No. 2019-034887 filed on Feb. 27, 2019, and herein incorporates the entire descriptions of these Japanese patent applications.

BACKGROUND ART (Biomarker)

When biological information is converted into a numerical value or quantified as an index for quantitatively comprehending any biological changes in a living body, it is called a "biomarker."

The FDA (the United States Food and Drug Administration) defines a biomarker as "a characteristic that is objectively measured and evaluated as an indicator of normal biological processes, pathogenic processes or pharmacological responses to a therapeutic intervention." Biomarkers representative of a state of or a change in a disease, or a degree of healing are used as surrogate markers (substitute markers) to monitor efficacy in clinical tests of new drugs. The blood sugar level, the cholesterol level and the like, are representative biomarkers used as indexes of lifestyle diseases. Biomarkers include not only substances of biological origin contained in urine or blood but also electrocardiogram, blood pressure, PET images, bone density, lung function, and the like. Developments in genomic analysis and proteome analysis have led to the discovery of various biomarkers related to DNA, RNA or biological protein.

Biomarkers are promising for measuring therapeutic efficacy after the onset of a disease and, in addition, as routine preventive indexes, promising for disease prevention. Further, application of biomarkers to individualized medicine for selecting effective treatment avoiding side effects is expected. In the field of neurological/mental disorders, however, though molecular markers and the like usable as objective indexes from a biochemical or molecular genetics viewpoint have been studied, it should in fairness be stated that they are still in a research phase.

Meanwhile, a disease determination system has been reported which uses an NIRS (Near-InfraRed Spectroscopy) technique to classify mental disorders such as schizophrenia and depression based on features of hemoglobin signals measured by biological optical measurement (Patent Literature 1). Disclosure of the Patent Literature 1 is incorporated herein by reference in its entirety.

(Biomarker Based on Brain Activities)

On the other hand, in Magnetic Resonance Imaging (MRI), changes appearing in detected signals in accordance with changes in the blood stream make it possible to visualize an active portion of a brain activated in response to an external stimulus. Such a nuclear magnetic resonance imaging is specifically referred to as fMRI (functional MRI).

An fMRI uses a common MRI apparatus with additional hardware and software necessary for fMRI measurement.

The changes in blood stream cause changes in NMR signal intensity, since oxygenated hemoglobin and deoxygenated hemoglobin in the blood have different magnetic properties. Oxygenated hemoglobin is diamagnetic and does not have any influence on relaxation time of hydrogen atoms in the surrounding water. In contrast, deoxygenated hemoglobin is paramagnetic and changes surrounding magnetic field. Therefore, when the brain receives any stimulus and local blood stream increases and oxygenated hemoglobin increases, the change can be detected by MRI signals. The stimulus to a subject may include, for example, visual stimulus, audio stimulus, or performance of a prescribed task (see, for example, Patent Literature 2). Disclosure of the Patent Literature 2 is incorporated herein by reference in its entirety.

Note that, in the studies of the brain functions, brain activities are measured by measuring increase in the nuclear magnetic resonance signal (MRI signal) of hydrogen atoms representing a phenomenon where the deoxygenated hemoglobin level in red blood cells decrease in minute veins or capillary vessels (BOLD effect).

The blood oxygen level dependent signal that reflects a brain activity measured by fMRI devices is referred to as a BOLD signal (Blood Oxygen Level Dependent Signal).

Particularly, in studies related to the human motor functions, brain activities are measured by the MRI apparatus as described above while a subject or subjects are performing some physical activity.

For human subjects, it is necessary to measure the brain functions in a non-invasive manner. In this aspect, a decoding technique has been developed that extracts more detailed information from fMRI data (see, for example, the Non-Patent Literature 1). Disclosure of the Non-Patent Literature 1 is incorporated herein by reference in its entirety. Specifically, a voxel-by-voxel (voxel: volumetric pixel) brain activity analysis of the brain by the fMRI enables the estimation of stimulus input or the state of recognition from spatial patterns of the brain activities.

Further, as a development of such a decoding technique, Patent Literature 3 discloses a method of brain function analysis for realizing biomarkers based on functional brain imaging for a neurological/mental disorder. Disclosure of the Non-Patent Literature 3 is incorporated herein by reference in its entirety. According to this method, from measurement data of resting-state functional connection MRI of a healthy cohort and a patient cohort, a correlation matrix of degrees of activities between prescribed brain regions is derived for each subject. Feature extraction is performed by regularized canonical correlation analysis on the correlation matrix and on the attributes of subjects including diseased/healthy labels of the subjects. Based on the results of regularized canonical correlation analysis, a discriminator that functions as a biomarker is generated from discriminant analysis by sparse logistic regression (SLR). It has been indicated that by such a technique of machine learning, results of mental disease diagnosis can be predicted based on connections among brain regions derived from fMRI data in the resting state. Further, verification of the prediction performance indicated that the prediction is not only applicable to the brain activities measured in a certain facility but also generalizable, to some extent, to the brain activities measured in a different facility.

Further, technical improvements are made to enhance generalization capability of the above-described biomarkers (Patent Literature 4). Disclosure of the Non-Patent Literature 4 is incorporated herein by reference in its entirety.

Recently, as in the human connectome project in the United States, obtaining and sharing large scale brain image data come to be recognized as having a significant meaning in filling in the gaps between basic neuro-scientific research and clinical applications such as diagnosis and therapy of mental diseases (Non-Patent Literature 2). Disclosure of the Non-Patent Literature 2 is incorporated herein by reference in its entirety.

In 2013, Japan Agency for Medical Research and Development, which is one of the Japanese National Research and Development Agencies, organized a Decoded Neurofeedback (DecNef) project, in which eight laboratories collect data of functional magnetic resonance in resting state (resting state functional MRI) covering five diseases and 2,239 samples from a plurality of sites, and the data is shared through a database (https://bicr-resource.atr.jp/decnefpro/) of a plurality of diseases at a plurality of sites mainly of SRPBS (Strategic Research Program for Brain Science, https://www.amed.go.jp/program/list/01/04/001_no-pro.html). This project identified biomarkers based on resting state functional connectivity (resting state functional MRI) of several mental diseases that can be generalized to fully independent cohorts.

It is noted, however, that it is difficult to collect massive brain image data from healthy people and significantly more difficult from patients.

Further, when measurements are done at a plurality of sites in order to massively collect data, the site-to-site differences of measurement data at each measuring site will be a problem.

By way of example, for evaluating the site-to-site differences of measurement data when MRI measurements are done at a plurality of measurement sites, adoption of a so-called "traveling subject" is proposed wherein a large number of participants travel to and are measured at the plurality of sites, in order to evaluate an effect on measurement bias on the resting state functional connectivity (Non-Patent Literatures 3 and 4). Disclosure of the Non-Patent Literature 3 and disclosure of the Non-Patent Literature 4 are incorporated herein by reference in their entirety.

CITATION LIST

Patent Literature

Patent Literature 1: WO2006-132313
Patent Literature 2: JP2011-000184A
Patent Literature 3: JP2015-62817A
Patent Literature 4: JP2017-196523A Non-Patent Literature Non-Patent Literature 1: Kamitani Y, Tong F. Decoding the visual and subjective contents of the human brain. Nat Neurosci. 2005; 8: 679-85.
Non-Patent Literature 2: Glasser M F, et al. The Human Connectome Project's neuroimaging approach. Nat Neurosci 19, 1175-1187 (2016).
Non-Patent Literature 3: Noble S, et al. Multisite reliability of MR-based functional connectivity. Neuroimage 146, 959-970 (2017).
Non-Patent Literature 4: Pearlson G. Multisite collaborations and large databases in psychiatric neuroimaging advantages, problems, and challenges. Schizophr Bull 35, 1-2 (2009).

SUMMARY OF INVENTION

Technical Problem

When we consider application to treatment of a neurological/mental disorder of the brain activity analysis by functional brain imaging such as functional Magnetic Resonance Imaging as described above, the analysis of brain activities using functional brain imaging as the above-described biomarker is promising as a non-invasive functional marker, and applications to development of a diagnostic method and to searching/identification of target molecules aiming toward drug discoveries for realizing basic remedies are also expected.

By way of example, consider a mental disorder such as autism. Practical biomarkers using genes are not yet established and, therefore, the development of therapeutic agents remains difficult, since it is difficult to determine the effect of medication.

In order to generate a discriminator by machine learning based on the measured data of brain activities and to practically use this as a biomarker, it is necessary to improve the prediction accuracy of the biomarker generated by machine learning for brain activities measured at one facility. Further, it is necessary that the biomarker generated in this manner can be generalized to brain activities measured at other facilities.

Specifically, when a discriminator is to be built by machine learning based on the measured data of brain activities, the following two main problems must be addressed.

The first problem is the small size of samples.

The amount of data N representing the number of subjects is far smaller than the dimension M of measured data of brain activities, and parameters of the discriminator will easily be over-fitted to the training data.

Because of this over-fitting, the discriminator thus built exhibits very poor performance on newly sampled test data. The reason for this is that the test data were not used for training the discriminator.

Therefore, in order to discriminate and use essential features only with respect to desired generalization of the discriminator, appropriate regularization must be introduced.

The second problem is that the discriminator is clinically effective and scientifically reliable only when the built discriminator maintains satisfactory performance on MRI data scanned at an imaging site different from the site where the training data were collected. This is a so-called generalization capability over a plurality of imaging sites.

Assume that massive brain image data related to mental disease are to be collected. The amount of data of brain images that can be obtained at one site is limited and, therefore, collection from a plurality of sites becomes necessary. The site-to-site differences, however, pose the biggest problem when brain image data are to be obtained from a plurality of sites. Specifically, in clinical applications, it is often observed that a discriminator trained by using data obtained at a specific site cannot be generalized to data scanned at a different site.

Therefore, in the human connectome project mentioned above, it is assumed that measurements are done at a single site, using a single scanner.

The present invention was made to solve the above-described problem and its object is to provide a method of adjusting functional connectivity correlation values and a system for adjusting functional connectivity correlation values, that can adjust and correct measurement bias at various facilities based on the brain measurement data obtained from a plurality of facilities.

Another object of the present invention is to provide a method of harmonizing a brain activity classifier, a system for harmonizing a brain activity classifier, a brain activity analyzing device and a brain activity analyzing method, that harmonize brain measurement data obtained from a plurality of facilities to realize a discriminating process based on brain functional imaging, for supporting diagnosis of neurological/mental diseases.

A further object of the present invention is to provide a brain activity analyzing device, a brain activity analyzing method and brain activity biomarker system and a program for the brain activity biomarker system, for realizing a biomarker based on brain activity measurements.

Solution to Problem

According to an aspect, the present invention provides a method of adjusting a brain functional connectivity correlation value of subjects measured at a plurality of measurement sites, including the steps of: for a plurality of traveling subjects as common objects of measurements at each of the plurality of measurement sites, measuring brain activities of a predetermined plurality of brain regions of each of the traveling subjects: calculating, for each of the traveling subjects, prescribed elements of a brain functional connectivity matrix representing temporal correlation of brain activities of a set of the plurality of brain regions; using a generalized linear mixed model, calculating measurement bias for each element by of the brain functional connectivity matrix, as a fixed effect at each measurement site with respect to an average of the corresponding element across the plurality of measurement sites and across the plurality of traveling subjects; and using the measurement bias, correcting a brain functional connectivity correlation value as the prescribed elements of the brain functional connectivity matrix of a subject measured at each of the measurement sites and thereby obtaining an adjusted value.

According to another aspect, the present invention provides a brain functional connectivity correlation value adjustment system for correcting a brain functional connectivity correlation value of an object, including: a plurality of brain activity measurement devices provided respectively at a plurality of measurement sites, for time-sequentially measuring brain functions of a plurality of subjects; and a computing system for correcting the brain functional connectivity correlation value: the computing system includes a storage device for storing data, the storage device storing results of measurements of brain activities of a predetermined plurality of brain regions of each of a plurality of traveling subjects who are common objects of measurements at each of the plurality of measurement sites; the computing system further includes a processor; wherein the processor calculates, for each of the traveling subjects, prescribed elements of a brain functional connectivity matrix representing temporal correlation of brain activities of a set of the plurality of brain regions; using a generalized linear mixed model, calculates a measurement bias for each element of the brain functional connectivity matrix, as a fixed effect at each measurement site with respect to an average of the corresponding element across the plurality of measurement sites and across the plurality of traveling subjects; and using the measurement bias, corrects a brain functional connectivity correlation value as the prescribed elements of the brain functional connectivity matrix of a subject measured at each of the measurement sites and thereby obtaining an adjusted value.

According to a further aspect, the present invention provides a method of harmonizing a brain activity classifier for executing a process of classification of at least one attribute of a plurality of subjects measured at a plurality of measurement sites, including the steps of: for a plurality of traveling subjects as common objects of measurements at each of the plurality of measurement sites, measuring brain activities of a predetermined plurality of brain regions of each of the traveling subjects: calculating, for each of the traveling subjects, prescribed elements of a brain functional connectivity matrix representing the temporal correlation of brain activities of a set of the plurality of brain regions; using the generalized linear mixed model, calculating a measurement bias for each element of the brain functional connectivity matrix, as a fixed effect at each measurement site with respect to an average of the corresponding element across the plurality of measurement sites and across the plurality of traveling subjects; and using the measurement bias, correcting a brain functional connectivity correlation value as the prescribed elements of the brain functional connectivity matrix of a subject measured at each of the measurement sites and thereby obtaining an adjusted value; and generating a classifier for the attribute through machine learning with feature selection, based on the adjusted value.

Preferably, the plurality of subjects as objects of training data subjected to measurements of brain activities at each of the plurality of measurement sites include a first group of subjects having the attribute and a second group of subjects not having the attribute; the step of calculating measurement bias includes the step of, using the generalized linear mixed model, calculating the measurement bias, the sampling bias of the first group and the sampling bias of the second group, for each element of the brain functional connectivity matrix, as fixed effects at each measurement site with respect to an average of the corresponding element across the plurality of measurement sites and across the plurality of traveling subjects.

More preferably, in the generalized linear mixed model, the measurement bias is calculated by least square regression by L2 normalization.

Further preferably, the machine learning with feature selection is a logistics regression analysis using LASSO (least absolute shrinkage and selection operator).

According to a still further aspect, the present invention provides a system for harmonizing a brain activity classifier for executing a process of classification of at least one attribute based on the results of the brain activity measurements of objects, including: a plurality of the brain activity measurement devices provided respectively at a plurality of the measurement sites, for time-sequentially measuring brain functions of a plurality of subjects; a computing system for correcting a brain functional connectivity correlation value as prescribed elements of a brain functional connectivity matrix representing the temporal correlation of brain activities of the subjects as objects of the training data; wherein the computing system includes a storage device for storing data, the storage device storing results of the measurements of brain activities of a predetermined plurality of brain regions of each of a plurality of traveling subjects who are common objects of measurements at each of the plurality of measurement sites; the computing system further includes a processor; wherein the processor calculates, for each of the traveling subjects, prescribed elements of the brain functional connectivity matrix, using a generalized linear mixed model, calculates a measurement bias for each element of the brain functional connectivity matrix, as a fixed effect at each measurement site with respect to an average of the corresponding element across the plurality of measurement sites and across the plurality of traveling subjects, using the measurement bias, corrects a brain functional connectivity correlation value as the prescribed elements of the brain functional connectivity matrix of a subject measured at each of the measurement sites and thereby obtaining an adjusted value, and generates a classifier for the attribute through machine learning with feature selection, based on the adjusted value.

Preferably, the plurality of subjects as objects of the training data subjected to measurements of brain activities at each of the plurality of measurement sites include a first group of subjects having the attribute and a second group of subjects not having the attribute; and in calculating the measurement bias, the processor calculates, using the generalized linear mixed model, a measurement bias, a sampling bias of the first group and a sampling bias of the second group, for each element of the brain functional connectivity matrix, as a fixed effect at each measurement site with respect to an average of the corresponding element across the plurality of measurement sites and across the plurality of traveling subjects.

Preferably, in the generalized linear mixed model, the measurement bias is calculated by least square regression by L2 normalization.

Preferably, the machine learning with feature selection is a logistics regression analysis using LASSO.

According to a still further aspect, the present invention provides a brain activity biomarker system using a brain activity classifier for executing a process of classification of at least one attribute related to the presence/absence of a disease based on the results of brain activity measurements of the objects, including: a plurality of brain activity measurement devices provided respectively at a plurality of measurement sites, for time-sequentially measuring brain functions of a plurality of subjects; and a computing system for correcting a brain functional connectivity correlation value as prescribed elements of a brain functional connectivity matrix representing the temporal correlation of brain activities of the subjects; wherein the computing system includes a storage device and a processor; and the processor calculates, by removing the measurement bias from the brain functional connectivity correlation values as the prescribed elements of the brain functional connectivity matrix of a plurality of subjects measured at each of the measurement sites, the corrected adjusted values respectively and stores them in the storage device, and based on the adjusted values, generates the brain activity classifier through machine learning accompanied by a first feature selection.

Preferably, the storage device stores in advance, the results of the measurements of brain activities of a predetermined plurality of brain regions of each of a plurality of traveling subjects who are common objects of measurements at each of the plurality of measurement sites; and the processor calculates, for each of the traveling subjects, prescribed elements of the brain functional connectivity matrix that represent the temporal correlation of brain activities of a set of the plurality of brain regions, and using a generalized linear mixed model, calculates a measurement bias for each element of the brain functional connectivity matrix, as a fixed effect at each measurement site with respect to an average of the corresponding element across the plurality of measurement sites and across the plurality of traveling subjects.

Preferably, the processor executes a process of classification of at least one attribute related to the presence/absence of a disease based on the measurement data of objects measured at any of the plurality of measurement sites.

Preferably, in the machine learning accompanied by the first feature selection, the processor i) divides the adjusted values to a training dataset for machine learning and a test dataset for validation; ii) executes under-sampling and sub-sampling a prescribed number of times on the training dataset to generate the prescribed number of subsamples; iii) for each subsample, generates a classifier sub-model by feature selection in accordance with sparse modeling; and iv) generates the brain activity classifier based on the feature selection in accordance with the sparse sampling.

Preferably, the machine learning accompanied by the first feature selection includes a nested cross-validation having external and internal cross-validations; in the nested cross-validation, the processor i) divides the adjusted values to a training dataset for machine learning and a test dataset for validation by conducting K-fold cross-validation as the external cross-validation; ii) executes under-sampling and sub-sampling a prescribed number of times on the training dataset to generate the prescribed number of subsamples; iii) in each loop of the K-fold cross-validation, generates a classifier sub-model for each subsample by the internal cross-validation; and iv) generates the brain activity classifier based on the classifier sub-model.

Preferably, the storage device stores information of an evaluation measure of the disease for each of the plurality of subjects; and the processor generates a regression model for the evaluation measures of the disease based on the adjusted values by machine learning accompanied by a second feature selection, and specifies a brain functional connectivity commonly extracted by the first and second feature selections.

According to a still further aspect, a computer program controlling a brain activity biomarker system using a brain activity classifier for executing a process of classification of at least one attribute related to the presence/absence of a disease based on the results of the brain activity measurements of objects, wherein the brain activity biomarker system includes: a plurality of the brain activity measurement devices provided respectively at a plurality of measurement sites, for time-sequentially measuring the brain functions of a plurality of subjects; and a computing system having a storage device and a processor, for correcting a brain functional connectivity correlation value as prescribed elements of a brain functional connectivity matrix representing the temporal correlation of the brain activities of the subjects; the computer program causes the processor to execute the steps of: calculating, by removing a measurement bias from the brain functional connectivity correlation values as the prescribed elements of the brain functional connectivity matrix of a plurality of subjects measured at each of the measurement sites, adjusted values respectively and storing them in the storage device, and based on the adjusted values, generating the brain activity classifier through machine learning accompanied by a first feature selection.

Preferably, the storage device stores in advance, the results of the measurements of brain activities of a predetermined plurality of brain regions of each of a plurality of traveling subjects who are common objects of measurements at each of the plurality of measurement sites; and the computer program causes the processor to execute the steps of: calculating, for each of the traveling subjects, prescribed elements of the brain functional connectivity matrix that represents the temporal correlation of the brain activities of a set of the plurality of brain regions; and using a generalized linear mixed model, calculating a measurement bias for each element of the brain functional connectivity matrix, as a fixed effect at each measurement site with respect to an average of the corresponding element across the plurality of measurement sites and across the plurality of traveling subjects.

Preferably, the processor is further caused to execute the step of classifying an attribute related to presence/absence of a disease based on measurement data of objects measured at any of the plurality of measurement sites.

Preferably, in the machine learning accompanied by the first feature selection, the processor executes the steps of: i) dividing the adjusted values to a training dataset for machine learning and a test dataset for validation; ii) executing under-sampling and sub-sampling a prescribed number of times on the training dataset to generate the prescribed number of subsamples; iii) for each subsample, generating a classifier sub-model by feature selection in accordance with sparse modeling; and iv) generating a classifier for the attribute related to presence/absence of a disease based on the feature selection in accordance with the sparse sampling.

Preferably, the machine learning accompanied by the first feature selection includes a nested cross-validation having external and internal cross-validations; in the nested cross-validation, the processor executes the steps of: i) dividing the adjusted values to a training dataset for machine learning and a test dataset for validation by conducting K-fold cross-validation as the external cross-validation; ii) executing under-sampling and sub-sampling a prescribed number of times on the training dataset to generate the prescribed number of subsamples; iii) in each loop of the K-fold cross-validation, generating a classifier sub-model for each subsample by the internal cross-validation; and iv) generating the brain activity classifier based on the classifier sub-model.

Preferably, the storage device stores information of an evaluation measure of the disease for each of the plurality of subjects; and the processor executes the steps of: generating a regression model for the evaluation measures of the disease based on the adjusted values by machine learning accompanied by the second feature selection, and specifying a brain functional connectivity commonly extracted by the first and second feature selections.

Advantageous Effects of Invention

According to the present invention, as regards the measurement data of brain activities measured at a plurality of facilities, it is possible to adjust and correct a measurement bias at various facilities. Consequently, it becomes possible to adjust brain functional connectivity correlation values based on measurement data at the plurality of facilities.

Further, according to the present invention, it becomes possible to realize a method of harmonizing a brain activity classifier, a system for harmonizing a brain activity classifier, a brain activity analyzing system and a brain activity analyzing method, that harmonize the measurement data of brain activities measured at a plurality of facilities to enable objective determination of healthy or diseased states.

According to the present invention, it becomes possible to realize a brain activity biomarker system and a program for the brain activity biomarker system utilizing brain function imaging in relation to neurological/mental diseases, based on the measurement data of brain activities measured at a plurality of facilities.

BRIEF DESCRIPTION OF DRAWINGS

FIG. 3 shows examples of "measurement parameters" and "subject attribute data."

FIG. 7 is an illustration showing how to express the b-th functional connectivity of a subject a.

FIG. 14 shows data of multi-disease database and traveling subject dataset used in the harmonization process.

FIG. 15 shows contents of multi-disease dataset of SRPBS.

FIG. 16 shows imaging protocols at various measurement sites.

FIG. 17 is a graph visualizing the site-to-site differences and disease effects based on a principal component analysis.

FIG. 30 shows demographic characteristics of the training dataset (first dataset).

FIG. 31 shows demographic characteristics of the independent validation dataset (second dataset).

FIG. 41 shows the spatial distribution of seven brain functional connections FC common in building the MDD classifier and the BDI regression model.

FIG. 42 shows a list indicating the characteristics of the common seven brain function connections FC

DESCRIPTION OF EMBODIMENTS

Figure 1:
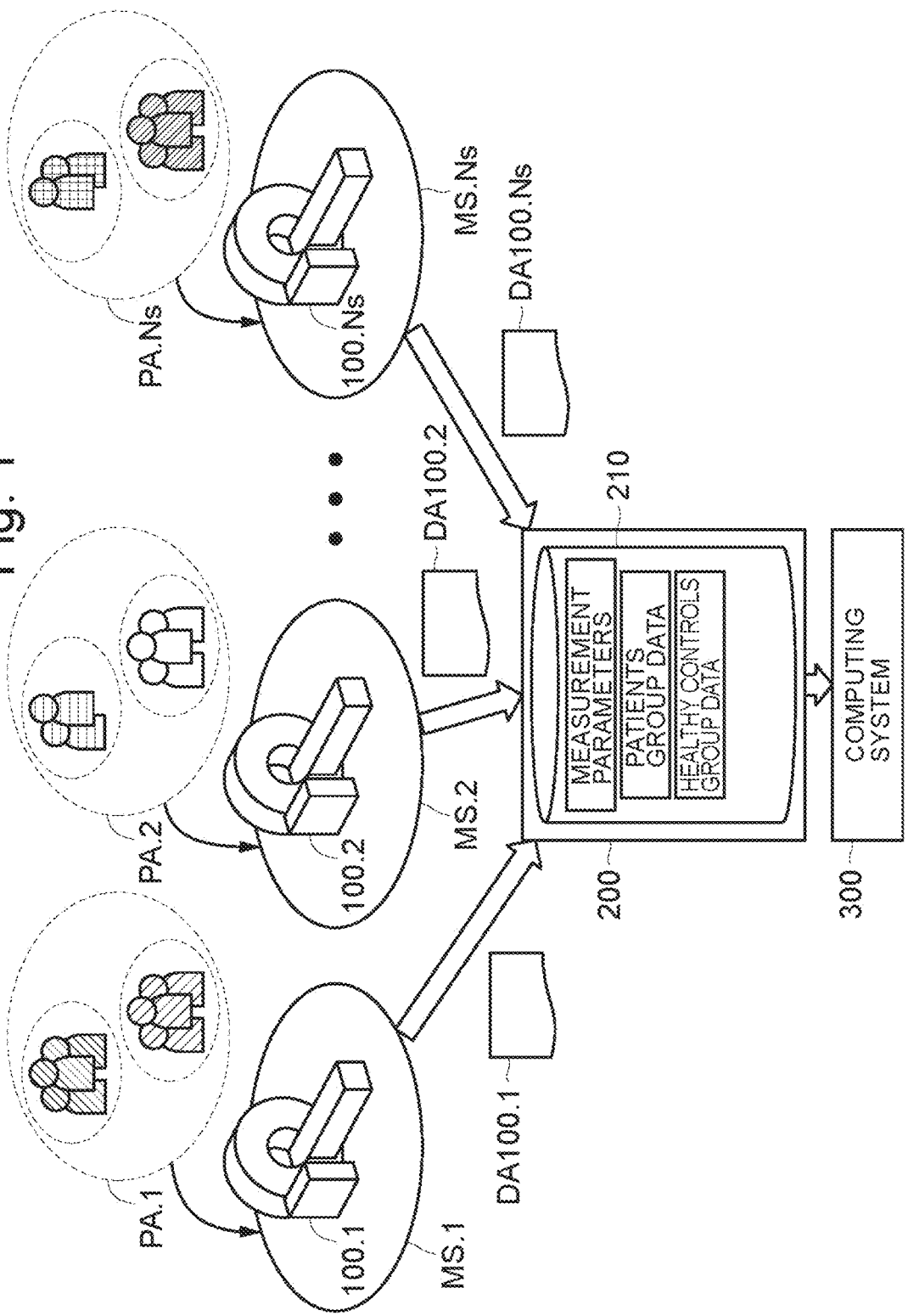
FIG. 1 is a schematic diagram illustrating a harmonization process on data measured by the MRI measurement systems installed at a plurality of measurement sites.

In the following, a configuration of an MRI measurement system in accordance with the embodiments of the present invention will be described with reference to the drawings. In the embodiments below, components or process steps denoted by the same reference characters are the same or corresponding components or steps and, therefore, descriptions thereof will not be repeated unless necessary.

In the following embodiments, the present invention is applied for time-sequentially measuring brain activities between a plurality of brain regions using "brain activity measuring devices" or, more specifically, "MRI measurement systems" installed at a plurality of facilities and for classifying subjects based on time-correlation patterns of these regions.

Such "MRI measurement systems" are installed at a plurality of different facilities and inherently involve the site-to-site differences in measurements (measurement facilities) including a measurement bias caused by different measurement devices and differences caused by the population of subjects (sampling bias), which are independently evaluated as will be described later. Then, for each measurement of each measurement site, a process is applied for correcting the site-to-site differences by removing the effects of measurement biases. Thus, harmonization of the measurement results among the measurement sites is realized.

First Embodiment

FIG. 1 is a schematic diagram illustrating a harmonization process on data measured by the MRI measurement systems installed at a plurality of measurement sites.

Referring to FIG. 1, it is assumed that MRI devices 100.1 to 100.$N_s$ are installed at measurement sites MS.1 to MS.$N_s$ ($N_s$: number of sites), respectively. At measurement sites MS.1 to MS.$N_s$, measurements of subject cohorts PA.1 to PA.$N_s$ are taken. Each of the subject cohorts PA.1 to PA.$N_s$ includes at least two cohorts to be classified, for example, a patient cohort and a healthy cohort. Though not limiting, a patient cohort includes patients of mental diseased and, more specifically, a cohort of "patients of major depressive disorder."

Further, it is assumed that at each measurement site, in principle, measurements of subjects are taken through measurement protocols as standardized as possible considering different specifications of MRI devices.

Though not specifically limited here, the measurement protocols define, by way of example, the following.

1) Direction of Scanning Subject's Head

It is necessary to prescribe whether the head scan is to be done in a direction from the back side (posterior: hereinafter denoted as "P") to the front side (anterior: hereinafter denoted as "A") (in the following, this direction will be referred to as "P→A direction") or the opposite direction, that is, from the front side to the back side (hereinafter referred to as "A→P direction"). Circumstances may require scanning in both directions.

Default scanning direction may differ from MRI device to device. In some devices, it is impossible to freely set or change the scanning direction.

The scanning direction possibly defines how an image is "distorted" and, hence, condition is set as a protocol.

2) Imaging Conditions for Brain Structural Images

Conditions are set for taking either "T1 weighted image" or "T2 weighted image" or both by a so-called spin echo.

3) Imaging Conditions for Brain Functional Images

Conditions are set for imaging brain functional images of subjects in the "resting state" by fMRI (functional Magnetic Resonance Imaging).

4) Imaging Conditions for Diffusion Weighted Images

Whether DWI (Diffusion (Weighted) Image) is to be obtained or not, and conditions therefor are set.

The diffusion weighted image is one type of MRI sequence, imaging diffusion of water molecules. In the spin echo pulse sequences usually used, signal attenuation caused by diffusion is negligible. When a large gradient magnetic field is continuously applied for a long time, however, phase shift caused by the movement of each magnetizing vector during that time becomes considerable and a region of more vigorous diffusion comes to appear as having lower signals. The diffusion weighted image utilizes this phenomenon.

5) Imaging for Correcting EPI Distortion by Image Processing

As a method of correcting EPI distortion by image processing, "field mapping" has been known and thus, conditions for imaging with respect to correction of spatial distortion are set.

In field mapping, EPI images are collected by multiple echo times, and based on these EPI images, the amount of EPI distortion is calculated. By applying the field mapping, it is possible to correct EPI distortion included in a new image. On the premise of a set of images of the same anatomical structure with different echo time, EPI distortion can be calculated and image distortion can be corrected.

For example, "field mapping" is described in known Reference 1 below. The disclosure of Reference 1 is incorporated herein by reference in its entirety.

Reference 1: JP2015-112474 A

Measurement protocols may include excerpts of necessary sequence portions of the conditions described above, or may have other sequences or conditions added as needed.

Referring to FIG. 1 again, picking up subjects to be measured at respective measurement sites MS.1 to MS.$N_s$ will be referred to as "sampling," and the cause of the site-to-site differences of measurements resulting from bias in the sampling at various measurement sites will be referred to as a "sampling bias."

In the example above, it is known that patients diagnosed as having "major depressive disorder" actually include several sub-types.

Typically, the sub-types include melancholic MDD, non-melancholic MDD and treatment-resistant MDD. At the measurement sites, due to various factors such as bias in nature caused by the locality of patients visiting hospitals of the measurement sites and the tendency of diagnosis at the hospitals, the distribution of sub-types among patients having "major depressive disorder" is not always uniform. As a result, it is common that the sub-type distribution among patients of the various measurement sites is biased, and hence, the "sampling bias" mentioned above is generated.

Further, even in a group of subjects referred to as "healthy cohort," a plurality of sub-types exists in general, and in this point also, the "healthy cohort" also has a "sampling bias."

Further, as regards MRI devices 100.1 to 100.$N_s$, it is not always the case that MRI devices having the same measurement characteristics are used at respective measurement sites.

The site-to-site differences among measurement sites may be generated depending on the conditions of the MRI devices and the measurement conditions of the MRI devices, such as the manufacturers of the MRI devices, the model numbers of the MRI devices, the static magnetic field strength in the MRI devices, the number of coils (number of channels) of (transmitting) receiving coils of the MRI devices. Site-to-site differences resulting from such measurement conditions are referred to as "measurement biases."

Even MRI devices of the same model number manufactured by the same manufacturer do not always realize perfectly identical measurement characteristics, due to the inherent uniqueness of each device.

Here, as the (transmitting) receiving coil, generally, a "multi-array coil" is used in order to improve the signal-to-noise ratio of measured signals. The "number of receiving coils" means the number of "element coils" forming the multi-array coil. By improving the sensitivity of each element coil and by bundling the outputs, the receiving sensitivity is improved.

In the present invention, it becomes possible to independently evaluate the "sampling bias" and the "measurement bias" by the method as will be described later.

Referring back to FIG. 1, measurement-related data DA100.1 to DA100.$N_s$ obtained from respective measurement sites MS.1 to MS.$N_s$ are accumulated and stored in a storage device 210 in a data center 200.

Here, "measurement-related data" includes "measurement parameters" of respective measurement sites, as well as "patient cohort data" and "healthy cohort data" measured at respective measurement sites.

Further, "patient cohort data" and "healthy cohort data" include, for each subject, "patient MRI measurement data" and "healthy person MRI measurement data," respectively.

Figure 2:
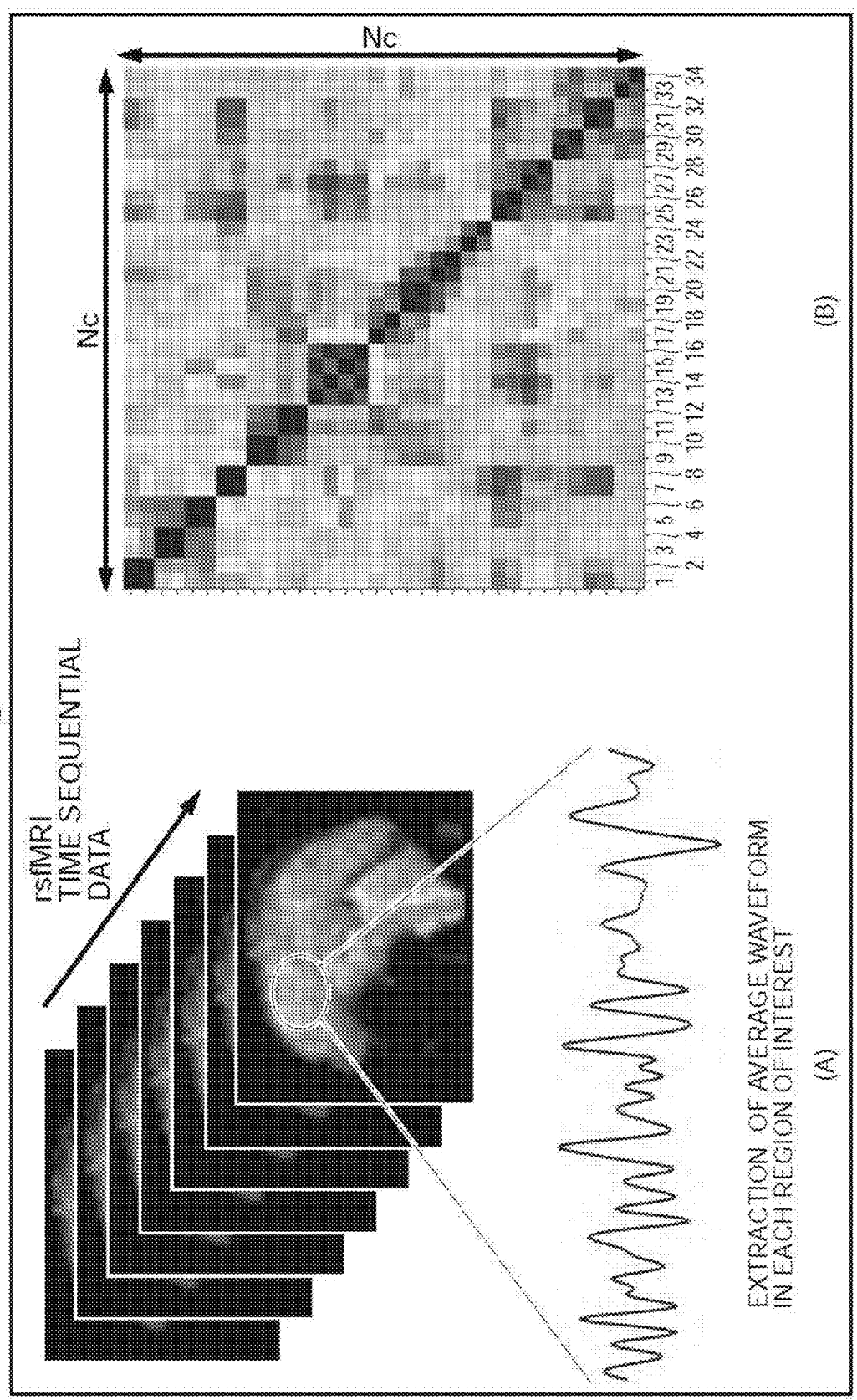
FIG. 2 is a schematic illustration showing a procedure for extracting a correlation matrix representing the correlation of functional connectivity in the resting state of Regions of Interest (ROIs) of a subject's brain.

In the following, we will describe the "measurement-related data." FIG. 2 is a schematic illustration showing a procedure for extracting a correlation matrix representing the correlation of functional connectivity in a resting state of Regions of Interest (ROIs) of a subject's brain.

Here, referring to FIG. 1, the "patient MRI measurement data" and the "healthy person MRI measurement data in the "patient cohort data" and the "healthy cohort data" include at least the following data.

i) Time-Sequential "Brain Function Image Data" for Calculating a Correlation Matrix Data and/or a Correlation Matrix Data Itself.

Specifically, when computing system 300 shown in FIG. 1 calculates the brain activity biomarker as will be described later based on data stored in storage device 210, the data mentioned above is used.

Here, the correlation matrix data may be calculated at each measurement site based on time-sequential "brain function image data," stored in storage device 210, and the computing system 300 may calculate the brain function biomarker based on the data of the correlation matrix stored in storage device 210.

Alternatively, time-sequential "brain function image data" may be stored in storage device 210, and computing system 300 may calculate the correlation matrix data stored in storage device 210 and may further calculate the brain activity biomarker.

Therefore, each of the "patient's MRI measurement data" and the "healthy person's MRI measurement data" at least includes one of the time-sequential "brain function image data" for calculating the correlation matrix data or the correlation matrix data itself.

ii) Subject's Structural Image Data and Diffusion Weighted Image Data

Though not specifically limited, the process for correcting EPI distortion may be done after the operation is done at each measurement site and the resulting data is stored in storage device 210.

Further, though not specifically limited, from the view point of protecting personal information, before storing data in the storage device 210, an anonymization process may be executed at each measurement site. The anonymization process, however, may be executed by computing system 300 if the operator of computing system 300 is legally authorized to handle personal information.

Returning to FIG. 2, as shown in FIG. 2(A), from fMRI data of n (n: a natural number) time points in the resting state measured on a real-time basis, an average "degree of activity" of each region of interest is calculated, and as shown in FIG. 2(B), the correlation matrix of functional connectivity ("correlation value of activities") among the brain regions (among the regions of interest) are calculated.

Functional connectivity is calculated as the time-wise correlation of blood oxygen level dependent signal (BOLD) of the resting state functional MRI between two brain regions of each participant.

Here, as the regions of interest, we assume Nc regions as mentioned above and, hence, the number of independent non-diagonal elements in the correlation matrix will be Nc×(Nc−1)/2, considering the symmetry.

The regions of interest may be set by the following methods.

Method 1) "Regions of Interest are Defined Based on Anatomical Brain Areas."

Here, for the brain activity biomarker, 140 regions are picked up as regions of interest.

As for ROIs, in addition to 137 ROIs included in the Brain Sulci Atlas (BAL), the cerebellums (left and right) and the vermis of the Automated Anatomical Labeling Atlas are used. The functional connectivity (FC) among these 140 ROIs is used as features.

Here, the Brain Sulci Atlas (BAL) and the Automated Anatomical Labeling Atlas are disclosed in the following References 2 and 3. Disclosures of References 2 and 3 are incorporated herein by reference in their entirety.

Reference 2: Perrot et al., Med Image Anal, 15 (4), 2011
Reference 3: Tzourio-Mazoyer et al, Neuroimage, 15 (1), 2002

Such ROIs include, by way of example, the following:
Dorsomedial Prefrontal Cortex (DMPFC);
Ventromedial Prefrontal Cortex (VMPFC);
Anterior Cingulate Cortex (ACC);
Cerebellar Vermis;
Left Thalamus;
Right Inferior Parietal Lobe;
Right Caudate Nucleus;
Right Middle Occipital Lobe; and
Right Middle Cingulate Cortex.

It is noted, however, that the brain regions used may not be limited to those above. For instance, the regions to be selected may be changed in accordance with the neurological/mental disorder to be studied.

Method 2) "Functional Connectivity is Defined Based on Brain Regions of a Functional Brain Map Covering the Entire Brain."

Here, the brain regions of such a functional brain map are disclosed in the references listed below and, though not limiting, configuration formed of 268 nodes (brain regions) may be adopted. Disclosures of References 4 to 7 below are incorporated herein by reference in their entirety.

Reference 4: Noble S, et al. Multisite reliability of MR-based functional connectivity. Neuroimage 146, 959-970 (2017).
Reference 5: Finn E S, et al. Functional connectome fingerprinting: identifying individuals using patterns of brain connectivity. Nat Neurosci 18, 1664-1671 (2015).
Reference 6: Rosenberg M D, et al. A neuromarker of sustained attention from whole-brain functional connectivity. Nat Neurosci 19, 165-171 (2016).
Reference 7: Shen X, Tokoglu F, Papademetris X, Constable R T. Groupwise whole-brain parcellation from resting-state fMRI data for network node identification. Neuroimage 82, 403-415 (2013).

In the following, description will be made assuming that the method of defining functional connectivity based on the brain regions of the functional brain map in accordance with Method 2) is used. By way of example, there are several candidates for measuring functional connectivity such as the tangent method and the partial correlation method. In the following, however, we use Pearson's correlation coefficient.

For time-lapse of each of possible node sets of pre-processed BOLD signals, Pearson's correlation coefficient after Fisher's z transformation is calculated. The results are used for forming a 268×268 symmetrical connectivity matrix, each element of which represents the strength of connectivity between two nodes. Here, 35,778 ((268×267)/2) values of coupling strength (connectivity) of the lower triangular matrix of the connectivity matrix are used.

Though not specifically limited, calculation of such elements of a correlation matrix may be executed in the following manner.

From the data of brain activities in the resting state, for each subject, Functional Connectivity (FC) among different ROIs is calculated. FC is a feature generally used in analyzing brain activity in the resting state, and it is defined by Pearson's correlation coefficient between different ROI time-sequential signals.

First, time sequence of mean signals of all voxels included in each ROI is extracted.

Though not specifically limiting, the resting-state functional MRI data is subjected to the following pre-processing. The first ten seconds of the data are discarded so as to take into consideration the T1 equilibrium. The pre-processing step includes calibration of slice timing, re-alignment, segmentation of structural image by T1 enhancement, normalization to MNI (Montreal Neurological Institute) space, and spatial smoothing using isotropic Gaussian kernel of 6 mm full-width at half maximum.

As to the analysis of the correlation matrix (connectivity matrix), ROIs are described by a gray matter map having 268 nodes as mentioned above, developed for clustering the most similar voxels. Time-variation of BOLD signals is extracted from these 268 nodes. In order to remove some spurious variations, linear regression is applied, using 36 regression parameters including six kinematic parameters, mean signals of the whole brain, white matter and the cerebral spinal fluid. Differential coefficient and second order term are also included for every parameter.

Bandpass filtering is conducted time-sequentially, using the first order Butterworth filter having pass band between 0.01 Hz and 0.08 Hz, to limit analysis to the changes in low-frequencies.

Residual error sequence after regression is regarded as time-sequential signal values related to functional connectivity, and Pearson's correlation coefficients are calculated between different ROI time sequences.

FIG. 3 shows examples of "measurement parameters" and "subject attribute data."

It is assumed that "subject attribute data" is stored associated with the "patient's MRI measurement data" and the "healthy person's MRI measurement data" in the "patient cohort data" and the "healthy cohort data" of FIG. 1.

As shown in FIG. 3(A), the measurement parameters include site ID for identifying the measurement site, site name, condition ID for identifying the measurement parameters, information related to the measurement device, and information related to the measurement conditions.

The "information related to the measurement device" includes the name of the manufacturer, the model number and the number of (transmitting) receiving coils of the MRI device for measuring brain activities of subjects at each measurement site. The "information related to the measurement device" may include static magnetic field strength, uniformity of magnetic field after shimming and other indexes indicating performance of the measurement device.

The "information related to measurement conditions" includes the direction of phase encoding when an image is re-constructed (P→A or A→P), type of image (T1 weighted, T2 weighted, diffusion weighted etc.), imaging sequence (spin echo etc.), whether the subject's eyes are open/closed during imaging and so on. The "information related to measurement conditions" is not limited to these, either.

Referring to FIG. 3(B), the "subject attribute data" includes the subject's tentative ID as a pseudonym to prevent identification of the subject, condition ID indicating the measurement conditions when the subject was measured, and the attribute information of the subject.

The "subject attribute information" includes sex and age of the subject, a label indicating either healthy or sick, the disease name of the subject as diagnosed by a doctor, medication profile, diagnosis history and so on. The "subject attribute information" may be anonymized as needed at, for example, the measurement site.

By way of example, as to the age and sex, the subject's attribute information may be processed to maintain "k-anonymity" that reduces the probability of identifying an individual to 1/k or smaller by transforming data such that at least k data of "quasi-identifier" (same attribute) exist. Here, "quasi-identifier" refers to an identifier such as "age," "sex," and "place of residence" that cannot identify an individual by itself but allows identification of an individual when combined. Mediation profile and diagnosis history may be subjected to anonymization as needed, by making random or shifting the dates.

In the following, as regards the "patient's MRI measurement data" and the "healthy person's MRI measurement data," the functional connectivity calculated as the correlation of temporal activities between each of the brain areas of each subject will be generally referred to as "functional connectivity" between each brain area. If it is necessary to distinguish one functional connectivity from another, a suffix will be added, as will be described later.

(Configuration of MRI Device)

Figure 4:
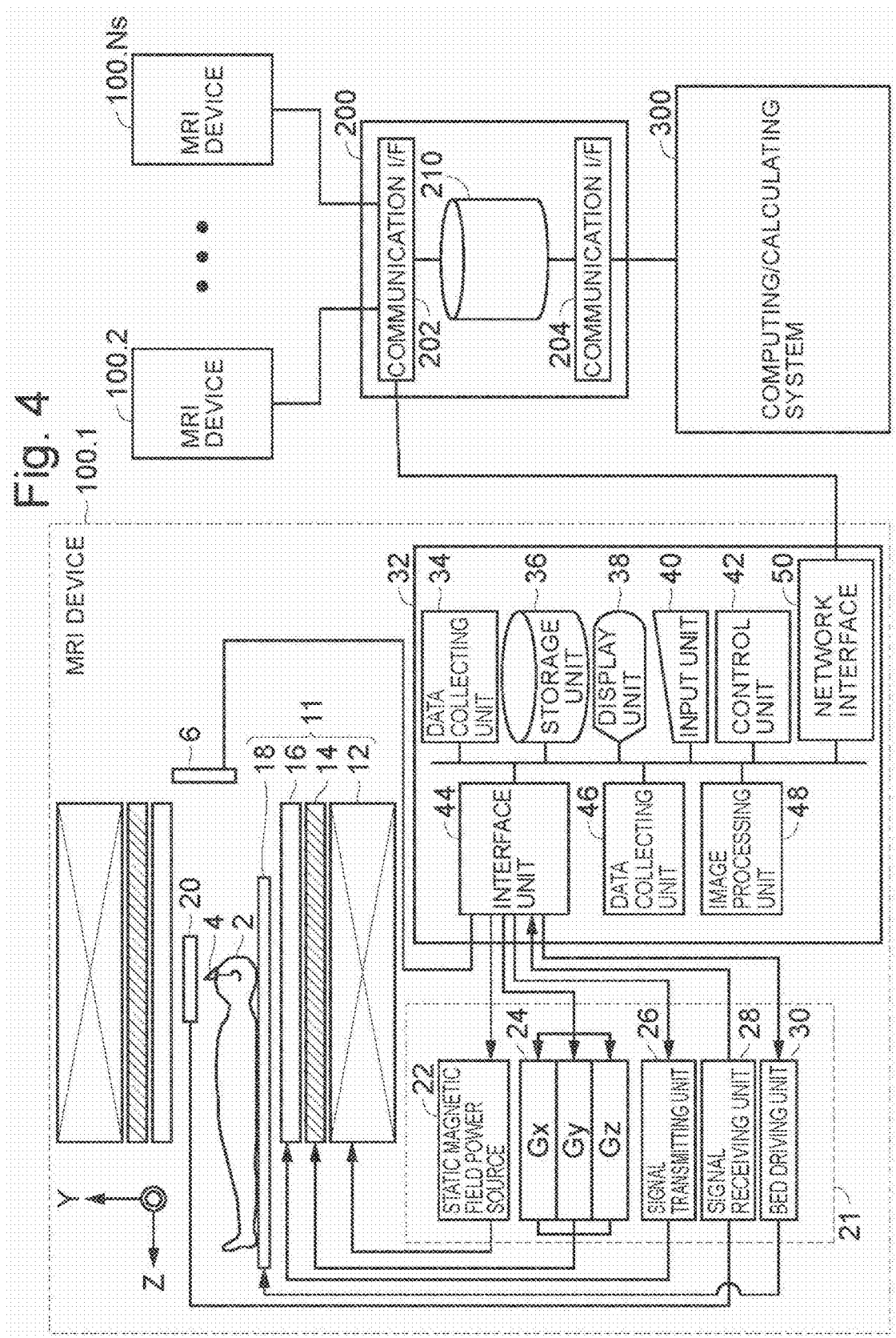
FIG. 4 is a schematic diagram showing an overall configuration of an MRI device $100.i$ ($1 \leq i \leq N_s$) installed at respective measurement sites.

FIG. 4 is a schematic diagram showing an overall configuration of an MRI device 100.$i$ (1≤i≤N$_s$) installed at respective measurement sites. In FIG. 4, MRI device 100.1 at the first measurement site is shown in detail as an example. Other MRI devices 100.2 to 100.N$_s$ also have similar basic configurations.

As shown in FIG. 4, MRI device 100.1 includes: a magnetic field applying mechanism 11 for applying a controlled magnetic field to, and irradiating with RF (Radio Frequency) wave, an ROI of a subject 2; a receiving coil 20 for receiving a response wave (NMR signal) from subject 2 and outputting an analog signal; a driving unit 21 for controlling the magnetic field applied to subject 2 and controlling the transmission/reception of RF wave; and a data processing unit 32 for configuring a control sequence of driving unit 21 and processing various data signals to generate an image.

Here, the central axis of a cylindrical bore in which subject 2 is placed is regarded as a Z-axis, and a horizontal direction orthogonal to the Z-axis and the vertical direction orthogonal to the Z-axis are defined as X-axis and Y-axis, respectively.

In MRI device 100.1 having such a configuration, because of the static magnetic field applied by magnetic field applying mechanism 11, nuclear spins of atomic nuclei forming subject 2 are oriented in the direction of magnetic field (Z-axis) and precess about the direction of magnetic field, with the Larmor frequency unique to the atomic nuclei.

When the subject 2 is irradiated with an RF pulse of the same Larmor frequency, the atoms in subject 2 resonate, absorb energy and are excited, resulting in nuclear magnetic resonance (NMR). When the irradiation with RF pulse is stopped after the resonance, the atoms discharge energy and return to the original, steady state. This process is referred to as a relaxation process. In the relaxation process, the atoms output electromagnetic wave (NMR signal) having the same frequency as the Larmor frequency. The output NMR signal is received by receiving coil 20 as a response wave from subject 2, and the regions of interest of subject 2 are imaged by data processing unit 32.

Magnetic field applying mechanism 11 includes a static magnetic field generating coil 12, a magnetic field gradient generating coil 14, an RF irradiating unit 16, and a bed 18 for placing subject 2 in the bore.

By way of example, subject 2 lies on his/her back on bed 18. Though not limited, subject 2 may view an image displayed on a display 6 mounted perpendicular to the Z-axis, using prism glasses 4. Visual stimulus may be applied to subject 2 by an image on display 6 as needed. Alternatively, visual stimulus to subject 2 may be applied by projecting an image in front of subject 2 using a projector. Such a visual stimulus corresponds to the presentation of feedback information in the above-described neurofeedback.

Driving unit 21 includes a static magnetic field power source 22, a magnetic field gradient power source 24, a signal transmitting unit 26, a signal receiving unit 28, and a bed driving unit 30 for moving bed 18 to any position along the Z-axis.

Data processing unit 32 includes: an input unit 40 for receiving various operations and information input from an operator (not shown); a display unit 38 for displaying various images and various pieces of information related to the regions of interest of subject 2; a storage unit 36 for storing programs, control parameters, image data (structural images and the like) and other electronic data to cause execution of various processes; a control unit 42 for controlling operations of various functional units, including generating a control sequence for driving the driving unit 21; an interface unit 44 for executing transmission/reception of various signals to/from driving unit 21; a data collecting unit 46 for collecting data consisting of a group of NMR signals derived from the regions of interest; an image processing unit 48 for forming an image based on the data of NMR signals; and a network interface 50 for executing communication with a network.

Data processing unit 32 may be a dedicated computer, or it may be a general-purpose computer executing functions causing operations of various functional units, in which designated operations, data processing and generation of control sequence are realized by a program or programs stored in storage unit 36. In the following, description will be given assuming that data processing unit 32 is implemented by a general-purpose computer.

Static magnetic field generating coil 12 causes a current supplied from a static magnetic field power source 22 to flow through a helical coil wound around the Z-axis to generate an induction magnetic field, and thereby generates a static magnetic field in the Z-direction in the bore. The regions of interest of subject 2 are placed in the region of highly uniform static magnetic field formed in the bore. More specifically, here, static magnetic field coil 12 is comprised of four air core coils, forms a uniform magnetic field inside by the combination of the coils, and attains orientation of the spins of prescribed atomic nuclei in the body of subject 2, or more specifically, the spins of hydrogen atomic nuclei.

Magnetic field gradient generating coil 14 is formed of X-, Y- and Z-coils (not shown), and provided on an inner peripheral surface of cylindrical static magnetic field generating coil 12. In order to improve uniformity of magnetic field gradient, a shim coil (not shown) is used and "shimming" is executed.

These X-, Y- and Z-coils superpose magnetic field gradients on the uniform magnetic field in the bore with the X-axis, Y-axis and Z-axis directions switched in turn, whereby creating intensity gradient in the static magnetic field. When excited, the Z-coil tilts the magnetic field intensity to the Z-direction and thereby defines a resonance surface; the Y-coil applies a tilt for a short period of time immediately after application of the magnetic field in the Z-direction, and thereby adds phase modulation in proportion to the Y-coordinate, to the detected signal (phase encoding); and thereafter the X-coil applies a tilt when data is collected, and thereby adds frequency modulation in proportion to the X-coordinate, to the detected signal (frequency encoding).

The switching of superposed magnetic field gradients is realized as different pulse signals are output to the X-, Y- and Z-coils from the magnetic field gradient power source 24 in accordance with a control sequence. Thus, the position of subject 2 expressed by the NMR can be specified, and positional information in three-dimensional coordinates necessary to form an image of subject 2 are provided.

Here, using the orthogonally crossing three sets of magnetic field gradients, allocating slice direction, phase encoding direction and frequency encoding direction to the magnetic fields respectively, as described above, and by combining these, images can be taken from various angles. By way of example, in addition to transverse slice in the same direction as taken by an X-ray CT apparatus, sagittal and coronal slices orthogonal thereto, as well as an oblique slice, of which direction perpendicular to its plane is not parallel to any of the axes of three orthogonally crossing magnetic field gradients, can be imaged.

RF irradiating unit 16 irradiates regions of interest of subject 2 with RF (Radio Frequency) pulses based on a high-frequency signal transmitted from a signal transmitting unit 33 in accordance with a control sequence. Though RF irradiating unit 16 is built in magnetic field applying mechanism 11 in FIG. 1, it may be mounted on bed 18 or integrated with receiving coil 20 as a transmitting/receiving coil 20.

Receiving coil 20 detects a response wave (NMR signal) from subject 2, and in order to detect the NMR signal with high sensitivity, it is arranged close to subject 2. Here, when an electromagnetic wave of NMR signal crosses a coil strand of receiving coil 20, a weak current is generated by electromagnetic induction. The weak current is amplified by signal receiving unit 28 and converted from an analog signal to a digital signal, and then transmitted to data processing unit 32.

As the (transmitting) receiving coil 20, a multi-array coil is used for improving the SN ratio, as described above.

The mechanism here is as follows. To a subject 2 in a state of static magnetic field with Z-axis magnetic field gradient added, a high-frequency electromagnetic field of resonance frequency is applied through RF irradiating unit 16. Prescribed atomic nuclei, for example, hydrogen atomic nuclei, at a portion where magnetic field intensity satisfies the condition of resonance are selectively excited and start resonating. Prescribed atomic nuclei at a portion satisfying the condition of resonance (for example, a slice of prescribed thickness of subject 2) are excited, and (in a classic image drawing) spin axes concurrently start rotation. When the excitation pulse is stopped, electromagnetic waves irradiated by the spin axes in rotation induce a signal in receiving coil 20 and, for some time, this signal is continuously detected. By this signal, a tissue containing the prescribed atoms in the body of subject 2 is monitored. In order to know the position where the signal comes from, X- and Y-magnetic field gradients are added and the signal is detected.

Based on the data built in storage unit 36, image processing unit 48 measures detected signals while repeatedly applying excitation signals, reduces resonance frequency to X-coordinate by a first Fourier transform to obtain an image, restores Y-coordinate by a second Fourier transform, and thus, displays the corresponding image on display unit 38.

For example, by picking-up the BOLD signal on a real-time basis using the MRI system as described above and performing an analysis, which will be described later, on the time-sequentially picked-up images by control unit 42, it is possible to take images of the resting-state functional connection MRI (rs-fcMRI).

In FIG. 4, measurement data, measurement parameters and subject attribute data from MRI device 100.1 as well as from MRI devices 100.2 to 100.$N_s$ at other measurement sites are accumulated and stored in storage device 210 through a communication interface 202 in data center 200. Further, computing system 300 is configured to access data in storage device 210 through communication interface 204.

Figure 5:
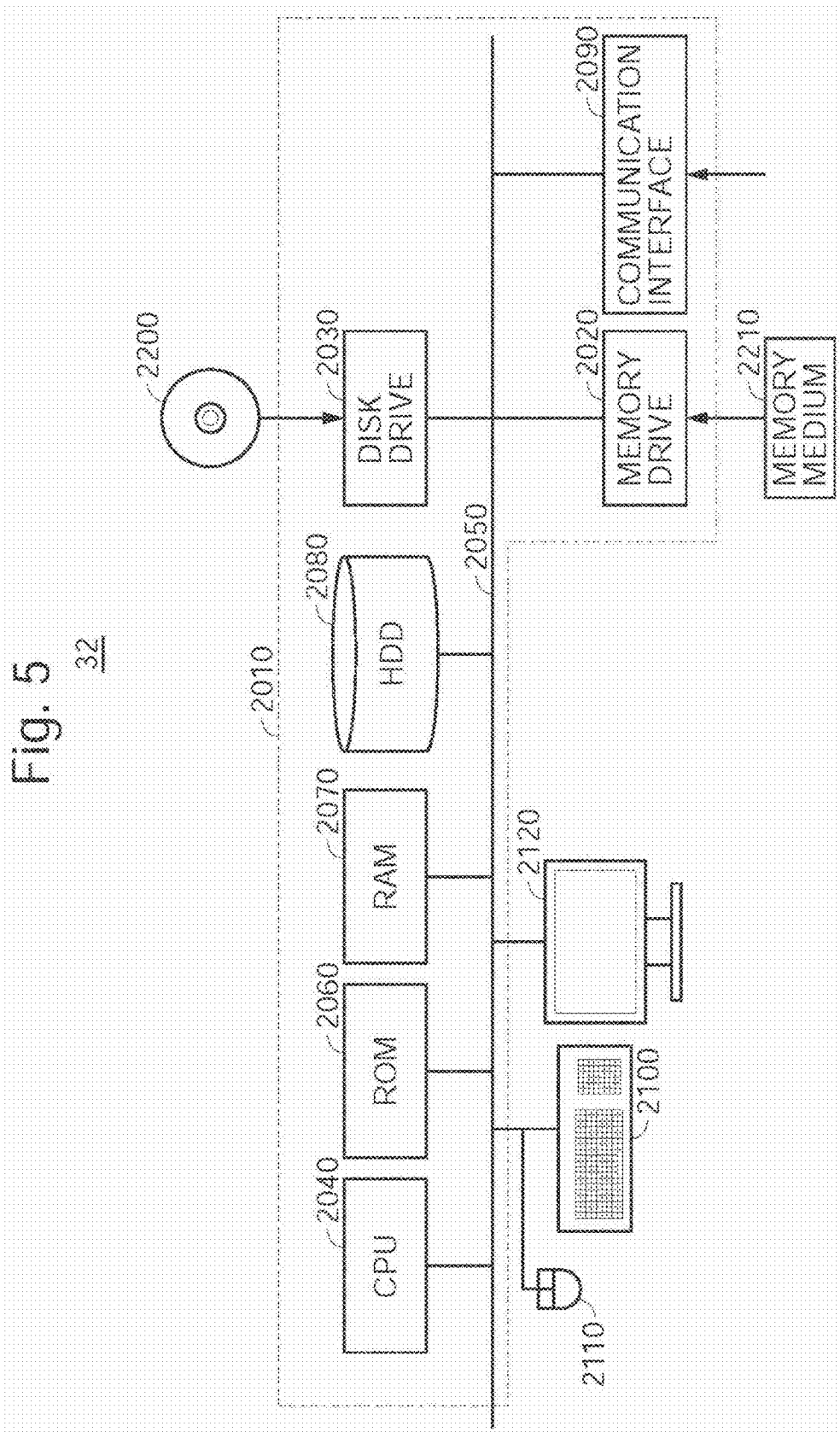
FIG. 5 is a hardware block diagram of a data processing unit 32.

FIG. 5 is a hardware block diagram of data processing unit 32. Though the hardware of data processing unit 32 is not specifically limited as described above, a general-purpose computer may be used.

Referring to FIG. 5, a computer main body 2010 of data processing unit 32 includes, in addition to a memory drive 2020 and a disk drive 2030, a processor (CPU) 2040, a bus 2050 connected to disk drive 2030 and memory drive 2020, an ROM 2060 for storing programs such as a boot-up program, an RAM 2070 for temporarily storing instructions of an application program and providing a temporary memory space, a non-volatile storage device 2080 for storing application programs, system programs and data, and a communication interface 2090. Communication interface 2090 corresponds to an interface unit 44 for transmitting/receiving signals to/from driving unit 21 and the like and a network interface 50 for communicating with another computer through a network, not shown. As non-volatile storage device 2080, a hard disk (HDD), a solid-state drive (SSD) or the like may be used. Non-volatile storage device 2080 corresponds to storage unit 36

By operation processes executed by CPU 2040 in accordance with a program, various functions of data processing unit 32 including, for example, functions of control unit 42, data collecting unit 46 and image processing unit 48 are realized.

A program or programs causing data processing unit 32 to execute the functions of the present embodiment as described above may be stored in a CD-ROM 2200 or a memory medium 2210 and inserted to disk drive 2030 or memory drive 2020 and may be further transferred to non-volatile storage device 2080. The program or programs will be loaded to RAM 2070 when to be executed.

Data processing unit 32 further includes a keyboard 2100 and a mouse 2110 as input devices, and a display 2120 as an output device. Keyboard 2100 and mouse 2110 correspond to input unit 40 and display 2120 corresponds to display unit 38.

The program or programs causing CPU 2040 to function as data processing unit 32 as described above may not necessarily include an operating system (OS) for executing the functions of information processing apparatus such as computer main body 2010. The program or programs may only include those portions of instructions which can call appropriate functions (modules) in a controlled manner to attain a desired result. The manner how data processing unit 32 operates is well known and, therefore, detailed description will not be given here.

Further, the above-described program or programs may be executed by one computer or by a plurality of computers. In other words, both centralized processing and distributed processing are possible. Hardware of computing system 300 has basically the same configuration as that shown in FIG. 5, though there may be some difference such as use of parallel processing units or use of GPGPU (General-Purpose computing on graphic processing units).

(Harmonization of Brain Activity Biomarkers)

When big data related to mental disease is to be collected, it is almost impossible to collect massive brain image data (connectomes related to human disease) at one site. Therefore, it is necessary to collect image data from a plurality of sites.

It is difficult to regulate types of MRI devices (scanners), protocols and patient segments. Therefore, in most cases, when analyzing collected data, brain image data picked up under different conditions are used.

Particularly, disease factor tends to confound site factor and, therefore, when disease factor is to be extracted by applying machine learning to data obtained under different conditions, the site-to-site differences become the highest barrier. One site (or a hospital) tends to sample only a few types of mental diseases (for example, mainly schizophrenia at site A and mainly autism at site B), leading to confounding. In order to regulate data under different conditions appropriately, the harmonization of the site-to-site data is indispensable.

The site-to-site differences essentially include two types of biases. Specifically, technical bias (or measurement bias) and biological bias (or sampling bias).

The measurement bias involves differences in imaging parameters, electric field strength, and the characteristics of MRI scanners such as the MRI manufacturers and the scanner models. The sampling bias relates to differences of subject cohorts from one site to another.

In the following, a method of harmonizing measurement data by evaluating measurement bias independently from sampling bias will be described.

(Harmonization of Traveling Subject Method)

Figure 6:
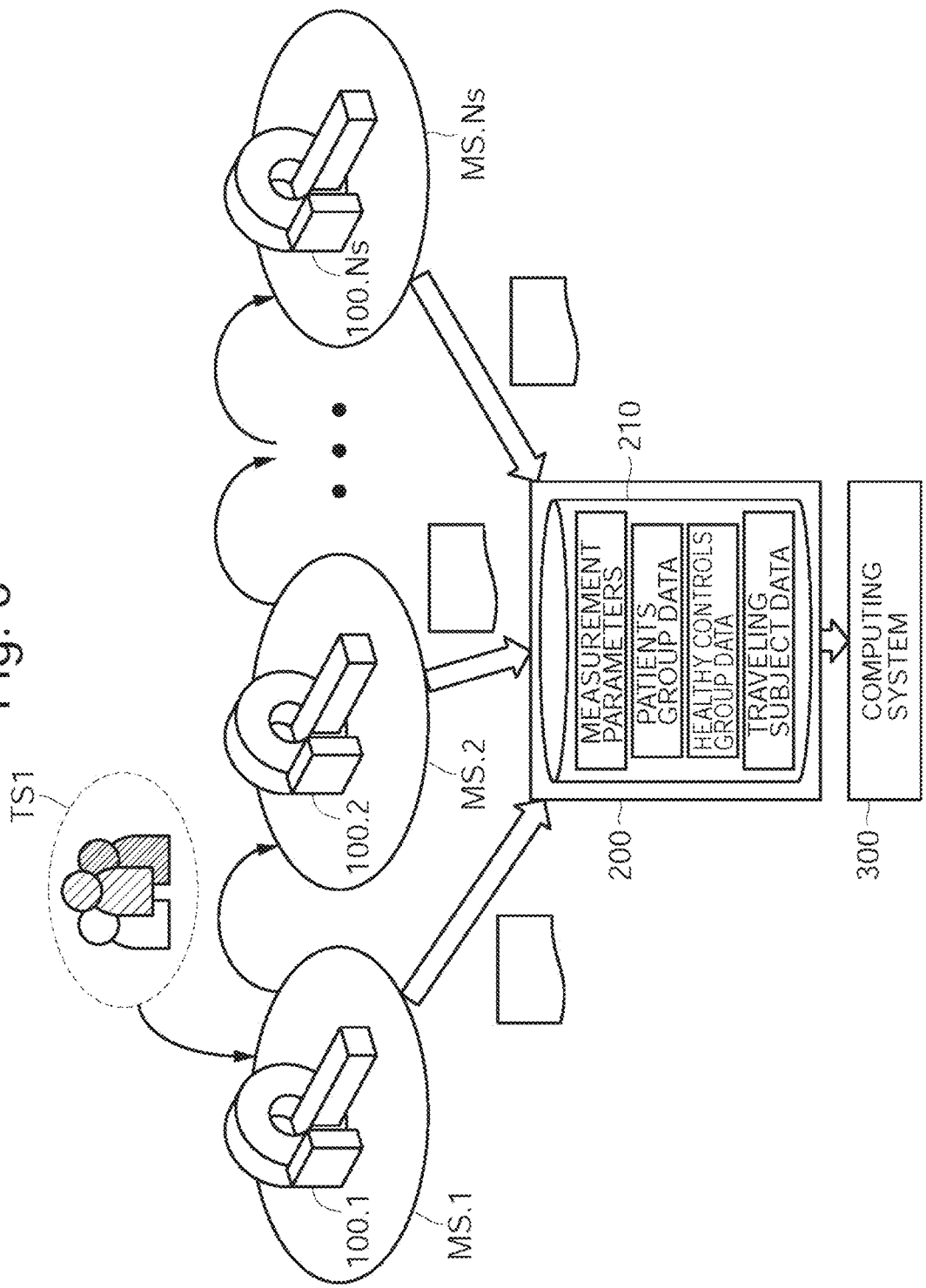
FIG. 6 is an illustration showing a method of evaluating the site-to-site differences of the traveling subjects, who travel to be subjected to measurements at sites by the rs-fcMRI method in accordance with an embodiment.

FIG. 6 is an illustration showing a method of evaluating the site-to-site differences of subjects (hereinafter referred to as traveling subjects), who travel to be subjected to measurements at sites by rs-fcMRI in accordance with an embodiment. As will be described later, in the present embodiment, a harmonization method that can remove only the measurement bias by using the traveling subject dataset will be described.

Referring to FIG. 6, in order to evaluate the measurement bias across measurement sites MS.1 to MS.$N_s$, a dataset of travelling subjects TS1 (number of subjects: $N_{ts}$) is obtained. Assume that the resting state brain activities of $N_{ts}$ healthy participants are imaged at each of the $N_s$ sites, and the $N_s$ sites include all sites where patients' data are imaged. The obtained dataset of the traveling subjects is stored as the traveling subject data in storage device 210 of data center 200. Then, the process for the "harmonization of the brain activity biomarkers" is executed by computing system 300. The traveling subject dataset includes only the healthy cohort. Further, it is assumed that the participants are the same in every site. Therefore, the site-to-site differences in traveling subjects consist only of the "measurement bias."

In the method of harmonization of the present embodiment described in the following, a process of correcting the measurement data at each measurement site by removing the influence of the "measurement bias" as the method of the "harmonization of brain activity biomarkers" is performed.

Specifically, in the following, the "measurement bias" and the "sampling bias" are evaluated using GLMM (Generalized Linear Mixed Model), which is one of the methods of "statistical modeling." Here, typically, GLM (Generalized Linear Model) incorporates the "explanatory variable" explaining the probability distribution of the "response variable." GLM mainly has three components, that is, the "probability distribution," the "link function" and the "linear predictor." By designating how to combine these three components, it is possible to represent various different types of data.

Further, GLMM (Generalized Linear Mixed Model) is a statistical model that allows the incorporation of "individual differences that cannot or is not measured by humans" that cannot be explained by GLM. For example, when objects consist of a number of subsets (for example, subsets taken from different measurement sites), GLMM allows incorporation of the differences in sites in the model. In other words, it is a (mixture) model having a plurality of probability distributions as components.

By way of example, the following reference discloses GLMM. The disclosure of Reference 8 is hereby incorporated by reference in its entirety.

Reference 8: Takuya KUBO, "Data kaiseki no tameno toukei modeling nyu'mon" (Introduction to statistical modeling for data analysis), Iwanami shoten, 1st edition 2012, 14th edition, 2017.

In the statistical model in accordance with the present embodiment described below, typically, what is referred to as "effect" will be described using the terms "bias" and "factor"; "bias" will be used in the terms "measurement bias" and "sampling bias"; and "factor" will be used in other factors (subject factor or disease factor).

Different from a simple flow of GLMM, in the following, factors are analyzed without discriminating a "fixed effect" from a "random effect." The reason for this is that, generally, when GLMM is used, only the variance is estimated for the random effect and the magnitude of effect of each factor will be unknown. Therefore, in order to evaluate the magnitude of each factor's effect, estimation is done with variables transformed as shown below, so that each factor will have a fixed effect average of 0.

i) The measurement bias of each site is defined as a deviation from the average correlated values for the various functional connectivity across all sites.

ii) Sampling biases of healthy people and patients of mental diseases are assumed to be different from each other. Therefore, the sampling bias of each site will be calculated individually for the healthy cohort and patients' cohorts of various diseases.

iii) Disease factor is defined as a deviation from the value of healthy cohort.

Specifically, in the following, Generalized Linear Mixed Model is applied in the following manner to the dataset including patients and to traveling subjects' dataset.

Assume that there are $N_{ts}$ traveling subjects, and of $N_s$ measurement sites, $N_{sh}$ represents the number of sites where the measurement of healthy people was done, and $N_{ds}$ represents the number of sites where the measurement of patients of a certain disease (here, represented by a suffix "dis") was done.

Participant factor (p), measurement bias (m), sampling biases ($S_{hc}$, $S_{dis}$) and mental disease factor (d) are evaluated by fitting a regression model to the correlation values of the functional connectivity of all participants, from the measurement result dataset of patients and the traveling subjects' dataset.

In the following, a vector is denoted by a small letter (for example, m), and it is assumed that every vector is a column vector. A vector element is denoted by a suffix such as mk.

A regression model of a functional connectivity vector (assumed to be a column vector) consisting of n correlation values among brain areas is represented as follows.

$$\text{Connectivity} = x_m^T m + x_{shc}^T s_{hc} + x_{Sdis}^T s_{dis} + x_d^T d + x_p^T p + \text{const} + e$$

$$\sum_i^{N_{ts}} p_j = 0, \quad \sum_k^{N_s} m_k = 0, \quad \sum_k^{N_{sh}} s_{hck} = 0, \quad \sum_k^{N_{sd}} s_{disk} = 0, \quad d_1(HC) = 0$$

In order to represent characteristics of each participant, a binary code system of 1-of-k is used, and every target vector (for example, $x_m$) for a measurement bias m belonging to a site k has elements all equal to zero except for the element k that is equal to 1. If a participant does not belong to any class (healthy people, patient, traveling subject), the target vector will be a vector of which elements are all equal to 0.

Upper suffix T represents transpose of matrix or vector and $X^T$ represents a row vector.

Here, m represents the measurement bias (column vector of $N_s \times 1$), $s_{hc}$ represents the sample vector of healthy cohort (column vector of $N_{sh} \times 1$), $s_{dis}$ represents the sampling bias of a patient (column vector of $N_{sd} \times 1$), d represents the disease factor (column vector of $2 \times 1$, having healthy and disease as elements), p represents the participant factor (column vector of $N_{ts} \times 1$), const represents an average of functional connectivity of all participants (including healthy people, patients and traveling subjects) at all measurement sites, and $e \sim N(0, \gamma^{-1})$ represents noise.

Here, for simplicity of description, only one type of disease is assumed. An example involving a plurality of diseases will be described later.

As to the correlation value of each functional connectivity, the design matrix of the regression model does not have sufficient rank and, therefore, respective parameters are evaluated using the least square regression by L2 normalization. Other than the least square regression by L2 normalization, a different method of evaluation such as Bayesian estimation may be used.

After the above-described regression calculation, b-th connectivity of a subject a can be given as:

$$\text{Connectivity}_{a,b} = x_m^{a^T} m^b + x_{Shc}^{a^T} s_{hc}^b + x_{Sdis}^{a^T} s_{dis}^b + x_d^{a^T} d^b + x_p^{a^T} p^b + \text{const} + e$$

Figure 7:
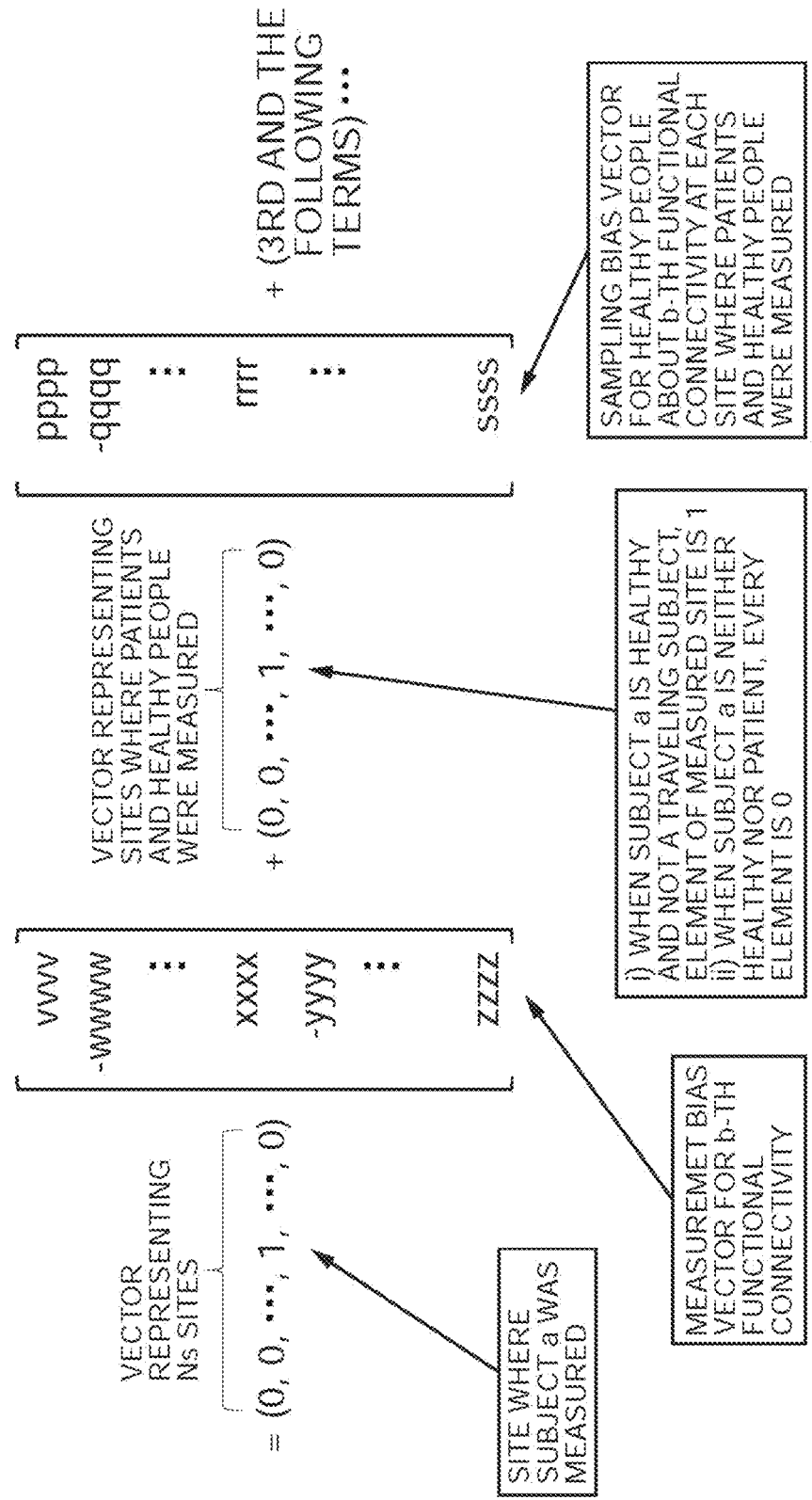

FIG. 7 is an illustration showing how to express b-th functional connectivity of a subject a. FIG. 7 shows the meanings of target vectors of the first and second terms as well as the measurement bias vector and the sampling bias vector of a healthy subject. The same applies to the third and the following terms.

Figure 8:
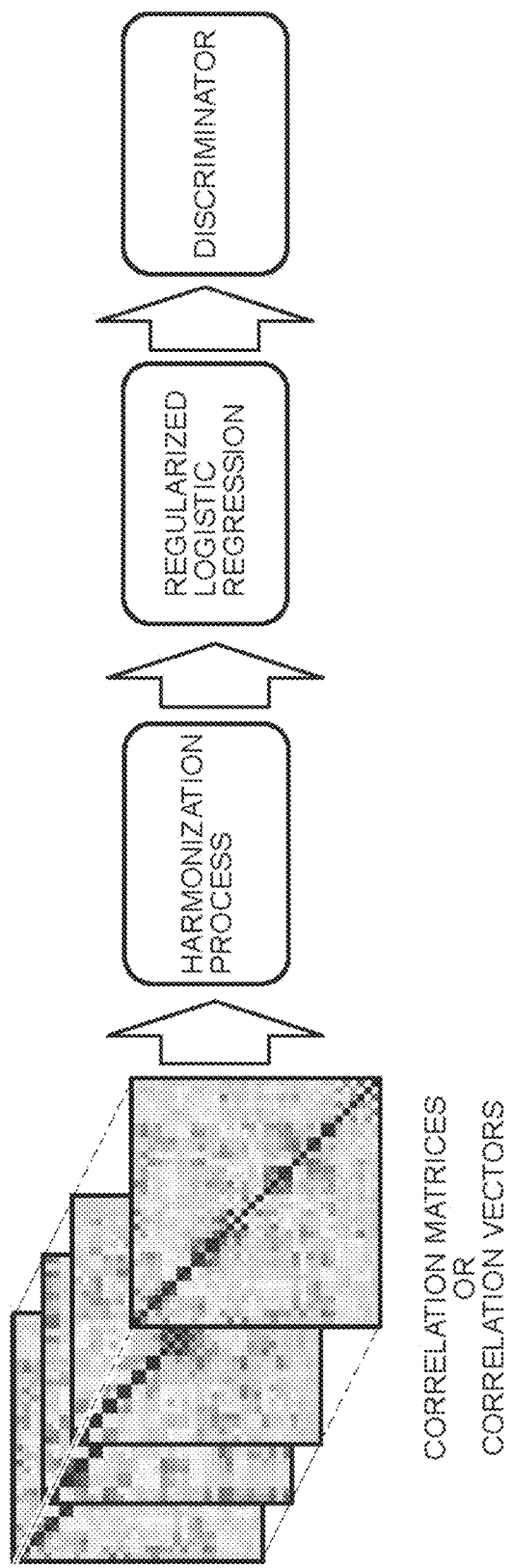
FIG. 8 is an illustration showing a process of generating a discriminator to serve as a biomarker, from correlation matrixes.

FIG. 8 is an illustration showing a process of generating a discriminator to serve as a biomarker, from the correlation matrixes as described with reference to FIG. 2.

As shown in FIG. 5, from the resting state functional connectivity MRI data measured from the healthy cohort and the patients' cohort, the computing system 300 derives the correlation matrix of the degree of activities among the brain regions (regions of interest) for each subject. Thereafter, for the off-diagonal components of the correlation matrix, the corresponding measurement bias is obtained in the manner as will be described later. Then, the measurement bias is subtracted from the values of correlation matrix elements, to realize harmonization. Further, between the element values of correlation matrix after harmonization and the disease label of each subject (the label indicating disease or healthy state), a discrimination model with feature selection while suppressing over-fitting is calculated (by, for example, executing regularized logistic regression), and thereby a discriminator is generated.

Figure 9:
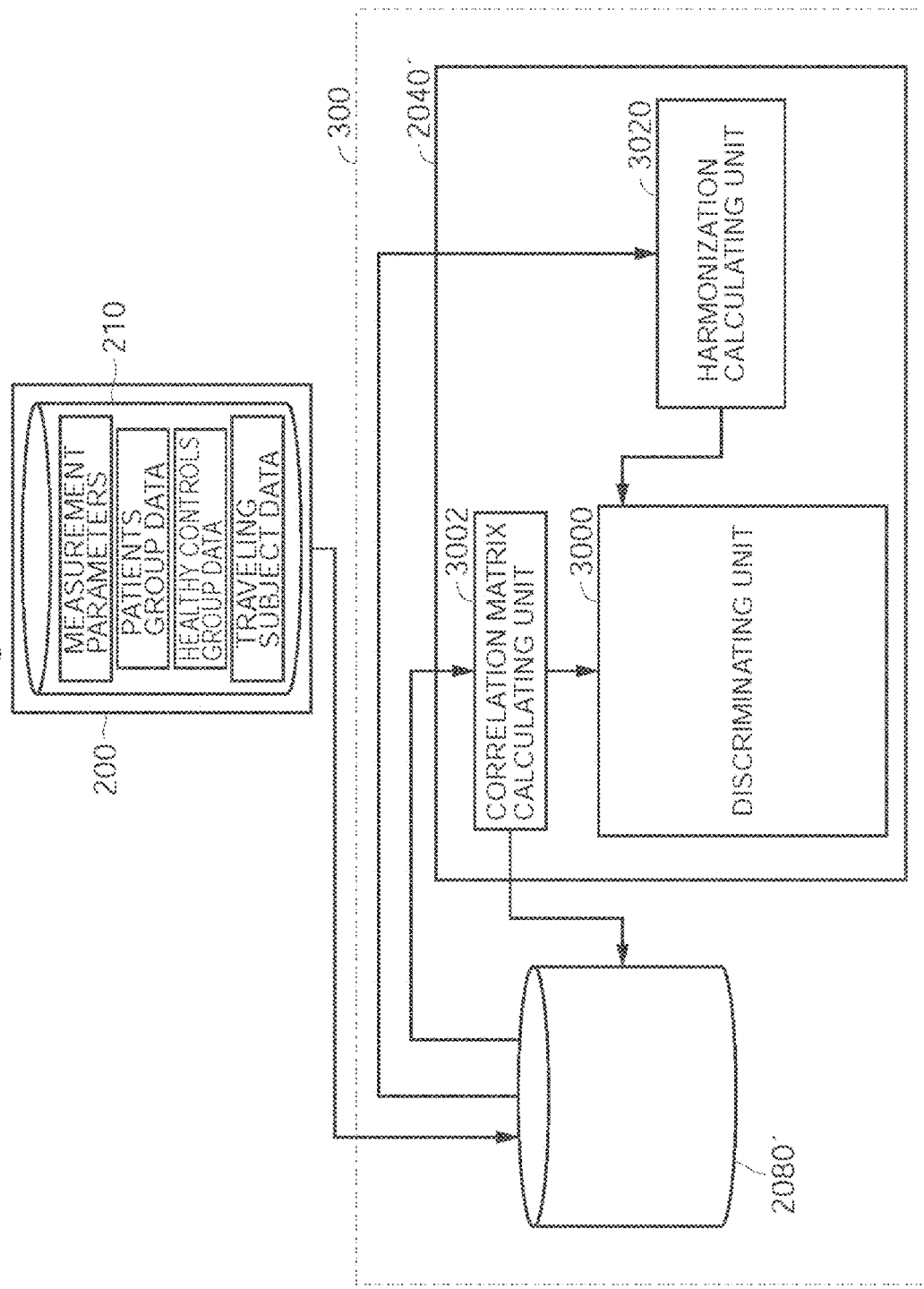
FIG. 9 is a functional block diagram showing the configuration of a computing system 300 executing a harmonization process, a discriminator generating process and a discriminating process.
Figure 10:
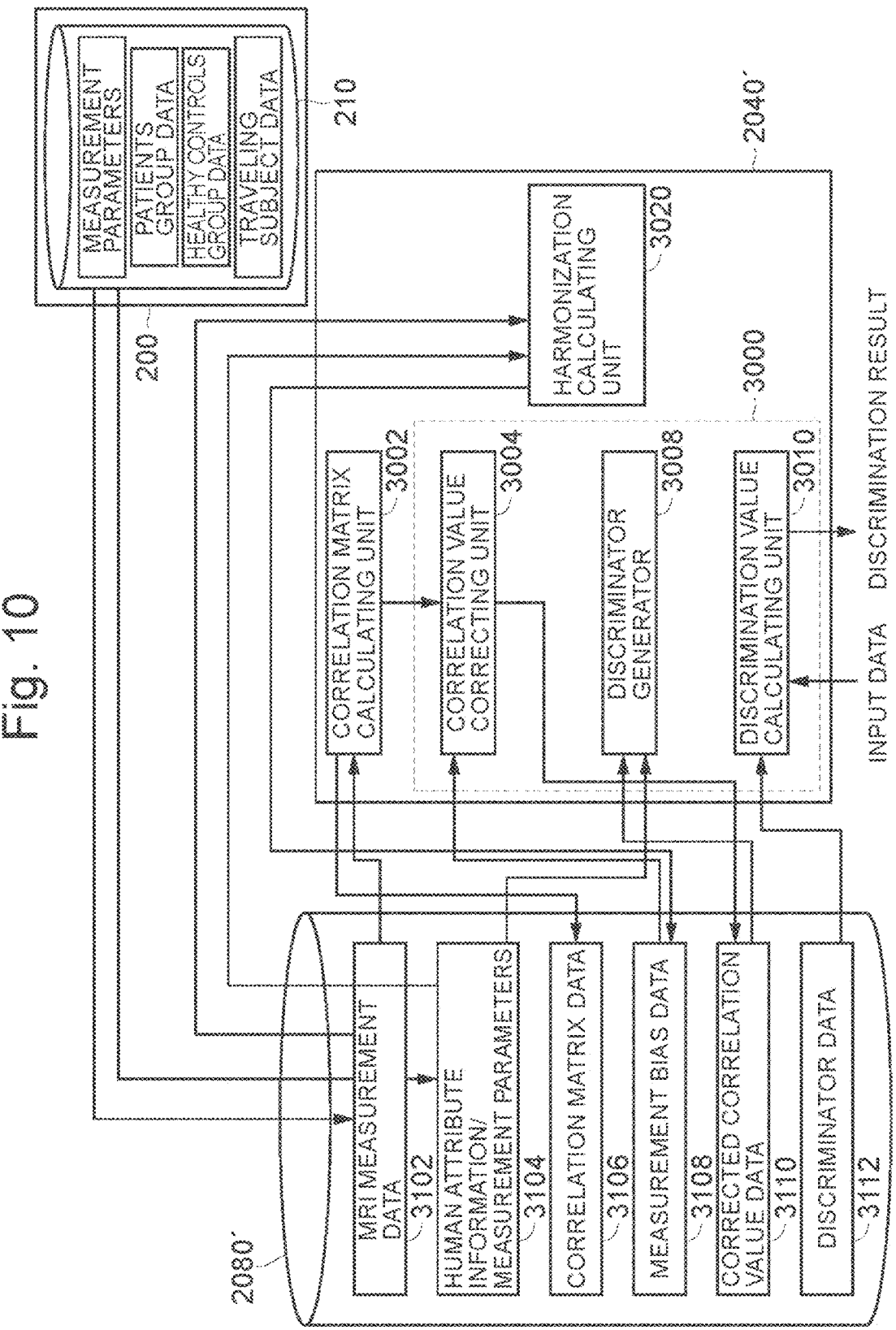
FIG. 10 is a functional block diagram showing more detailed configuration of a computing system 300 executing a harmonization process, a discriminator generating process and a discriminating process.

FIGS. 9 and 10 are functional block diagrams showing configurations of a computing system 300 executing a harmonization process, a discriminator generating process and a discriminating process based on the data stored in storage device 210 of data center 200.

As already described with reference to FIG. 5, computing system 300 has hardware configuration similar to that shown in FIG. 5. Therefore, in the following, hardware parts in the computing system 300 will be denoted by adding a sign (') to the corresponding reference characters in FIG. 5.

Referring to FIG. 9, computing system 300 includes: a storage device 2080' for storing data from storage device 210 as well as data generated during the course of the calculation; and a processor 2040' executing operation on data in storage device 2080'. Processor 2040' may be a CPU.

Processor 2040' includes: a correlation matrix calculating unit 3002 for calculating elements of the correlation matrix for the MRI measurement data 3102 of patients' cohort and healthy cohort by executing a program and storing the results as correlation matrix data 3106 in storage device 2080'; a harmonization calculating unit 3020 for executing the harmonization process; and a discriminating unit 3000 for executing the discriminator generating process and the discriminating process using the generated discriminator, based on the result of harmonization process.

Figure 11:
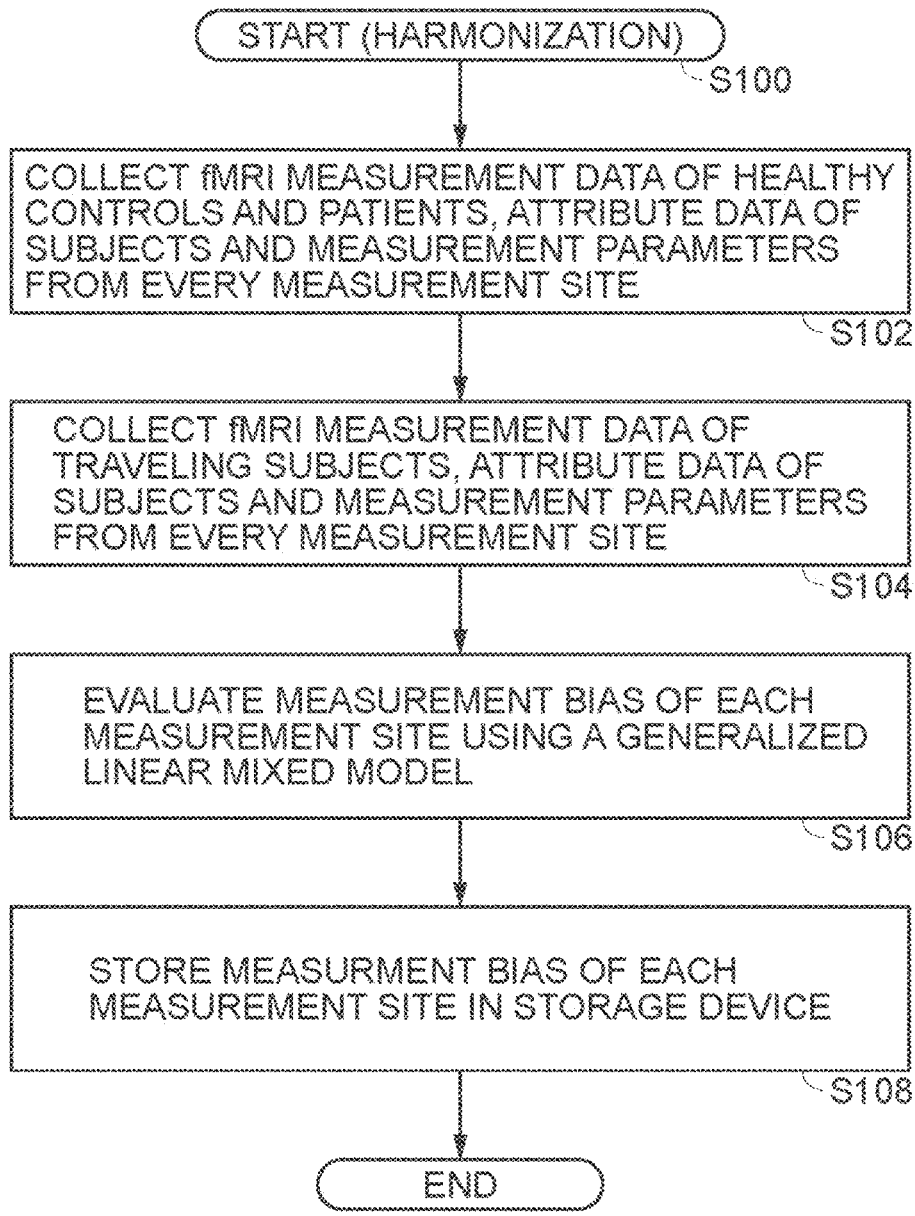
FIG. 11 is a flowchart showing the harmonization process.

FIG. 10 is a functional block diagram showing the configuration of FIG. 9 in greater detail, and FIG. 11 is a flowchart showing the harmonization process. Referring to FIGS. 10 and 11, first, fMRI measurement data of subjects (healthy people and patients), attribute data of subjects and measurement parameters are collected from respective measurement sites to storage device 210 of data center 200 (FIG. 11, S102).

Thereafter, brain activities of traveling subject TS1 are measured while the subject travels from measurement site to site, though not limiting, in a prescribed period (for example, in a one-year period) and the fMRI measurement data of the traveling subject, attribute data of the subject and measurement parameters are collected from respective measurement sites to storage device 210 of data center 200 (FIG. 11, S104).

Using GLMM (Generalized Linear Mixed Model) as described above, the harmonization calculating unit 3020 evaluates the measurement bias of each measurement site with respect to the functional connectivity (FIG. 11, S106).

The harmonization calculating unit 3020 stores the measurement bias of each measurement site calculated in this manner in storage device 2080, as measurement bias data 3108 (FIG. 11, S108).

(Discriminator Generating Process)

Figure 12:
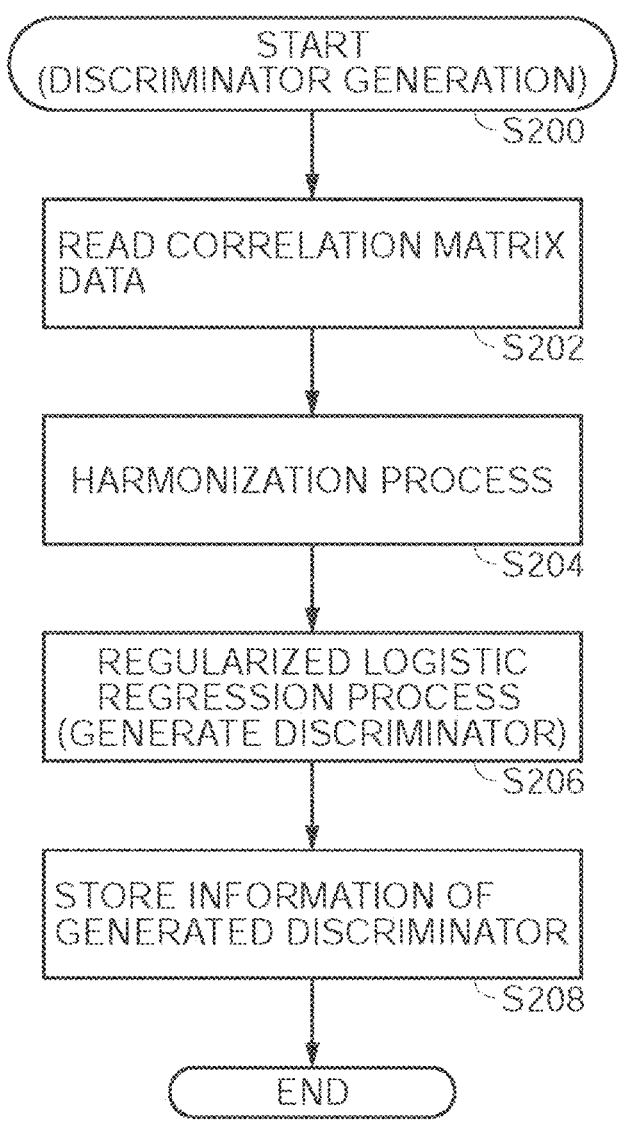
FIG. 12 is a flowchart showing a process of a discriminating unit 3000 for generating a diseased or healthy label discriminator for the subjects.

FIG. 12 is a flowchart showing a process executed by the discriminating unit 3000 shown in FIG. 10 for generating a disease or healthy label discriminator for the subjects. Such a discriminator (or classifier) provides assisting information (support information) for diagnosing a subject.

Referring to FIGS. 10 and 12, a correlation value correcting unit 3004 reads measurement bias data 3108 of each measurement site stored in storage device 2080' (FIG. 12, S202), and for the off-diagonal components of the correlation matrix of each subject as the object of training for machine learning to generate a discriminator, executes the harmonization process in accordance with the equation below.

$$C_{sub} = \text{Connectivity} - x_m^T \hat{m}$$

Here, functional connectivity "Connectivity" represents the functional connectivity before harmonization, and $C_{sub}$ represents the functional connectivity after harmonization. Further, m (hat) (a character with "^" above will be referred to as "hat") represents the measurement bias at a measurement site evaluated by the least square regression by L2 normalization as described above. Thus, the measurement bias corresponding to the measurement site at which functional connectivity has been measured comes to be subtracted from the functional connectivity "Connectivity", and hence, subjected to the harmonization process (FIG. 12, S204). Data after the correction is stored as corrected correlation value data 3110 in storage device 2080'.

As is described in the Reference below, it is assumed that the disease factor relates not to the connectivity of the whole brain but to a specific subset of connectivity. Disclosure of Reference 9 below is incorporated herein by reference in its entirety.

Reference 9: Yahata N, et al. A small number of abnormal brain connections predict adult autism spectrum disorder. Nat Commun 7, 11254 (2016).

Therefore, thereafter, discriminator generator 3008 executes regularized logistic regression for feature selection on the disease label of the subject including the diseased/healthy label of the subject and the corrected functional connectivity, and thus generates a discriminator (FIG. 12, S206).

First, logistic function is used for defining the probability that a participant belongs to a disease class as below.

$$P_{sub}(y_{sub} = 1 \mid c_{sub}; w) = \frac{1}{1 + \exp(-w^T c_{sub})}$$

Here, $y_{sub}$ represents the class label of the participant (y=1 if the diagnosis label is "disease" and y=0 if the diagnosis label is "healthy"), and w represents the weight vector.

As the regularized logistic regression, logistics regression analysis using LASSO (least absolute shrinkage and selection operator) by L1 regularization may be executed, and from 35,778 connections mentioned above, an optimal subset of functional connectivity is selected.

Here, the weight vector w is determined to minimize the following function J.

$$J(w) = -\frac{1}{n_{sub}} \sum_{j=1}^{n_{sub}} \log P_j(y_j = 1 \mid c_j; w) + \lambda \|w\|_1$$

$$\|w\|_1 = \sum_{i=1}^{N} |w_i|$$

Here, $n_{sub}$ is the number of subjects for generating the discriminator, and $\lambda$ represents a hyper parameter used for controlling the amount of shrinkage applied for evaluation.

The method of the executing feature selection and modeling while suppressing over-fitting is not limited to the regularized logistic regression by LASSO, and other methods such as the sparse logistic regression disclosed in the Reference below or the other sparse Bayesian method may be used. Disclosure of Reference 10 below is incorporated herein by reference in its entirety.

Reference 10: Okito Yamashita, Masaaki Sato, Taku Yoshioka, Frank Tong, and Yukiyasu Kamitani. "Sparse Estimation automatically selects voxels relevant for the decoding of fMRI activity patterns." NeuroImage, Vol. 42, No. 4, pp. 1414-1429, 2008.

As described above, a discriminator (that functions as a classifier of the brain activity biomarker) is generated, and discriminator generator 3008 stores information for specifying the discriminator as discriminator data 3112 in storage device 2080' (FIG. 12, S208).

It is noted that the classification performance of the discriminator may be evaluated by cross-validation using the training data.

Though not limiting, the above-described process may be done once in every prescribed period (for example, once a year).

Assume that measurement of functional connectivity is executed for a new subject at any of the measurement sites. It is possible to presume that the measurement bias of this measurement site is constant for a prescribed time period. Therefore, a discrimination value calculating unit 3010 subtracts, from values of the correlation matrix elements of input data of the subject, the "measurement bias" corresponding to the measurement site at which the input data is newly measured, which bias has been already calculated by the above-described procedure, and thus, executes the harmonization process. Then, by the above-described procedure, the "discriminator" that has been already generated through the process steps shown in FIG. 12, outputs a discrimination label for the subject as the discrimination result.

The discrimination result may be a value indicating either one of "diseased" and "healthy," or it may be a value indicating probability of at least one of "diseased" and "healthy."

Regarding the discrimination process executed by the discrimination value calculating unit 3010, the "input data" may be the MRI measurement data themselves representing the brain function activities of the subject, or the data of correlation values as off-diagonal elements of the correlation matrix after the values of the correlation matrix are calculated from the MRI measurement data representing the brain function activities of the subject at each measurement site.

(Harmonization Calculating Process when a New Measurement Site is Added)

Figure 13:
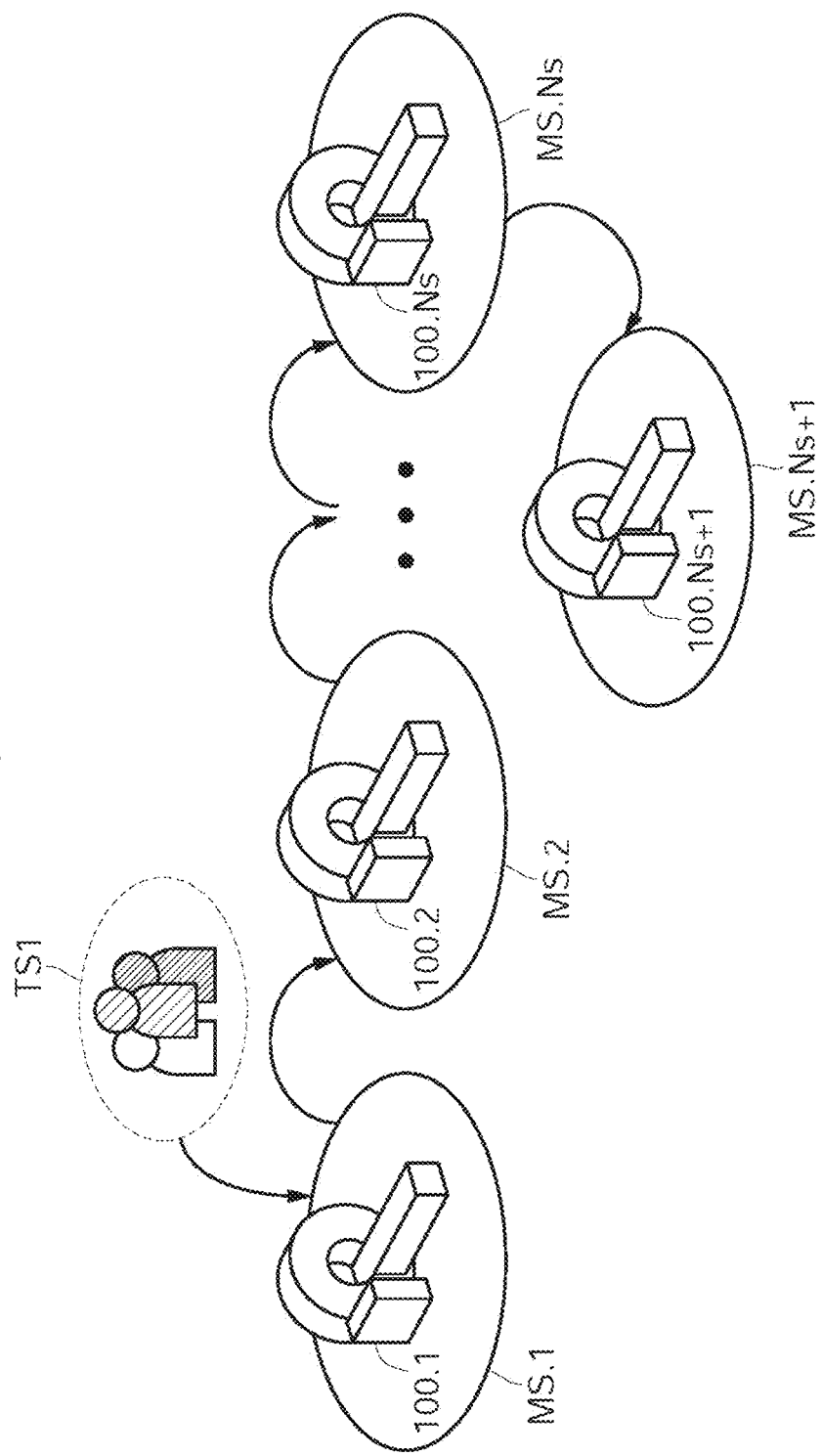
FIG. 13 is a schematic diagram illustrating the harmonization process when a new measurement site is added after execution of a harmonization process.

FIG. 13 is a schematic diagram illustrating the harmonization process when a new measurement site is added after a harmonization process was executed by the procedure described with reference to FIG. 6. Referring to FIG. 13, assume that a ($N_s$+1)-th measurement site MS.$N_s$+1 is newly added. In this case, it is possible to cause the traveling subject or subjects TS1 to newly circulate all of the ($N_s$+1) measurement sites, to perform the same harmonization calculating process described above, and to newly calculate the measurement biases.

By the system that executes the process in accordance with the first embodiment as described above, it is possible to adjust and correct the measurement bias at each facility as regards the brain activity measurement data obtained at a plurality of different facilities. Thus, it becomes possible to adjust the brain functional connectivity correlation values based on the measurement data obtained at a plurality of facilities.

Further, by the system executing the process according to the first embodiment, it is possible to realize a brain activity classifier harmonizing method, a brain activity classifier harmonizing system, a brain activity analyzing system and a brain activity analyzing method, that can harmonize the measurement data of the brain activities measured at a plurality of facilities and thus can provide data for objectively determining healthy or diseased state.

Further, by the system executing the process according to the first embodiment, it is possible to realize a biomarker device based on the brain functional imaging and a program for the biomarker device on neurological/mental diseases, in connection with the measurement data of the brain activities measured at a plurality of facilities.

Modification of the First Embodiment

In the foregoing description, the harmonization calculating process has been described on the premise that the following subject data are obtained.
i) patients' data
ii) healthy people's data
iii) traveling subjects' data If the object is only to evaluate the "measurement bias," however, the "measurement bias" may be evaluated by the GLMM (Generalized Linear Mixed Model), based on the measurement data of the traveling subjects.

Specifically, assume that there are $N_{ts}$ traveling subjects. The participant factor (p) and the measurement bias (m) are evaluated by applying the regression model to the functional connectivity correlation values of all the participants from the traveling subject dataset. Here again, a vector is represented by a small letter (for example m), and it is assumed that every vector is a column vector. A vector element is denoted by a suffix such as mk.

A regression model of a functional connectivity vector (assumed to be a column vector) consisting of n correlation values among the brain areas is represented as follows.

$$\text{Connectivity} = x_m^T m + x_p^T p + \text{const} + e$$

$$\sum_j^{N_{ts}} p_j = 0, \quad \sum_k^{N_s} m_k = 0$$

In order to represent the characteristics of each participant, a binary code system of 1-of-k is used, and every target vector (for example, $x_m$) for a measurement bias m belonging to a site k has elements all equal to zero except for the element k that is equal to 1.

Upper suffix T represents transpose of a matrix or a vector and $X^T$ represents a column vector.

It is possible to calculate the "measurement bias" by the approach above and to execute the harmonization process.

The difference between the method of the first embodiment and the method of the modification of the first embodiment is that when the traveling subjects only are used as in the method of the modification, it becomes unnecessary to take into account the sampling bias. On the other hand, the method of the first embodiment is advantageous in that a larger amount of data used for estimation can be used, as patients' data and healthy people's data are both available. Therefore, improvement in the estimation accuracy of the measurement bias attained by not considering the sampling bias is in a trade-off relation with the improvement in the estimation accuracy of the measurement bias attained by a larger amount of data.

Therefore, though not limiting, it is possible to experimentally optimize the amount of data of participants (patients and healthy people) used at each measurement site in practical operation. In that case, though not limiting, it is possible to allot beforehand the number of participants to be extracted from each measurement site, and at each measurement site, data of the allotted number of participants may be extracted at random.

[Data and Analysis of Actual Results of Brain Activity Measurements]

The following will describe results of the above-described harmonization process actually applied to data of publicly available multi-disease database.

FIG. 14 shows data of multi-disease database and the traveling subject dataset used for the harmonization process. As shown in FIG. 14(a), datasets of patients' cohort and healthy cohort in data publicly available as multi-disease database (https://bicr-resource.atr.jp/decnefpro/) at Strategic Research Program for Brain Science (SRPBS) are used.

The data measured at a plurality of measurement sites (Site 1, Site 2 and Site 3 are representatively shown in FIG. 14) as multi-disease dataset includes, as the site-to-site differences, a sampling bias of patients of mental diseases, a sampling bias of healthy people, and the measurement bias.

On the other hand, as is shown in FIG. 14(b), the data measured at a plurality of measurement sites (Site 1, Site 2 and Site 3 are representatively shown in FIG. 14) as traveling subject dataset includes, as the site-to-site differences, only the measurement bias.

By simultaneous analysis of the datasets, it is possible to divide the site-to-site differences to the measurement bias and the sampling biases, and effect sizes of these on the resting state functional connectivity are quantitatively compared with those of the mental disease.

As to the measurement bias, the effect sizes of different imaging parameters, the manufacturers of MRI devices, and the number of reception coils in the MRI scanners were quantitatively compared. Further, two alternative hypotheses related to the fundamental "sampling bias" of the mechanism were considered.

In the first hypothesis, it is assumed that subjects from a common population are sampled at each site. In this situation, the sampling bias results from random sampling of subjects, that comes from casual difference in characteristics of patients from site to site.

In the second hypothesis, it is assumed that subjects from different subpopulations are sampled at different sites. In this situation, the sampling bias results from sampling from subpopulations having different characteristics.

By way of example, assume that a plurality of sites plans to collect data from the same population of patients having major depressive disorders. Subtypes of major depressive disorders exist in populations such as atypical depression and melancholic depression. Therefore, it is possible that one subpopulation may include many patients of atypical depression while another subpopulation may include many patients of melancholic depression. In actual examples, it may be the case that the appearance frequency of atypical depression patients is higher among patients at site A, while the appearance frequency of melancholic depression patients is higher among patients at site B.

Basic protocol for collecting massive dataset differs between these two hypotheses. Therefore, it is important to determine the hypothesis that most appropriately reflects the characteristics of SRPBS datasets.

According to the former hypothesis, what is necessary is simply to collect data from a larger number of subjects, even from a small number of sites. According to the latter hypothesis, in order to collect truly representative data, it is necessary to obtain data from a plurality of sites.

In order to overcome such limitations related to the site-to-site differences, the harmonization method that can remove only the measurement bias is executed, using the traveling subject dataset.

Based on the resting state functional connectivity MRI data obtained at a plurality of sites and harmonized by the newly proposed method and by an existing method, regression models of subject information (attribute) (for example, age) and mental disease biomarkers were built.

Variation in performance of these prediction models based on the methods of harmonization was studied.

(Datasets Used)

The following three datasets of resting state functional MRI were used.
 (1) Multi-disease dataset of SRPBS
 (2) Dataset of 19 traveling subjects
 (3) Independent validation dataset (Multi-Disease Dataset of SRPBS)

FIG. 15 shows contents of a multi-disease dataset of SRPBS. This dataset includes patients of five different diseases and a group of healthy controls (HCs) diagnosed at nine sites, and contains data of the following 805 participants in total: 482 healthy people from nine sites; 161 patients of major depressive disorders from five sites; 49 patients of autism (ASD) from one site; 65 patients of obsessive-compulsive disorder (OCD) from one site; and 48 patients of schizophrenic disorder (SCZ) from three sites.

FIG. 16 shows imaging protocols at various measurement sites. The resting state functional MRI data were obtained using standardized imaging protocols except for three sites (http://www.cns.atr.jp/rs-fmri-protocol-2/).

The site-to-site differences of this dataset included both the measurement and the sampling biases. For the evaluating biases, only the data obtained by using the standardized protocol was used. The OCD patients were not scanned using the standardized protocol and, hence, the disease factor of OCD was not evaluated.

Reference characters in the table are as follows.
 ATT: Siemens TimTrio Scanner at Advanced Telecommunications Research Institute.
 ATV: Siemens Verio Scanner at Advanced Telecommunications Research Institute.
 KUT: Siemens TimTrio Scanner at Kyoto University
 SWA: Showa University
 HUH: Hiroshima University Hospital
 HKH: Hiroshima Kajikawa Hospital
 COI: COI (Hiroshima University)
 KPM: Kyoto Prefectural University of Medicine
 UTO: University of Tokyo
 ASD: Autism Spectrum Disorder
 MDD: Major Depressive Disorder
 OCD: Obsessive Compulsive Disorder
 SCZ: Schizophrenia
 SIE: Siemens fMRI device
 GE: GE fMRI device
 PHI: Philips fMRI device (Traveling Subjects' Dataset)

In order to evaluate the measurement bias across the measurement sites in the SRPBS dataset, the traveling subjects' dataset was obtained.

Healthy nine participants (all male; age 24-32; average age 27±2.6) were imaged at each of 12 sites, which sites included nine sites that imaged SRPBS datasets, and a total of 411 operation sessions were held.

While we tried to acquire the dataset by using the same imaging protocol as that for multi-disease dataset of SRPBS, due to the limitations of the parameter settings of respective sites or the limitations of conventional scanning conditions, the image protocols differ to some extent from site to site. The differences were, for example, as follows: two directions of phase encoding (P→A and A→P); three different MRI manufacturers (Siemens, GE and Philips); four different numbers of coil channels (8, 12, 24 and 32); and seven scanner types (TimTrio, Verio, Skyra, Spectrum, MR750W, SignaHDxt and Achieva).

Since the same nine participants were imaged at 12 sites, the site-to-site differences of the dataset included only the measurement bias.

(Independent Validation Dataset)

In order to validate the generalizing performance of a model of predicting the participants' age and mental disease classifier based on the resting state functional connectivity MRI data, we obtained data of an independent validation cohort covering two diseases and seven sites. The data was obtained from a total of 625 participants. Specifically, data was obtained from 476 healthy controls (HCs) from six sites, 93 patients of MDD from two sites, and 56 patients of SCZ from one site.

(Visualization of Site-to-Site Differences and Disease Effect)

First, by Principal Component Analysis (PCA), the site-to-site differences and disease effect in the SRPBS multi-disease dataset of the resting state functional connectivity MRI were visualized. FIG. 17 is a graph visualizing the site-to-site differences and the disease effects based on the principal component analysis. Here, the principal component analysis corresponds to the unsupervised dimensionality reduction method.

The functional connectivity of a subject was calculated as the time-wise correlation (using Pearson's correlation coefficient) of the blood oxygen level dependent (BOLD) signal of the resting state MRI between two brain regions, for each participant.

Functional connectivity is defined based on a functional brain map consisting of 268 nodes (or brain regions) covering the entire brain.

Of a matrix representing the correlation of functional connectivity, 35,778 (that is, (268×267)/2) the values of connection strength (connectivity) of the lower triangular matrix are used.

As shown in FIG. 17, the participants' data in the SRPBS multi-disease dataset were all plotted on two axes consisting of the first two principal components. Specifically, all participants of the SRPBS multi-disease dataset are projected on the first two principal components (PC) as represented by small, light-colored markers. The average of all healthy controls at each site and the average of each mental disease are represented by dark-colored markers. The marker colors represent the sites and the different shapes of markers represent different mental diseases.

The principal component 1 was separated by the HUH site so clearly that almost all the data variance could be explained. Patients of ASD were scanned only at the SWA site. Therefore, the patients of ASD (▲) and healthy controls HCs (●) scanned at this site were plotted almost on the same position. FIG. 17 shows the dimensional reduction by the PCA in the multi-disease dataset.

(Bias Evaluation)

In order to quantitatively study the site-to-site differences of the resting state functional connectivity MRI data, the measurement bias, the sampling bias and the diagnosis factor were specified. As described above, the measurement bias of each site was defined as a deviation from an average across all sites of the correlation values for each functional connectivity. It is assumed that the sampling bias of healthy people differs from that of patients of mental disease. Therefore, the sampling bias of each site was calculated individually for the group of healthy controls and the group of patients of each disease.

The disease factor was defined as a deviation from the value of the healthy control group. From the reason that the patient cohorts were sampled at a plurality of sites, the sampling bias was evaluated based on the patients of MDD and SCZ. Since patients of OCD were not scanned using the standardized protocol, the disease factor was evaluated for MDD, SCZ and ASC. Two types of biases vary simultaneously site to site and, therefore, it is difficult to divide the site-to-site differences to the sampling and measurement biases using only the SRPBS multi-disease dataset.

In contrast, the traveling subjects' dataset involved only the measurement bias, since participants were fixed.

By combining the traveling subjects with the SRPBS multi-disease dataset, the sampling and measurement biases were evaluated simultaneously, as different factors influenced by different sites. In order to evaluate the effect of disease factor and both types of biases on the functional connectivity, the "Linear Mixed-Effects Model" was used as described in the following.

(Linear Mixed-Effects Model on SRPBS Multi-Disease Dataset)

In the linear mixed-effects model, the correlation value of connectivity of each subject in the SRPBS multi-disease dataset consists of a fixed effect and a random effect. The fixed effect includes the average correlation value over all participants and across all sites as the base line, and a sum of the measurement bias, the sampling bias and the disease factor. The effect as a combination of the participant's factor (individual difference) and the scan-to-scan variation is regarded as the random effect.

(Details of Bias and Factor Evaluation)

The participant factor (p), the measurement bias (m), the sampling biases (shy, $s_{mdd}$, $s_{scz}$) and the mental disease factor (d) were evaluated by fitting a regression model to the correlation values of functional connectivity of all participants from the SRPBS multi-disease dataset and the traveling subjects' dataset.

In the following, a vector is denoted by a small letter (for example, m), and it is assumed that every vector is a column vector. A vector element is denoted by a suffix such as mk.

As described above, in order to represent the characteristics of each participant, a binary code system of 1-of-k is used, and every target vector (for example, $x_m$) for a measurement bias m belonging to a site k has elements all equal to zero except for the element k that is equal to 1. If a participant does not belong to any class, the target vector will be a vector with all elements equal to zero.

Upper suffix T represents transpose of matrix or vector and $X^T$ represents a row vector.

For each connectivity, the regression model can be represented as

Connectivity=

$$x_m^T m + x_{Shc}^T s_{hc} + x_{Smdd}^T s_{mdd} + x_{Sscz}^T s_{scz} + x_d^T d + x_p^T p + \text{const} + e$$

$$\sum_j^9 p_j = 0, \quad \sum_k^{12} m_k = 0, \quad \sum_k^6 s_{hck} = 0, \quad \sum_k^3 s_{mddk} = 0,$$

$$\sum_k^3 s_{sczk} = 0, \quad d_1(HC) = 0$$

Here, m represents the measurement bias (12 sites×one), $s_{hc}$ represents the sample vector of healthy cohort (six sites×one), $s_{mdd}$ represents the sampling bias of MDD patients (three sites×one), $s_{scz}$ represents the sampling bias of SCZ patients (three sites×one), d represents the disease factor (three diseases×one), p represents the participant factor (nine traveling subjects×one), const represents an average value of the functional connectivity of all participants at all measurement sites, and e~N (0, $\gamma^{-1}$) represents noise. As to the correlation value of each functional connectivity, the respective parameters are evaluated using the least square regression by L2 normalization. Where normalization was not applied, spurious anti-correlation between the measurement bias and the sampling bias for the group of healthy controls, as well as spurious correlation between the sampling bias for the group of healthy controls and the sampling bias for the patients of mental disease were observed. In order to minimize the absolute average value of these spurious correlations, hyper parameter λ adjustment was conducted.

(Linear Mixed-Effects Model on Traveling Subjects' Data Set)

In the linear mixed-effects model on the traveling subjects' dataset, the correlation value of connectivity of each subject for a specific scan in the traveling subjects' dataset consists of a fixed effect and a random effect. The fixed effect includes the average correlation value over all participants and across all sites, and a sum of the participant factor and the measurement bias. Scan-to-scan variation was regarded as a random effect.

For each participant, the participant factor was defined as a deviation of the brain functional connectivity correlation value from the average of all participants.

By fitting the above-described two regression models simultaneously to the functional connectivity correlation values of two different datasets, all biases and factors were evaluated. In this regression analysis, data from the participants scanned using the standardized imaging protocol in the SRPBS multi-disease dataset and the data from all participants of the traveling subjects' dataset were used.

In summary, biases and factors were evaluated as vectors including dimensions reflecting the number of connectivity correlation values (that is, 35,778). Vectors included in this further analysis are as follows: the measurement biases at 12 sites; the sampling biases of HCS at six sites; the sampling biases of MDD patients at three sites; the sampling biases of SCZ patients at three sites; the participant factors of nine traveling subjects; and the diagnosis factors of MDD, SCZ and ASD.

(Analysis of Contribution Size)

In order to quantitatively grasp the relation of magnitude among the factors, contribution sizes were calculated and compared in the linear mixed-effects model to determine which type of bias or factor explains data variance to what extent. After fitting to the model, b-th connectivity of subject a can be represented as:

$$\text{Connectivity}_{a,b} = x_m^{aT} m^b + x_{S_{hc}}^{aT} s_{hc}^b + x_{S_{mdd}}^{aT} s_{mdd}^b + x_{S_{scz}}^{aT} s_{scz}^b + x_d^{aT} d^b + x_p^{aT} p^b + \text{const} + e$$

By way of example, in this model, the contribution size of the measurement bias (the first term) was calculated as follows.

$$\text{Contribution } size_m = \frac{1}{N_m} \frac{1}{N_s \times N} \sum_{a=1}^{N_s} \sum_{b=1}^{N} \frac{(x_m^{aT} m^b)^2}{(x_m^{aT} m^b)^2 + (x_m^{aT} s_{hc}^b)^2 + \left(x_{S_{mdd}}^{aT} s_{mdd}^b\right)^2 + (x_{S_{scz}}^{aT} s_{scz}^b)^2 + (x_d^{aT} d^b)^2 + (x_p^{aT} p^b)^2 + e^2}$$

Here, Nm represents the number of elements of each factor, N represents the number of connectivity, $N_s$ represents the number of subjects, and Contribution $size_m$ represents the magnitude of the contribution size of the measurement bias.

These equations were used for evaluating the contribution size of individual factor related to the measurement bias (for example, phase encoding direction, scanner, coil and fMRI manufacturer). Particularly, the measurement bias was broken down to these factors and thereafter, related parameter was evaluated. Other parameters were fixed to values evaluated before.

Findings from the contribution size evaluation are as follows.

1) The effect size of the measurement bias to the functional connectivity is shown to be smaller than the participant factor but larger than most of the disease factors, suggesting that the measurement bias could be a significant limitation in the research related to mental diseases.
2) The largest variance of the sampling bias is significantly larger than the variance of the MDD factor, and the smallest variance of the sampling bias was ½ of the variance of the disease factor. This also suggests that the measurement bias could be a significant limitation in the research related to mental diseases.
3) Standard deviation of the participant factor was about twice the standard deviation of the disease factors of SCZ, MDD and ASD. Therefore, individual fluctuation in the population of healthy people was larger than among the patients of SCZ, MDD and ASD, when all functional connectivity is considered.
4) Further, in most cases, the standard deviation of the measurement bias was larger than the standard deviation of disease factors, while the standard deviation of the sampling bias was comparable to the standard deviation of the disease factors. Such a relation makes it very difficult to develop a classifier based on the resting state functional connectivity MRI directed to mental diseases or developmental difficulty. Generation of a classifier that is robust and allows generalization over a plurality of sites becomes possible only when an abnormal functional connectivity specific to a small number of very rare diseases or independent of measurement site can be selected from a large number of connections.

(Hierarchical Clustering Analysis for Measurement Bias)

Figure 18:
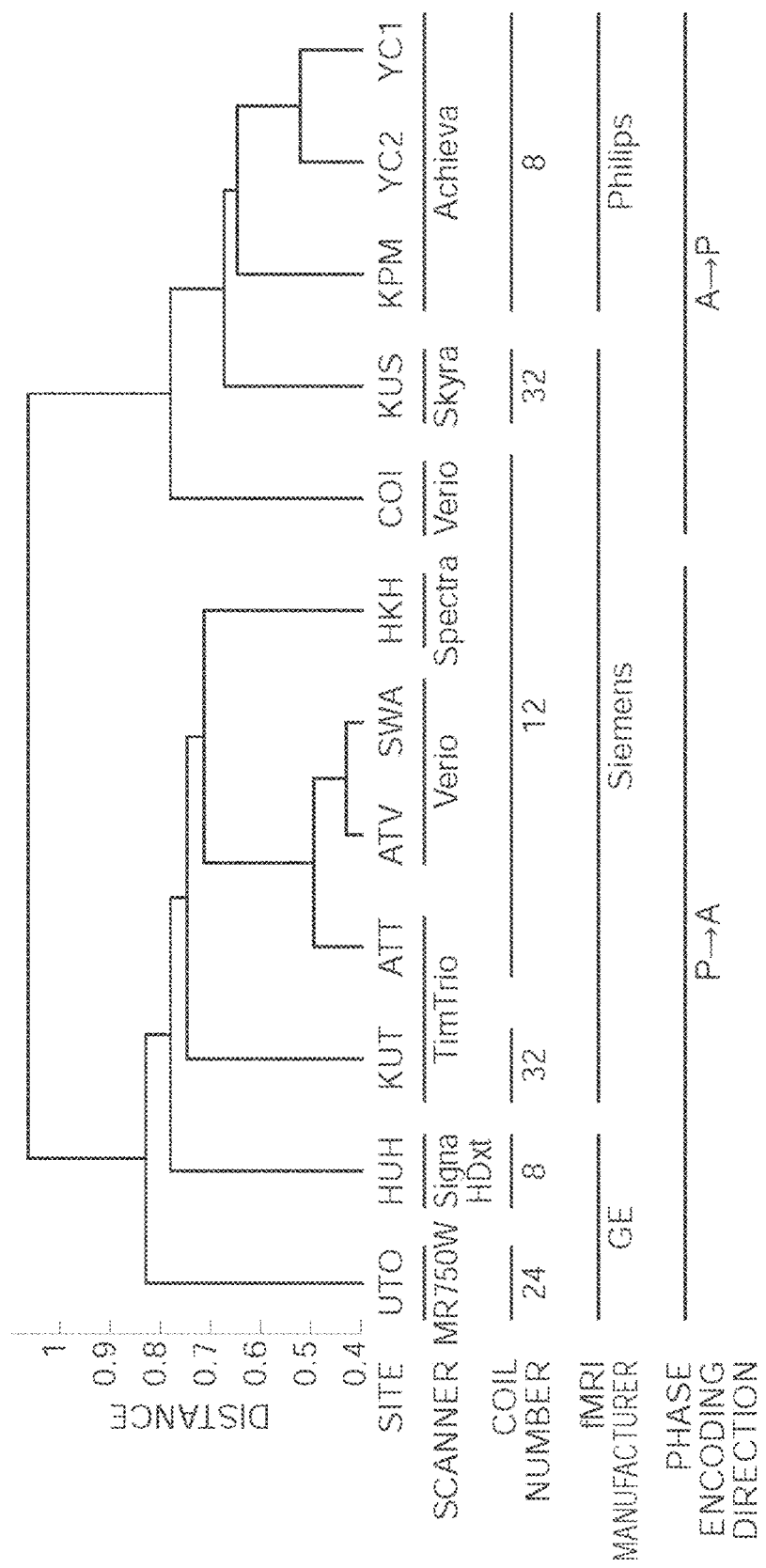
FIG. 18 is a tree diagram based on a hierarchical clustering analysis.

For each site k, Pearson's correlation coefficients among measurement biases mk (N×1, here N is the number of functional connectivity) were calculated and hierarchical clustering analysis was conducted based on the correlation coefficients across the measurement biases. FIG. 18 is a tree diagram derived from the hierarchical clustering analysis. The height of each linkage in the tree diagram represents dissimilarity (1−r) between the clusters coupled by that link.

While studying the characteristics of measurement biases, we examined whether or not the similarity of the measurement bias vectors evaluated for 12 sites reflected specific characteristics of the MRI scanners such as the direction of the phase encoding, the MRI manufacturer, the coil type and the scanner type.

In order to find clusters having the same pattern on the measurement biases, we used the hierarchical cluster analysis. As a result, as is shown in FIG. 18, measurement biases at 12 sites were divided by phase encoding directions to clusters at the first level. At the second level, the measurement biases were divided to clusters by the fMRI manufacturers, and then further divided to coil type clusters and further to scanner model clusters.

Figure 19:
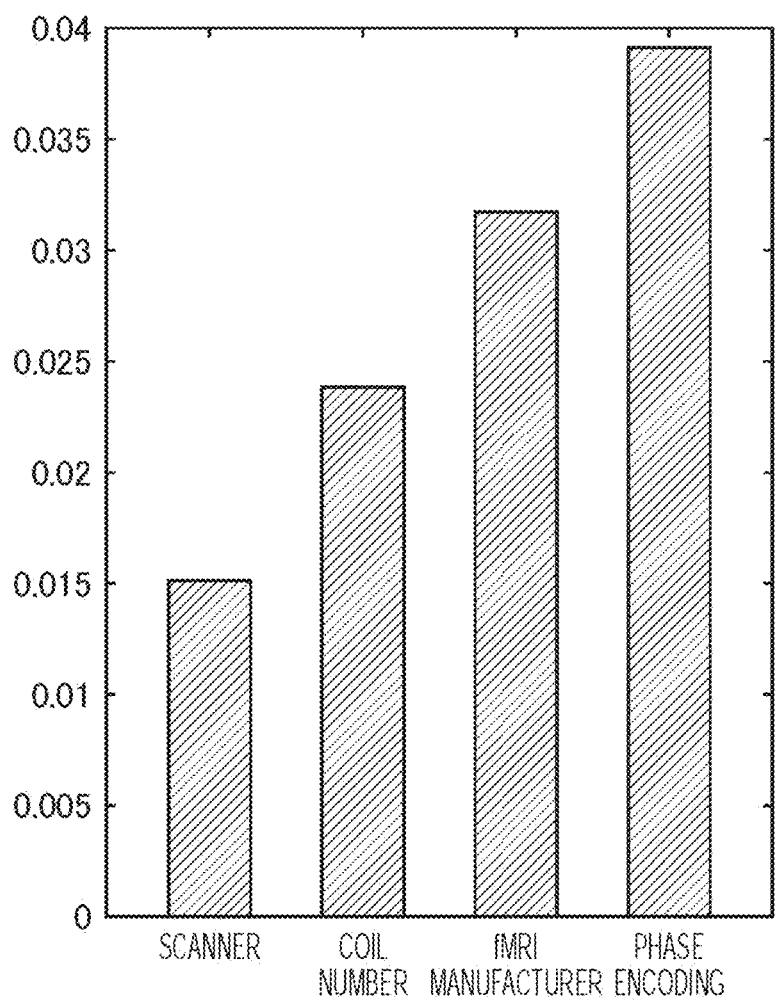
FIG. 19 shows the contribution size of each factor.

FIG. 19 shows the contribution size of each factor. As shown in FIG. 19, in order to evaluate the contribution of each factor, the magnitude relation of the factors was quantitatively confirmed by using the same model.

The contribution size was the largest for the phase encoding direction (0.0391), followed by the fMRI manufacturer (0.0318), the coil type (0.0239) and the scanner model (0.0152). From these results, it can be seen that the main factor having influence on measurement biases is the phase encoding direction, followed by the differences in the fMRI manufacturer, the coil type and the scanner model.

(Sampling Bias Resulting from Sampling from Subpopulation)

Figure 20:
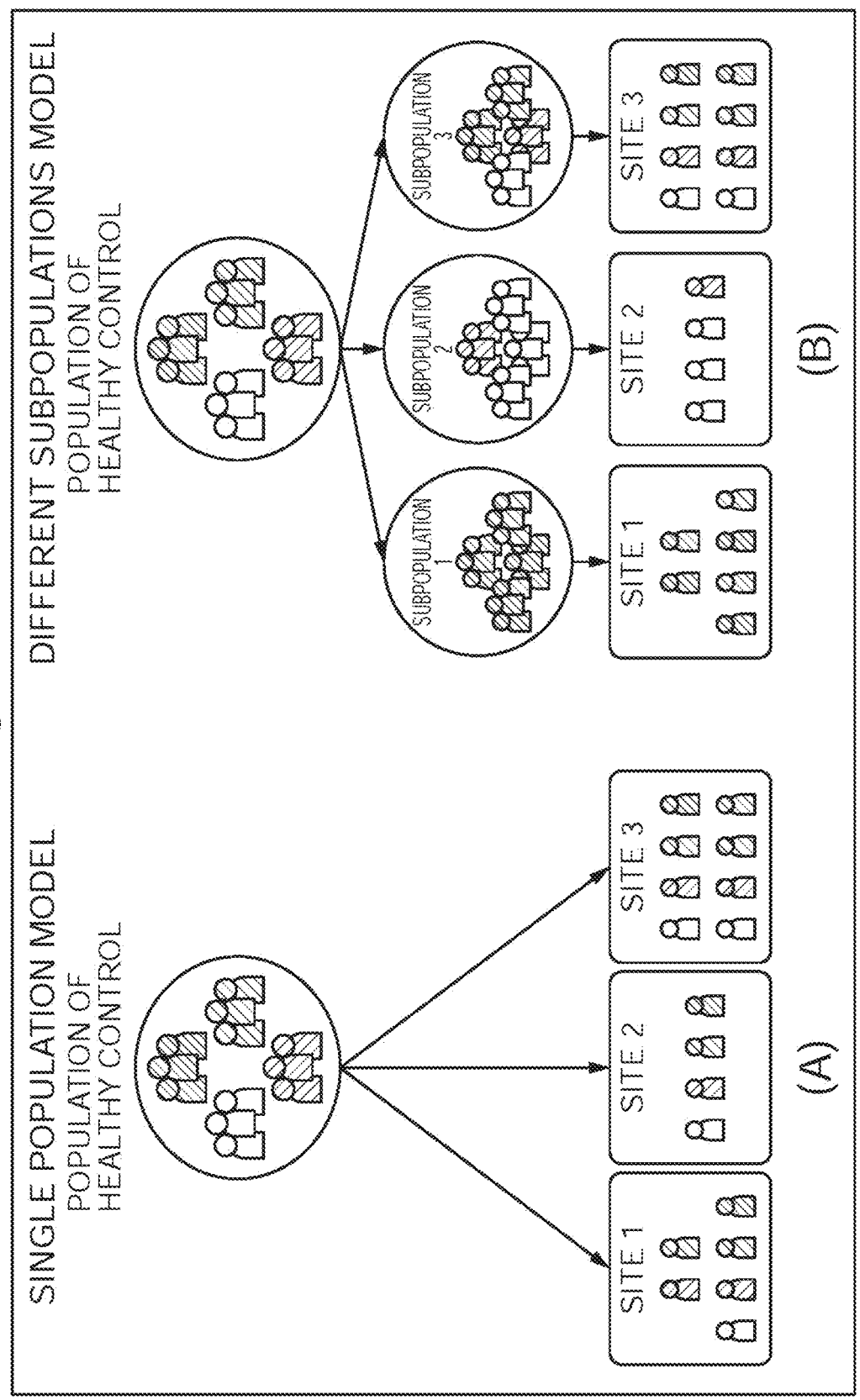
FIG. 20 is a schematic diagram illustrating a mechanism as a background of "sampling bias."

Two alternative models of the mechanism as a background of the "sampling bias" as described above were examined. FIG. 20 is a schematic diagram illustrating a mechanism as a background of the "sampling bias."

In a "single population model" of FIG. 20 (A), it is assumed that participants are sampled from a common population. The correlation values of the functional connectivity of each participant are generated from Gaussian distribution.

In a "different subpopulations model" of FIG. 20 (B), it is assumed that sampling biases are generated partially because participants are sampled from different subpopulations at each site. An average of subpopulation differs site to site and is generated from Gaussian distribution. Further, correlation values of functional connectivity of each participant are generated from Gaussian distribution based on the average of subpopulation at each site.

It is necessary to determine which model is better for collecting big data across a plurality of sites. If the former model is better, it means that the obtained data can be used for representing the population by increasing the number of participants, even if the number of the sites is small. On the other hand, if the latter model is correct, one site cannot be said to represent a true entire population distribution even if the sample size is quite large and, therefore, data should be collected from many sites.

For each model, how the number of participants at each site determines the effect on sampling biases of the functional connectivity was first examined. Based on the variance on the sampling biases across the functional connectivity, magnitudes of effect were measured. Though there is no essential difference based on which value is used, we used variance rather than standard deviation, in order to simplify statistical analysis.

It was theoretically shown that respective models represent different relations between variance of sampling biases and the number of participants. Therefore, by comparing corrected Akaike's Information Criterion (AICc) with Bayesian Information Criterion (BIC), we examined which model represents the actual relation of the data. Further, using all but one site for generating models, we conducted leave-one-site-out cross validation on prediction performance of predicting variance of sampling biases of the remaining site by the models. Then, prediction performances of the two models were compared.

The results show that for the data, the model based on different subpopulations matches better than the model based on a single population (Model based on different subpopulations: AICc=−108.80 and BIC=−113.22; Model based on a single population: AICc=−96.71 and BIC=−97.92). Further, the prediction performance of the model based on different subpopulations was significantly higher than the model based on a single population (Wilcoxon signed rank test applied to absolute error was: p=0.0469, sign rank=19, n=6).

These results show that sampling biases were caused by not only random sampling from a single, large population but also sampling from different subpopulations. Thus, it is shown that the sampling bias poses a major limitation when truly single distribution of patients' data or healthy control cohort is to be evaluated based on measurements obtained from a finite number of sites and participants.

(Visualization of Harmonization Effect)

Next, we will describe the method of harmonization that allows the removal of the measurement bias only, using the traveling subjects' dataset.

As described above, using the Linear Mixed-Effects Model, measurement biases were evaluated separately from the sampling biases. By this method, it is possible to remove measurement biases only from the SRPBS multi-disease dataset, and to maintain sampling biases containing biological information.

(Harmonization of Traveling Subjects)

The phase encoding direction at the HKH site was different between the SRPBS multi-disease dataset and the traveling subject dataset. Therefore, in order to evaluate measurement biases, in the following, separate from the measurement biases, a phase encode factor ($pa_q$) was introduced in the Equation below. The measurement biases and the phase encode factor were evaluated by applying the regression model to the SRPBS multi-disease dataset and the traveling subject dataset coupled together.

The regression model is as follows:

Connectivity =

$$x_m^T m + x_{Shc}^T s_{hc} + x_{Smdd}^T s_{mdd} + x_{Sscz}^T s_{scz} + x_d^T d + x_p^T p + x_{pa}^T pa + \text{const} + e$$

$$\sum_j^9 p_j = 0, \sum_k^{12} m_k = 0, \sum_k^6 s_{hck} = 0, \sum_k^3 s_{mddk} = 0,$$

$$\sum_k^3 s_{sczk} = 0, d_1(HC) = 0, \sum_q^2 pa_q = 0$$

Here, "pa" represents the phase encode factor (two phase encoding directions×1).

The correlation value of each functional connectivity was subjected to normalization by the least square regression by normal LS normalization, whereby each parameter was evaluated. The site-to-site differences were removed by subtracting the evaluated the site-to-site differences and the phase encode factor.

Therefore, the correlation value of the functional connectivity with the sampling bias harmonized is represented as:

$$\text{Connectivity}^{sampling} = \text{Connectivity} - x_m^T \hat{m} - x_{pa}^T \widehat{pa}$$

Here, "m" represents the evaluated measurement bias, and "pa" (hat) represents the evaluated phase encode factor.

Figure 21:
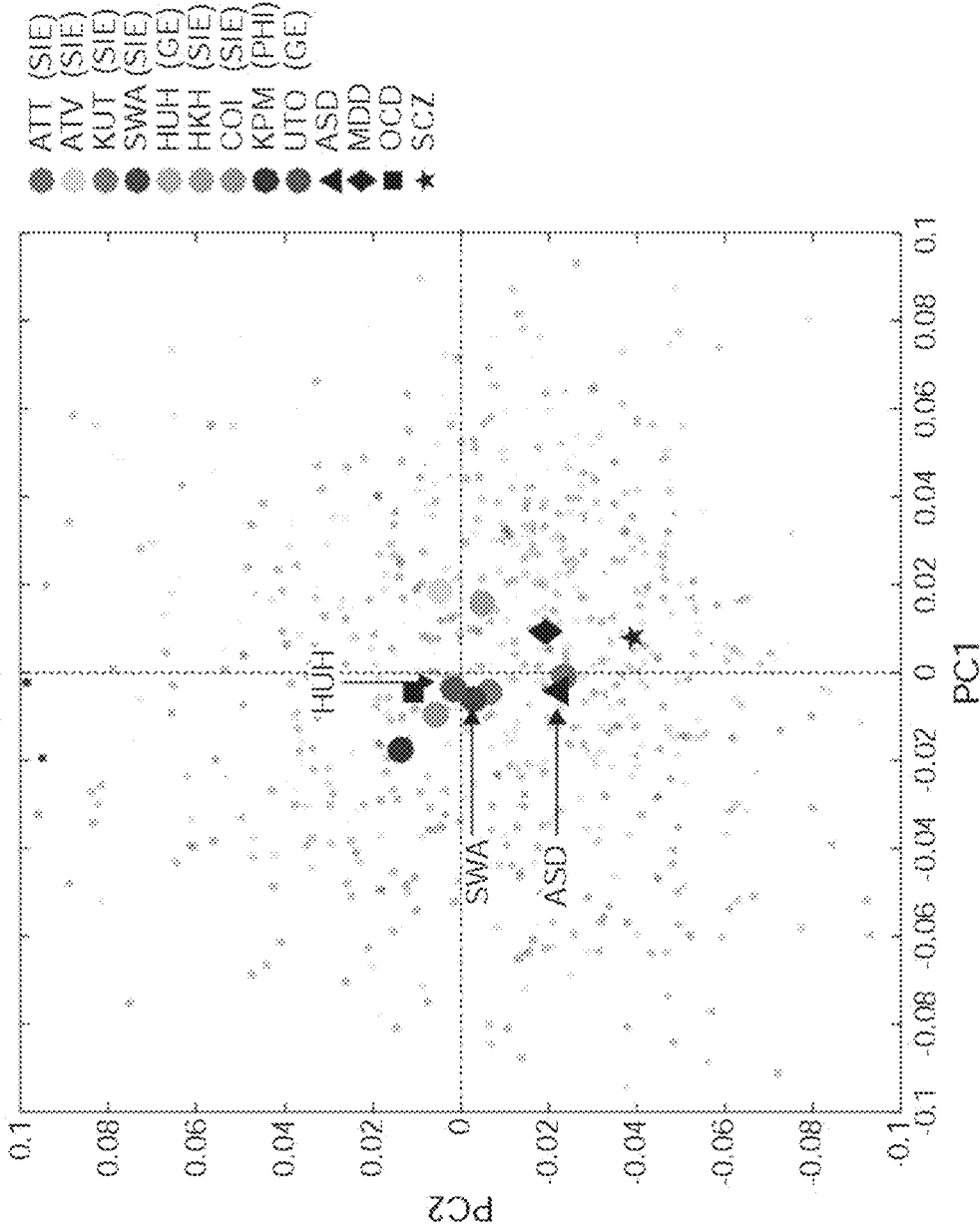
FIG. 21 visualizes the influence of the harmonization process, to be compared with FIG. 17.

FIG. 21 visualizes influence of the harmonization process, to be compared with FIG. 17. In FIG. 21, from the SRPBS multi-disease dataset, only the measurement biases were removed, and thereafter, the data was plotted. FIG. 17 reflects data before harmonization. When compared with FIG. 17, in FIG. 21, the HUH site is considerably moved to be closer to the origin (that is, to the average of population), and it is not very far from other sites.

The results shown in FIG. 21 indicate that separation of HUH site such as shown in FIG. 17 is caused by the measurement biases, which can be removed by the harmonization.

Further, the harmonization was also effective to identify patients from healthy control scanned at the same site. Patients of ASD were scanned only at the SWA site and, therefore, the average of ASD patients (▲) and average of healthy people (○) are plotted almost on the same positions in FIG. 17. These two symbols, however, are clearly separated from each other in FIG. 21. This means that in the first two PCs without harmonization, it was impossible to observe the influence of mental disease (ASD) and that by removing the measurement biases, it becomes detectable.

(Classifier for MDD and SCZ)

In order to quantitatively evaluate the harmonization methods, for the purpose of identifying healthy controls and patients based on the resting state functional connectivity MRI data, a mental disease biomarker was built using the SRPBS multi-disease dataset, and the following four different harmonization methods for removing the site-to-site differences from the SRPBS multi-disease dataset were compared.

(1) Using the Linear Mixed-Effects Model, by combining the traveling subjects' dataset (that is, the traveling subject method) and the SRPBS multi-disease dataset, the measurement biases were evaluated separately from the sampling biases.

(2) Using the batch effect correction tool generally used in the field of genomics, utilizing the ComBat method, the site-to-site differences were modeled and removed. The ComBat method is disclosed, by way of example, in the reference below. The disclosure of Reference 11 is incorporated herein by reference in its entirety.

Reference 11: Johnson W E, Li C, Rabinovic A, "Adjusting batch effects in microarray expression data using empirical Bayes methods." Biostatistics 8, 118-127 (2007).

(3) Using the Generalized Linear Model (GLM), the measurement biases were evaluated without adjusting biological covariate (such as diagnosis or age), using only the SRPBS multi-disease dataset (specifically, in accordance with the GLM method). The GLM method is disclosed, for example, in the reference below. The disclosure of Reference 12 is incorporated herein by reference in its entirety.

Reference 12: Fortin J P, et al. Harmonization of cortical thickness measurements across scanners and sites. Neuroimage 167, 104-120 (2017).

(4) Using the GLM method, the measurement biases were evaluated by adjusting biological covariate of the SRPBS multi-disease dataset only (specifically, in accordance with the adjusted GLM method). This method is also disclosed in Reference 12 above.

Further, these four methods were compared with the non-harmonization method (in which raw data was used).

The object was to focus on the multi-site data, and data from patients having MDD and SCZ sampled from a plurality of sites were used as targets. In order to build various classifiers, machine learning technique was applied to the following two cases.

(1) All functional connectivity data related to the healthy controls and related to the MDD patients from the SRPBS multi-disease dataset (135 patients of MDD from five sites, 425 healthy controls from nine sites).

(2) All functional connectivity data related to the healthy controls and related to the SCZ patients from the SRPBS multi-disease dataset (44 patients of SCZ from three sites, 425 healthy controls from nine sites).

As described above, by performing logistic regression analysis using the LASSO method for feature selection, the optimal subset of functional connections was selected from 35,778 connections.

Figure 22:
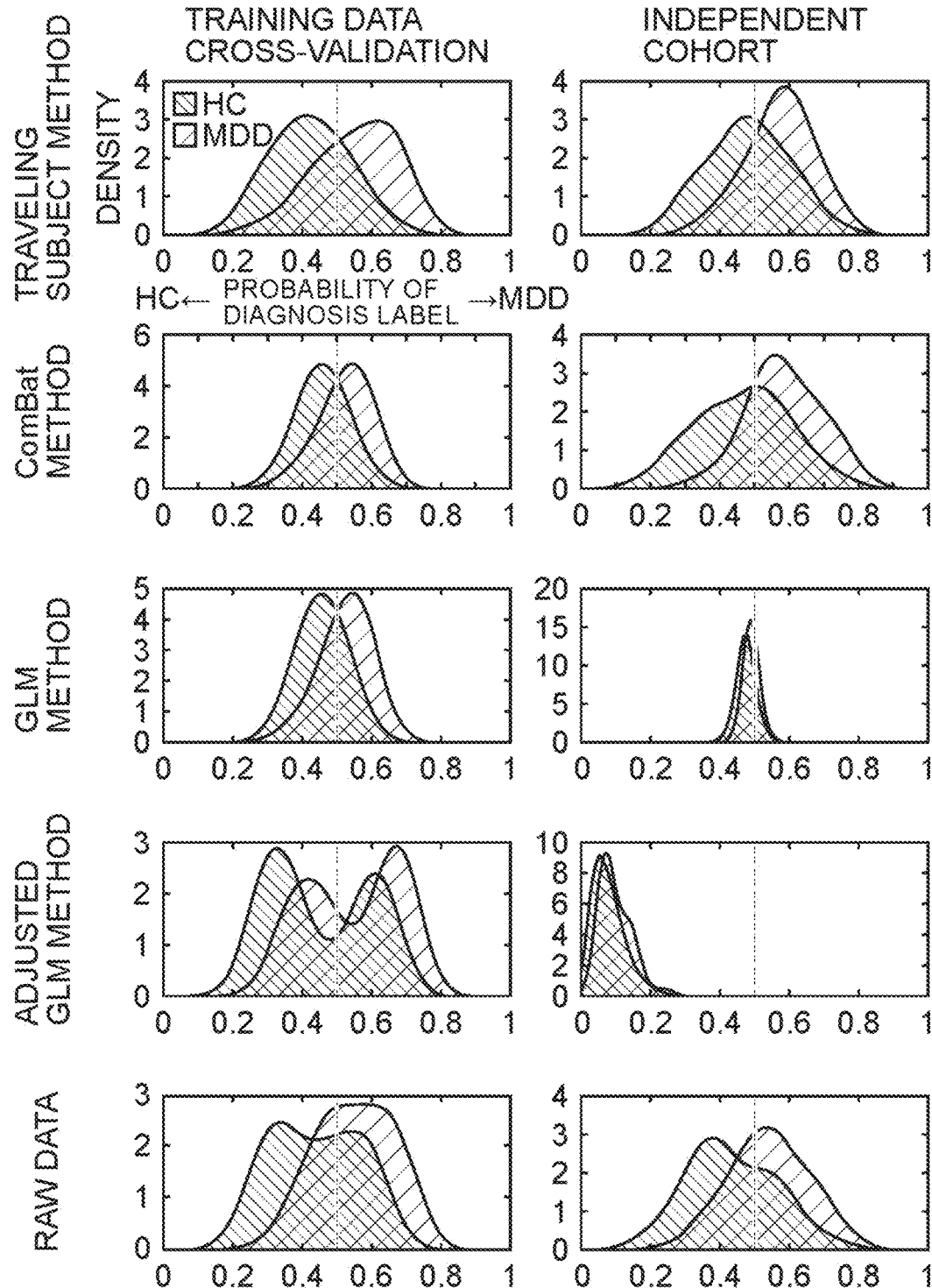
FIG. 22 shows classification performances of classifiers with respect to MDD.
Figure 23:
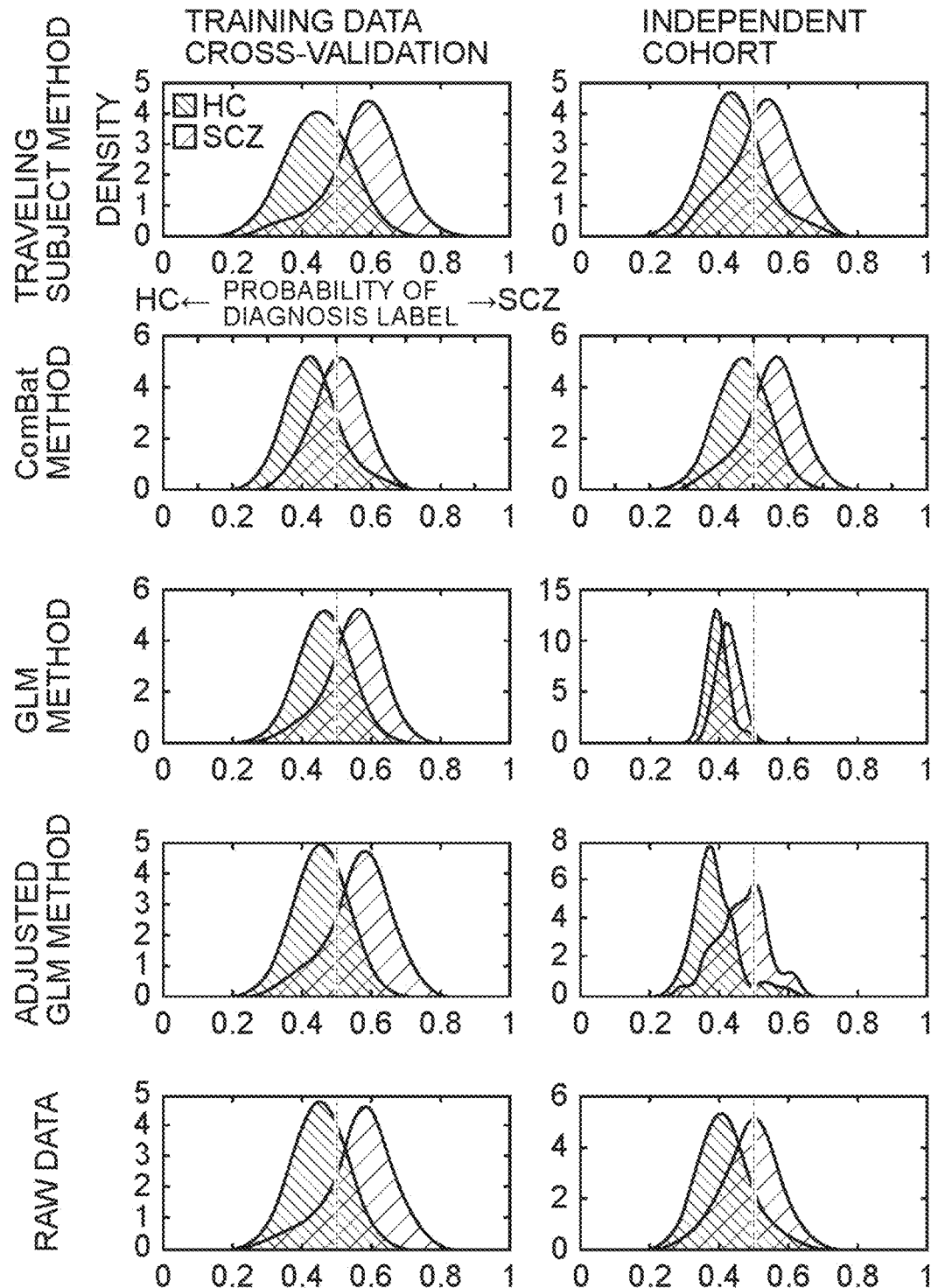
FIG. 23 shows classification performances of classifiers with respect to SCZ.

The generalization capability of the model was tested by partially using the dataset of fully independent validation cohort. FIG. 22 shows the classification performances of classifiers with respect to MDD. FIG. 23 shows the classification performances of classifiers with respect to SCZ.

In order to ensure that data of every participant is used during training of the classifiers, the procedure of generating the classifiers was repeated 100 times (that is, re-sampled). This makes it possible to determine that the average of classifier performance indicates the classifier performance of the training dataset.

In FIGS. 22 and 23, that the probability of a diagnosis label indicating a disease exceeds 0.5 provides information (supporting information) assisting the diagnosis that the object has a mental disease.

As shown in the left columns of FIGS. 22 and 23, the probability distribution of diagnosis supporting information in the training dataset clearly separates, at the threshold value of 0.5, patients of mental disease from the healthy people (the central line in each graph).

In contrast, as shown in the right columns of FIGS. 22 and 23, the probability distribution of diagnosis supporting information in the independent cohort separates patients of mental disease from the healthy people, only in accordance with the traveling subject method and the ComBat method, at the threshold value of 0.5.

Therefore, in the independent cohort, with respect to the GLM method and the adjusted GLM method, very low sensitivity (smaller than 0.5) and excessively high specificity are observed, while moderate sensitivity (about 0.5) and excessively high specificity are observed with respect to the method using raw data for the classifiers of MDD and SCZ. This means that patients and healthy people are not distinguished but classified collectively as healthy, and thus, resulted in excessively high specificity. These results suggest that the GLM method and the adjusted GLM method could not remove the site-to-site differences and possibly had a negative influence on the classification.

Figure 24:
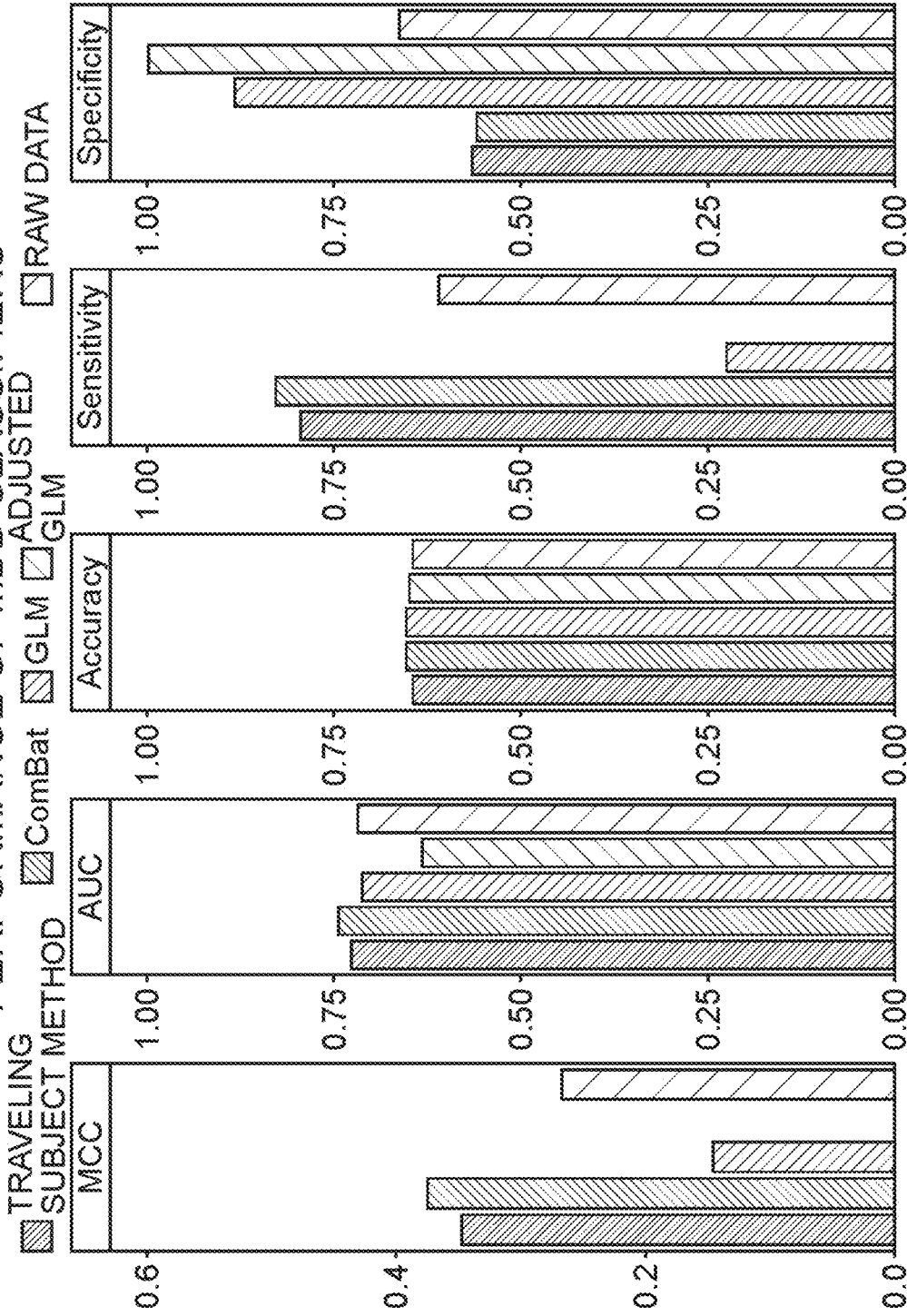
FIG. 24 shows classification performances on independent cohorts of MDD classifier.
Figure 25:
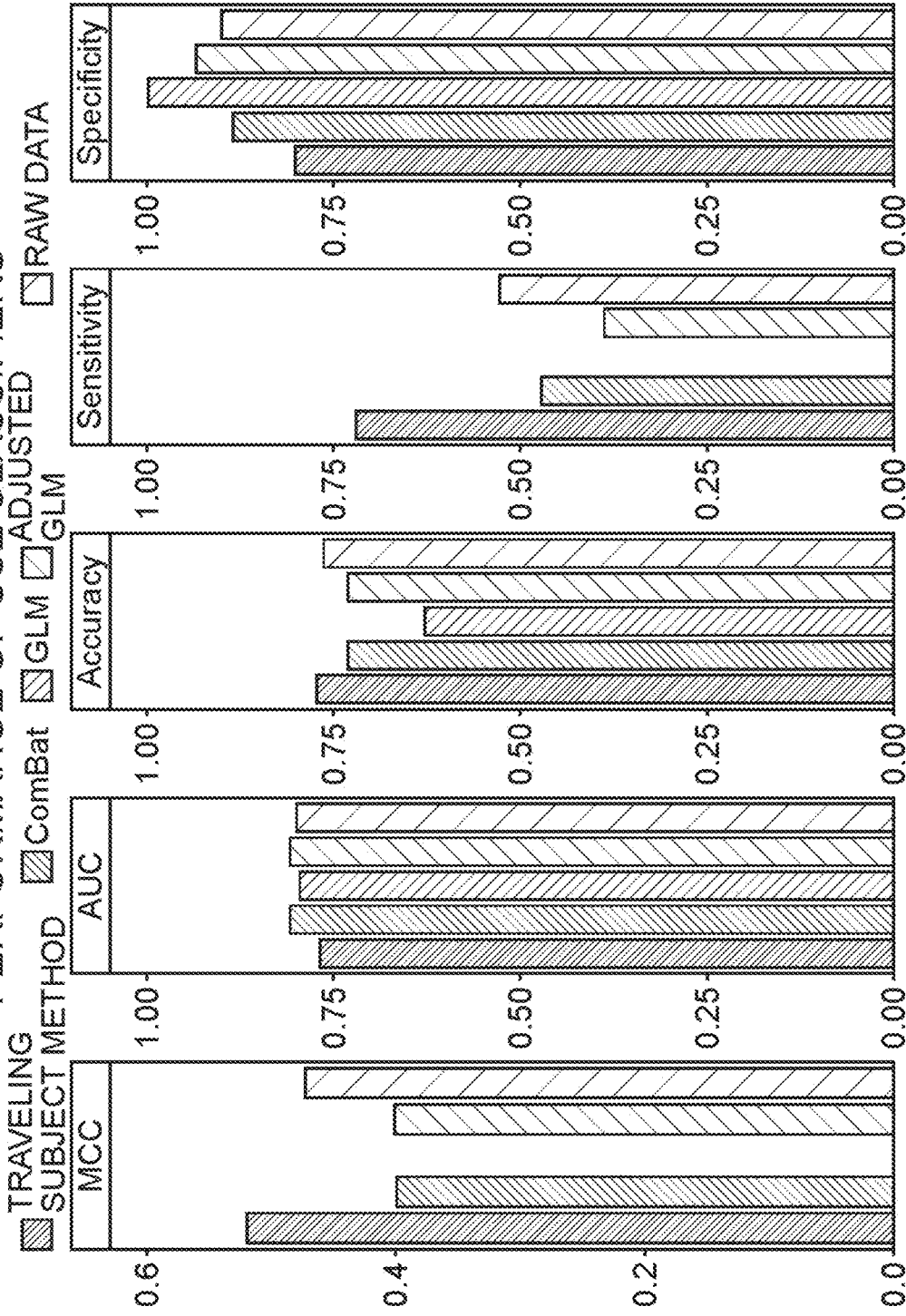
FIG. 25 shows classification performances on independent cohorts of SCZ classifier.

FIG. 24 shows classification performances on independent cohorts of the MDD classifier. FIG. 25 shows classification performances on independent cohorts of the SCZ classifier. The generalization to independent cohorts was directly examined without re-tuning the classifiers. The classifier outputs are defined as probabilities that the participants are classified to the MDD or the SCZ class.

Here, as classifier performances, we used Matthews correlation coefficients (MCC), ROC area under the curve (AUC) of Receiver Operating Characteristic curve, accuracy, sensitivity and specificity.

Using the traveling subject dataset (that is, the traveling subject method), a harmonization method was developed. The obtained harmonization method was compared with the existing harmonization methods. Comparison results show that the traveling subject method and the ComBat method outperformed the harmonization methods based on other conventional GLM methods as regards the generalization capability of mental disease classifiers and the development of regression models for predicting ages of the participants, as will be described later.

Further, it was shown that the generalization capability of the harmonization method based on the GLM method that cannot identify sampling biases and measurement biases was worse than that of the method based on the raw data, which was not harmonized across the sites.

The ComBat method attained the highest performance on the MDD classifier and the age regression model that will be described later, while it was inferior to the raw data as regards the SCZ classifier. The reason for this may be that the number of SCZ patients was small (n=48) and, therefore, the ComBat method could not clearly distinguish measurement biases and the relation of target attributes.

In contrast, the traveling subject method harmonizes only the measurement biases and, therefore, this method outperformed other harmonization methods based on conventional GLM methods, on the classifier and the regression model.

(Participants' Age Regression Models Based on Four Harmonization Methods)

In order to further examine the effectiveness of the harmonization methods, the regression models for predicting the participants' ages were built using the raw data method and four different harmonization methods, and the prediction performances of the models were compared.

For building each of the regression models, data (of 425 healthy people from nine sites) to which the machine learning technique was applied to every functional connectivity data from the healthy control was used. Linear regression was applied by using the LASSO method, and from a total of 35,778 connections, an optimal subset of the functional connections was selected. The prediction performance was evaluated in the training dataset using the ten-fold cross-validation procedure.

The generalization capability of models was examined partially using the fully independent validation cohort dataset obtained from ATR TimTrio, ATR Verio and ATR Prisma sites (232 HCs). The generalization to independent cohort was examined without the re-tuning of models.

Figure 26:
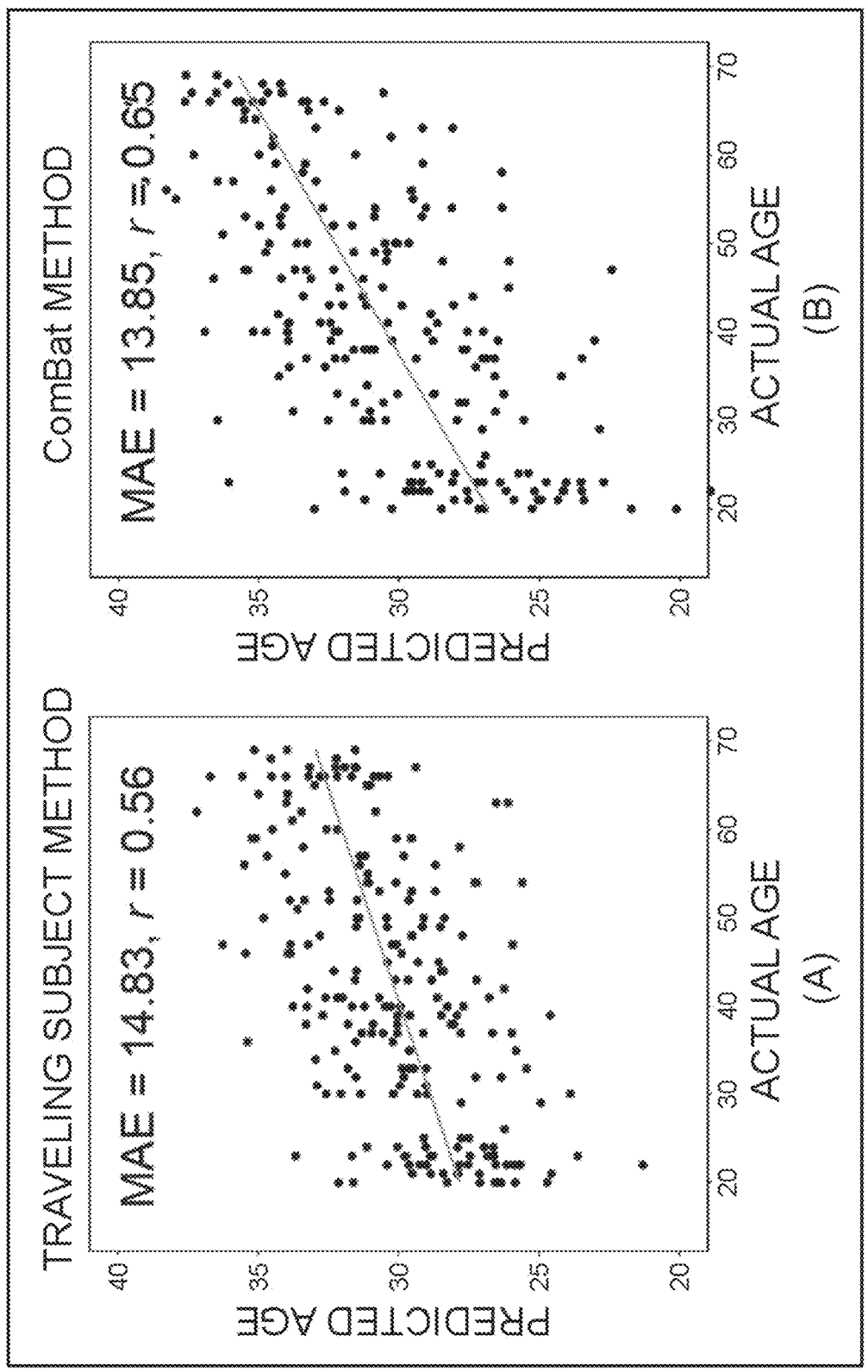
FIG. 26 shows a scatter diagram of actual ages and predicted ages in an independent cohort.
Figure 27:
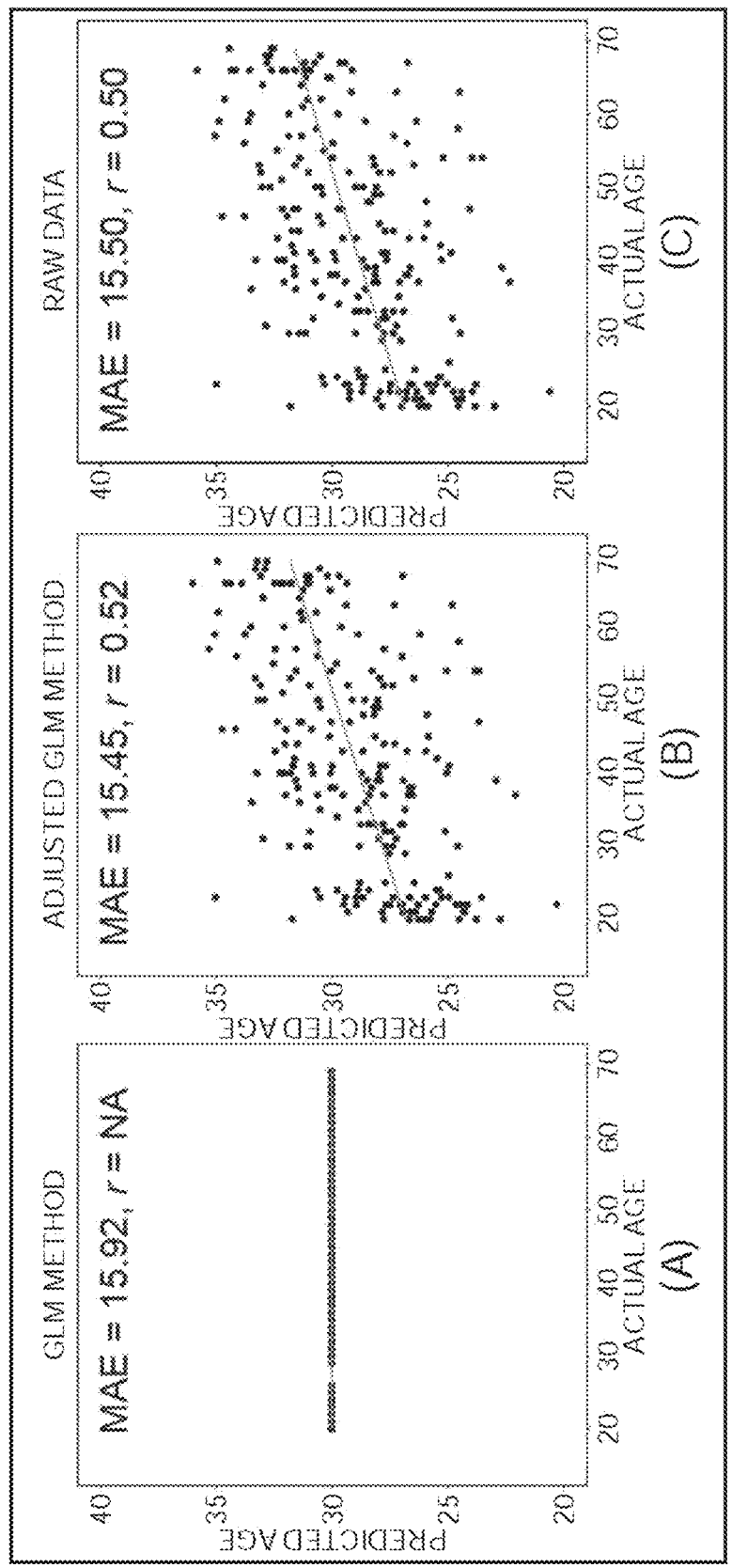
FIG. 27 shows a scatter diagram of actual ages and predicted ages in an independent cohort.

FIGS. 26 and 27 show scatter diagrams of actual ages and predicted ages in an independent cohort. In these figures, the solid lines represent linear regression of actual age from the predicted age. Mean absolute error (MAE) and correlation function (r) are shown in each graph. Each data point represents one participant. FIG. 26(A) shows the result of the traveling subject method, and FIG. 26(B) shows the result of the ComBat method.

FIG. 27(A) shows the result of the GLM method, FIG. 27(B) shows the result of the adjusted GLM method, and FIG. 27(C) shows the result of the method using the raw data (without harmonization of data across sites).

As can be seen from FIG. 26, the ComBat method attained the lowest Mean Absolute Value (MAE) and the highest r value, and the traveling subject method attained the second lowest MAE value and the second highest r value. Further, the MAE values of the ComBat method and the traveling subject method were significantly lower than the method using the raw data (two-sided paired t-test; ComBat: $p=3.1\times 10{-}20$, $t=-10.18$, $df=222$; traveling subject: $p=6.3\times 10{-}8$, $t=-5.5$, $df=222$).

These results show that the ComBat method and the traveling subject method had better performances than other harmonization methods that build regression models for predicting the participants' age as regards the generalization capability.

From the results above, it is understood that the traveling subject method is better than other methods as the method of harmonization for the data measured at a plurality of facilities from the viewpoint of generalization capability and of universal applicability to a larger number of attribute classifications.

Second Embodiment

In the configuration described in the first embodiment, the brain activity measuring devices (fMRI devices) measure data of brain activities obtained at a plurality of measuring sites, and based on the brain activity data, generation of biomarkers and estimation (prediction) of diagnosis labels by the biomarkers are realized by distributed processing.

It is noted, however, that the following process steps may be executed in a distributed manner at different sites:
  i) the measurement of brain activity data for training a biomarker through machine learning (data collection);
  ii) the process of generating a biomarker through machine learning and the process of estimating (predicting) diagnosis labels by the biomarker for a specific subject (estimation process); and
  iii) the measurement of brain activity data of the specific subject above (measurement of subject's brain activities).

Figure 28:
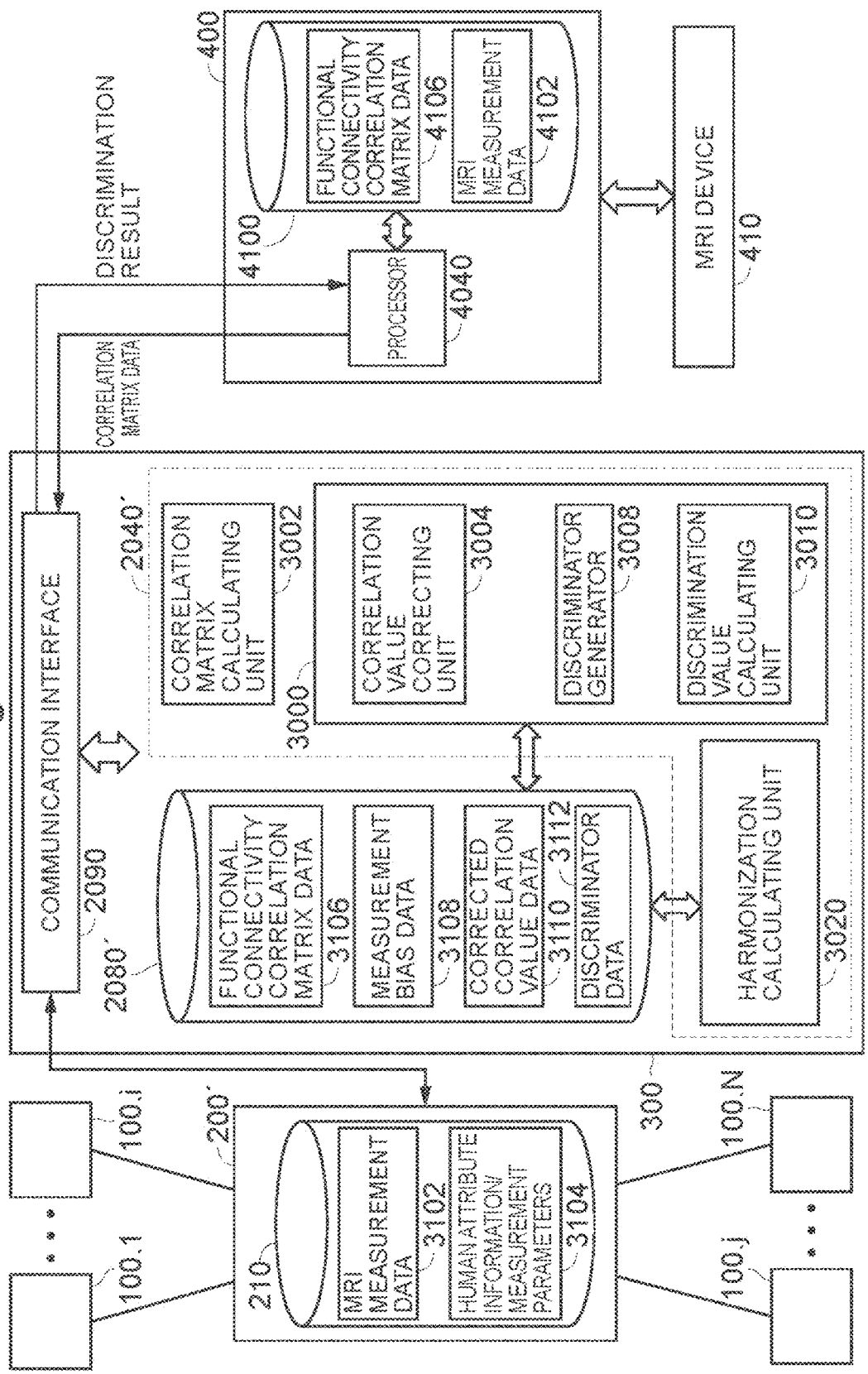
FIG. 28 is a functional block diagram showing an example when the data collection, the estimating process and the measurement of the brain activities of the subjects are processed in a distributed manner.

FIG. 28 is a functional block diagram showing an example when the data collection, the estimating process and the measurement of brain activities of subjects are processed in a distributed manner.

Referring to FIG. 28, sites 100.1 to 100.N represent facilities at which data of healthy cohort and patient cohort are measured by brain activity measuring devices, and a management server 200' manages measurement data from sites 100.1. to $100.N_s$.

Computing system 300 generates a discriminator from the data stored in server 200'.

Harmonization calculating unit 3020 of computing system 300 is assumed to execute the harmonization process including sites 100.1 to $100.N_sNs$ and the site of MRI measurement device 410.

An MRI device 410 is provided at a separate site that utilizes the results from the discriminator on computing system 300, and measures data of the brain activities of a specific subject.

A computer 400 is provided on a separate site where MRI device 410 is installed, and calculates the correlation data of the brain functional connectivity of the specific subject from the measurement data of MRI device 410, sends the correlation data of functional connectivity to computing system 300, and utilizes the results from the discriminator that are sent back.

Server 200' stores the MRI measurement data 3102 of patient cohort and healthy cohort transmitted from sites 100.1 to $100.N_s$ as well as the human attribute information 3104 of the subject associated with the MRI measurement data 3102, and in accordance with an access from computing system 300, transmits these data to computing system 300.

Computing system 300 receives MRI measurement data 3102 and human attribute information 3104 of the subject from server 200 through a communication interface 2090.

Hardware configurations of server 200', computing system 300 and computer 400 are basically the same as the configuration of "data processing unit 32" described with reference to FIG. 5 and, therefore, description thereof will not be repeated here.

Returning to FIG. 28, a correlation matrix calculating unit 3002, correlation value correcting unit 3004, discriminator generator 3008 and discrimination value calculating unit 3010, as well as correlation matrix data 3106 of functional connection, measurement bias data 3108, corrected correlation value data 3110 and discriminator data 3112 are the same as those described in the first embodiment and, therefore, description thereof will not be repeated here.

MRI device 410 measures the brain activity data of a subject whose diagnosis label is to be estimated, while processor 4040 of computer 400 stores the measured MRI measurement data 4102 in a non-volatile storage device 4100.

Further, a processor 4040 of computer 400 calculates functional connection correlation matrix data 4106 in the similar manner as correlation matrix calculating unit 3002, based on MRI measurement data 4102, and stores the calculated data in non-volatile storage device 4100.

A disease as an object of diagnosis is designated by a user of computer 400 and in accordance with an instruction of transmission by the user, computer 400 transmits the functional connection correlation matrix data 4106 to computing system 300. In response, computing system 300 executes the harmonization process corresponding to the site where the MRI device 410 is installed. Discrimination value calculating unit 3010 calculates the result of discrimination on the designated diagnosis label, and computing system 300 transmits the result of discrimination to computer 400 through communication interface 2090.

Computer 400 informs the user of the result of the discrimination using a display device or the like, not shown.

By such a configuration, it is possible to provide a larger number of users with the result of the estimation of the diagnosis label by the discriminator, based on the data collected from a larger number of users.

Further, server 200 and computing system 300 may be managed by separate administrators. In that case, by limiting the computers that can access server 200, it becomes possible to improve the security of tsubject information stored in server 200.

Further, from the viewpoint of the operator of computing system 300, the "service of providing result of the discrimination" becomes possible while not providing any information at all of the discriminator or information related to the "measurement biases" to the "side (computer 400) receiving the service of discrimination by the discriminator."

In the descriptions of 1st and 2nd Embodiments above, it is assumed that real-time fMRI is used as the brain activity detecting apparatus for time-sequentially measuring brain activities by functional brain imaging. It is noted, however, that any of the fMRI described above, a magnetoencephalography, a near-infrared spectroscopy (NIRS), an electroencephalography or any combination of these may be used as the brain activity detecting apparatus. Regarding such a combination, it is noted that fMRI and NIRS detect signals related to change in blood stream in the brain, and have a high spatial resolution. On the other hand, magnetoencephalography and electroencephalography are characterized in that they have a high temporal resolution, for detecting changes in an electromagnetic field associated with the brain activities. Therefore, if fMRI and the magnetoencephalography are combined, brain activities can be measured with both spatially and temporally high resolutions. Alternatively, by combining NIRS and the electroencephalography, a system for measuring the brain activities with both spatially and temporally high resolutions can also be implemented in a small, portable size.

By the configurations above, a brain activity analyzing apparatus and a brain activity analyzing method functioning as a biomarker using brain function imaging for neurological/mental disorders can be realized.

In the foregoing, an example has been described in which a "diagnosis label" is included as an attribute of a subject, and by generating a discriminator through machine learning, the discriminator is caused to function as a biomarker. The present invention, however, is not necessarily limited to such an example. Provided that a group of subjects whose results of measurements are to be obtained as the object of machine learning is classified into a plurality of classes in advance by an objective method, the correlation of degrees of activities (connection) among brain regions (regions of interest) of the subjects are measured and a discriminator can be generated for classification by machine learning using the measured results, the present invention may be used for other discrimination.

Further, as mentioned above, such discrimination may indicate by probability whether it belongs to a certain attribute.

Therefore, it is possible to objectively evaluate whether taking a certain "training" or following a certain "behavior pattern" is effective to improve the health of a subject or not. Further, it is also possible to objectively evaluate whether certain ingestions of "food" or "drink" or a certain activity or activities are effective to reach a healthier state before onset of a disease (in the state of "not yet diseased").

Further, even before the onset of a disease, if an indication such as "probability of being healthy: XX %" is output as mentioned above, it is possible to provide the user with an objective numerical value of his/her state of health. Here, the output may not necessarily be the probability. For example, "a continuous value of degree of healthiness, such as probability of being healthy" converted to a score may be displayed. By providing such a display, the apparatus in accordance with the embodiments of the present invention can be used as an apparatus for health management of users.

Third Embodiment

In the foregoing description, it is assumed that the traveling subjects travel to every measurement site and have measurements equally, and thereby measurement biases are evaluated.

Figure 29:
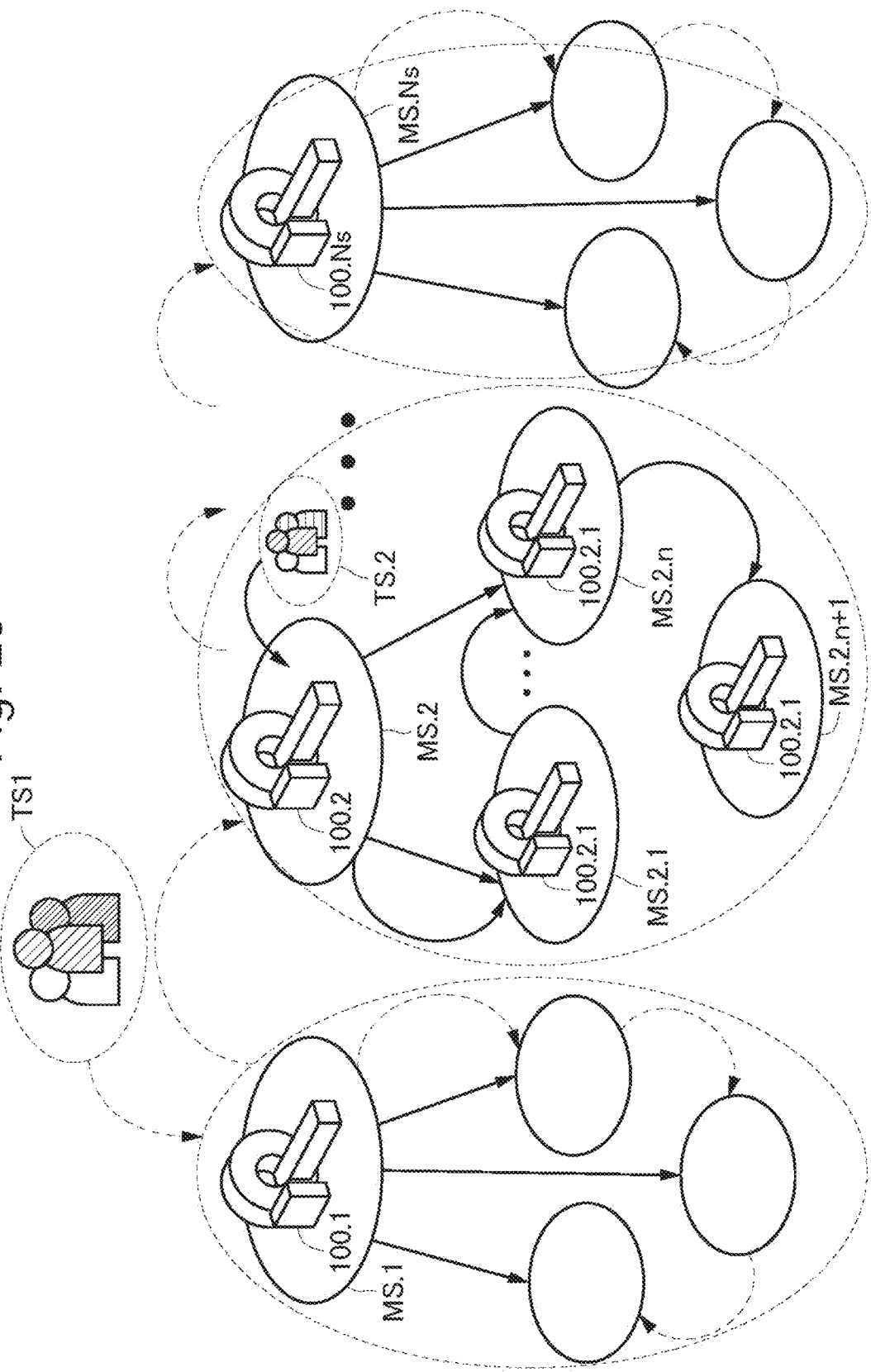
FIG. 29 shows the routing of the traveling subjects in accordance with a third embodiment.

FIG. 29 shows a circuiting scheme of the traveling subjects in accordance with a third embodiment. In the third embodiment, as shown in FIG. 29, it is assumed that the traveling subject TS1 makes the rounds of the "hub measurement sites MS.1 to MS.$N_s$" as hubs.

Among these hub measurement sites MS.1 to MS.$N_s$, assume that there are subordinate sites MS2.1 to MS2.$n$ under the hub measurement site MS.2. If a new measurement site "MS.2.$n$+1" is added to the sites under hub measurement site MS.2, a traveling subject TS2 makes the rounds of the sites under the hub measurement site MS.2. The same applies to other hub measurement sites.

Specifically, a configuration is also possible wherein the measurement biases of hub measurement site MS.2 are fixed to the values evaluated concerning the traveling subject TS1 and the measurement biases of the measurement sites MS.2, MS.2.1, MS.2.$n$ and MS2.$n$+1 may be determined based on the measurement results of the traveling subject TS2 making the rounds of these sites.

By way of example, the "hub measurement sites MS.1 to MS.$N_s$" may exist at predetermined regions. For instance, one hub may be located in each of such areas as Hokkaido, Tohoku, Kanto, Kansai, . . . , and Kyushu areas in Japan, and the subordinate sites may be located in one of these areas, for example, in the Kansai area.

Alternatively, the "hub measurement sites MS.1 to MS.$N_s$" may be selected in accordance for each of the predetermined types of MRI devices. In that case, the subordinate measurement sites will be the measurement sites where the same type of the MRI device as the hub is installed.

Alternatively, the "hub measurement sites MS.1 to MS.$N_s$" may be selected for area by predetermined area and type by the predetermined type of MRI devices. In that case, the limb measurement sites are the measurement sites located in the same area as the hub site and having the same MRI device as the hub installed.

By such configurations also, the same effects as in the first embodiment can be attained.

Fourth Embodiment

In the following, the process of generating a classifier will be described concerning major depressive disorders as an example among mental diseases, or more specifically, concerning a group of patients diagnosed as having major depressive disorder by doctors in accordance with the conventional method of symptom-based diagnosis approach. That is, another example will be described in the following concerning the process executed by the discriminator generator 3008 shown in FIG. 10 or FIG. 28 to generate a classifier that outputs assisting information for discriminating a patient cohort from a healthy cohort.

In the following, we will describe a procedure of building an MDD classifier for identifying a healthy control (HC) and a MDD patient based on the functional connectivity FC. In order to specify functional connections FC related to the MCC diagnosis, we will also examine which functional connectivity FC is important for building the classifier.

Further, in the following, we will build a regression model for Beck Depression Inventory II. Beck Depression Inventory II is one of the most widely used tests related to measuring the severity of depressive symptoms. Then, we examine which functional connectivity is important for the regression model in order to distinguish an FC related to the depressive symptoms. Further, we examine the resting state functional connectivity FC that are common to the functional connectivity related to the MDD diagnosis and the functional connectivity FC related to the depressive symptoms.

As already described above, in order to build reliable classifiers and regression models using the machine learning algorithms, it is necessary to use data of a large sample size collected from many imaging sites. Therefore, in the following, we use a resting state fMRI dataset for learning of about 700 participants, including the MDD patients, collected from four different imaging sites.

FIG. 30 shows the demographic characteristics of the training dataset (first dataset). The first dataset is the data in the above-described SRPBS dataset. FIG. 31 shows the demographic characteristics of the independent validation dataset (second dataset). The second dataset is also, basically, the data in the SRPBS above.

Specifically, in the following analysis, the following two resting state functional MRI (re-fMRI) datasets are used.
(1) As shown in FIG. 30, the first dataset includes data of 713 participants (564 healthy controls HCs from four sites, 149 MDD patients from three sites).
(2) As shown in FIG. 31, the second dataset includes data of 449 participants (264 healthy controls HCs from four sites, 185 MDD patients from four sites).

Further, "depressive symptoms" are evaluated by using the Beck Depression Inventory II (BDI) obtained from most of the participants of each dataset.

The first dataset is a "training dataset" and used for building an MDD classifier and a BDI linear regression model.

Each of the measurements of participants was carried out in a single 10-minute session of resting state functional MRI (re-fMRI).

Here again, the resting state functional MRI (re-fMRI) data was obtained under the standardized imaging protocols (http://www.cns.atr.jp/rs-fmri-protocol-2/). As in the first embodiment, however, it is actually difficult to ensure that every image diagnosis was done at every site using the same parameters, and two phase modulation directions (P→A and A→P), MRI devices of two manufacturers (Siemens and GE), three different coil numbers (12, 24, 32) and scanners of three model numbers were used for measurements.

During the scanning of the resting state functional MRI (rs-fMRI), typically, an instruction such as shown below is given to each participant.

"Please try to relax. Try to stay awake. Gaze at the cross mark at the center and do not think about any specific things."

The "demographic characteristics" in the dataset are the characteristics used in the so-called "demographics," and include the age, sex and attributes such as the diagnosis listed in the table. In FIGS. 30 and 31, the number of participants in the parentheses indicates the number of participants having the BDI score data. The demographic distributions match between the MDD and the HC sample groups in every training dataset ($p>0.05$).

The second dataset is the "independent validation dataset," which is used for testing the MDD classifiers and the BDI regression models. The sites used for the imaging of the second dataset are not included in the first dataset.

The demographic distribution of age matches between the MDD and the HC sample groups ($p>0.05$) in the independent validation dataset, while the demographic distribution of sex does not match between the MDD and the HC sample groups in the independent validation dataset ($p<0.05$).
(Preprocessing and Calculation of Resting State Functional Connectivity FC Matrix)

The first 10 seconds of data are discarded to take the T1 equilibrium into consideration.

The preprocessing step includes the calibration of slice timing, the re-alignment process for correcting body motion artifacts observed at one's head, co-registration of the brain functional image (EPI image) and the structural image, the distortion correction, segmentation of the T1 enhanced structural image, the normalization to the MNI (Montreal Neurological Institute) space, and spatial smoothing using the isotropic Gaussian kernel of 6 mm full-width at half maximum.

The above-described pipeline pre-processing is disclosed, for example, at the site below.

http://fmriprep.readthedocs.io/en/latest/workflows.html
(Parcellation of Brain Regions)

For parcellation of the brain regions, the toolbox (ciftify toolbox version 2.0.2) disclosed at the site below was used to analyze data by the "surface-based method" of the Human Connectome Project (HCP) style.
https://edickie.github.io/ciftify/#/This toolbox enables the analysis of used data (which lacks T2 enhanced images necessary for the HCP pipeline) in a surface-based pipeline similar to the HCP.

In the following analysis, 379 surface-based areas (360 cortex areas+19 subcortical areas) disclosed in Reference 13 below are used. The disclosure of Reference 13 is incorporated herein by reference in its entirety.

Reference 13: Glasser, M. F., Coalson, T. S., Robinson, E. C., Hacker, C. D., Harwell, J., Yacoub, E., et al. (2016). A multi-modal parcellation of human cerebral cortex. Nature 536(7615), 171-178. doi: 10.1038/nature18933.

Changes of BOLD signals over time are extracted from these 379 regions of interest (ROI).

Further, by the automatic anatomical labeling (AAL) as disclosed in Reference 14 below and by the use of Neurosynth (http://neurosynth.org/locations/), anatomical names of important ROIs and the names of intrinsic brain networks including the ROIs are specified. The disclosure of Reference 14 is incorporated herein by reference in its entirety.

Reference 14: Tzourio-Mazoyer, N., Landeau, B., Papathanassiou, D., Crivello, F., Etard, O., Delcroix, N., et al. (2002). Automated anatomical labeling of activations in SPM using a macroscopic anatomical parcellation of the MNI MRI single-subject brain. Neuroimage 15(1), 273-289. doi: 10.1006/nimg.2001.0978.
(Physiological Noise Regression)

Physiological noise regression is executed by applying the CompCor disclosed in Reference 15 below. The disclosure of Reference 15 is incorporated herein by reference in its entirety.

Reference 15: Behzadi, Y., Restom, K., Liau, J., and Liu, T. T. (2007). A component based noise correction method (CompCor) for BOLD and perfusion based fMRI. Neuroimage 37(1), 90-101. doi: 10.1016/j.neuroimage.2007.04.042.

In order to remove some sources of spurious (undesirable signal sources), the linear regression with regression parameters such as six kinematic parameters, whole brain etc. is used.

(Temporal Filtering)

A temporal bandpass filter is applied to the time-sequential data using Butterworth filter having pass bands between 0.01 Hz and 0.08 Hz, so that the analysis is limited to low-frequency fluctuation characteristic to the BOLD behavior.

(Head Movement)

In each functional session, frame-wise displacement (FD) is calculated, and in order to reduce variation in spurious of the functional connectivity FC caused by head movement, any volume having FD>0.5 mm is removed. FD represents head movement between two temporally continuous volumes as a scalar quantity (that is, the sum of absolute displacements in translation and rotation).

In the specific dataset as mentioned above, if the ratio of volume removed after scrubbing exceeds (average±3 standard deviation), the data of the corresponding participant is excluded from the analysis. As a result, for the whole dataset, 35 participants were excluded.

Hence, of the training dataset, 683 participants (545 HCs and 138 MDD) were used, and of the independent validation dataset, the data of 444 participants (263 HCs, 181 patients of MDD) was used for the analysis below.

(Calculation of Functional Connectivity (FC) Matrix)

In a specific example in accordance with the present embodiment, the functional connectivity FC is calculated as a temporal correlation of the BOLD signals over 379 regions of interest (ROIs) for each participant.

Though not limiting, for calculating functional connectivity, here again, the Pearson's correlation coefficient is used. The Pearson's correlation coefficient subjected to Fisher z transformation of pre-processed BOLD signals over time of each possible set of ROIs is calculated, and a symmetrical connectivity matrix of 379 rows×379 columns, of which element each representing the strength of connection between two ROIs, is formed. Further, for reasons of analysis, the values of the functional connectivity of the lower triangular matrix of 71,631 (=(379×378)/2) of the connectivity matrix are used.

(Site Effect Control)

Further, in the following, in order to control site effect on the functional connectivity, description will be made assuming that the traveling subject harmonization method as described in the first to third embodiments is used for the training dataset. It is noted, however, that the harmonization method is not limited to this, and other methods, such as the above-described ComBat method, may be used.

The traveling subject harmonization method makes it possible to remove the pure site-to-site differences (measurement biases). Note that no dataset of the traveling subject existed for the site or sites included in the independent validation dataset and, therefore, in order to control site effects in the independent validation dataset, harmonization was done using the ComBat method.

(Classifier for MDD in Training Data Set)

A biomarker for the MDD is built using the above-described training dataset as the training data for a classifier. The marker is to identify a group of healthy controls (a group of samples having a diagnosis label of healthy control (HC)) and a group of MDD patients (a group of samples having a diagnosis label of Major Depressive Disorder) based on 71,631 values of functional connectivity FC.

Figure 32:
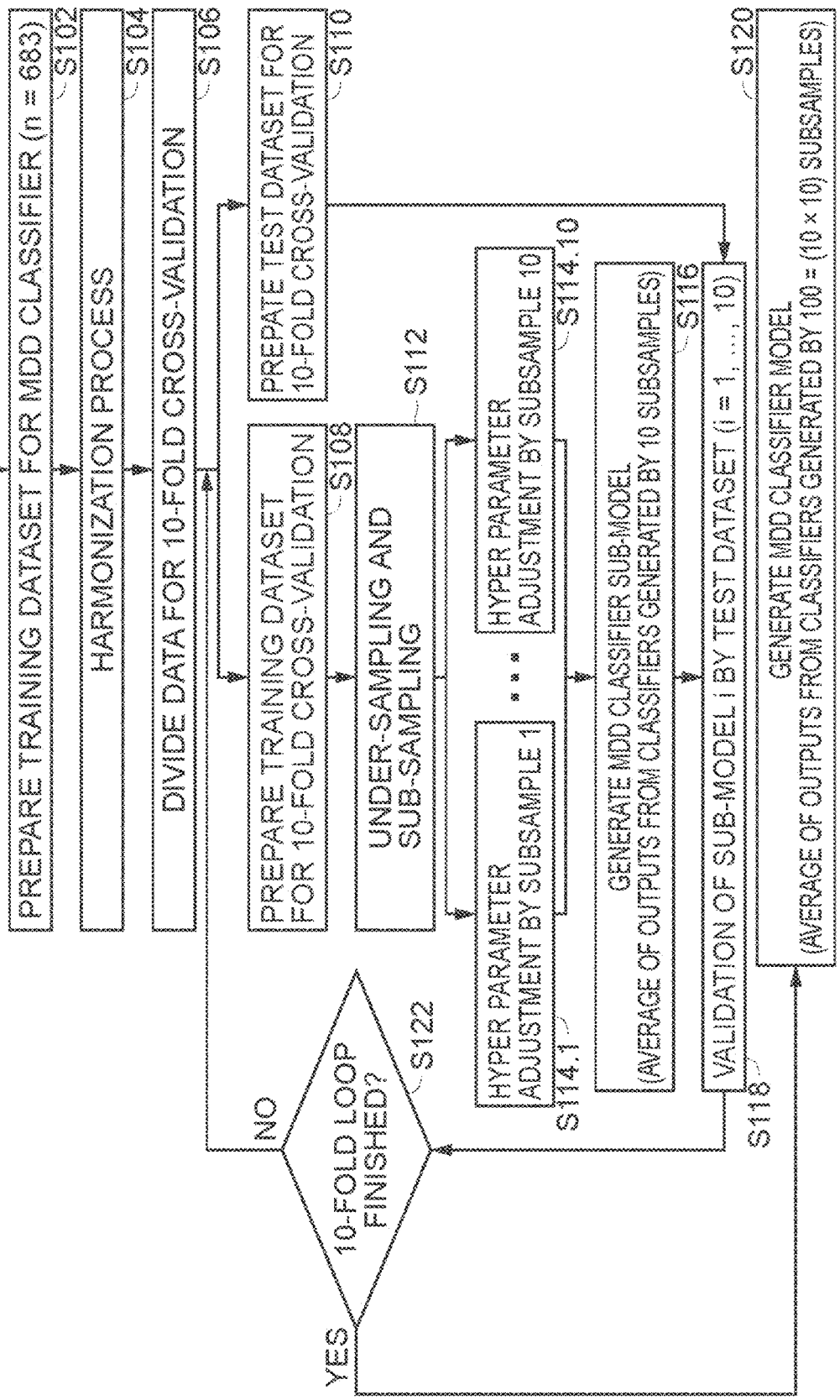
FIG. 32 is a flowchart showing a procedure of machine learning for generating a classifier.

FIG. 32 is a flowchart showing a procedure of machine learning for generating such a classifier.

As will be described in the following, in the learning process for generating a classifier for MDD (hereinafter referred to as an MDD classifier), using the logistic regression analysis (one of sparse modeling methods) by the L1 regularization (LASSO: least absolute shrinkage and selection operator), an optimal subset of the functional connections FC is selected from 71,631 functional connections FC. Generally, when L1 regularization is used, some parameters (in the following description, weight elements) can be reduced to zeros. In other words, feature selection is done, resulting in a sparse model. It is noted, however, that the method of sparse modeling is not limited to the above, and other methods such as the variational Bayesian method or the sparse logistic regression (SLR) which applies the variational Bayesian method to the logistic regression, may be used.

Referring to FIG. 32, when the process of learning for the MDD classifier starts (S100), using pre-prepared (and stored in storage device 2080') training dataset (S102), correlation matrix calculating unit 3002 calculates elements of the connectivity matrix.

Thereafter, harmonization calculating unit 3020 calculates measurement biases and executes the harmonization process (S104). As described above, the harmonization process using traveling subjects is preferred, though other methods may be used.

Thereafter, discriminator generator 3008 generates the MDD classifier by applying a method which is a modification of a so-called Nested Cross Validation on the training data.

First, to execute the training process using the "K-fold cross validation" (K is a natural number) (external cross-validation), discriminator generator 3008 sets K to 10, for example, and divides the training data into 10 subsets.

Specifically, discriminator generator 3008 uses one of the subsets of the K-fold (10-divided) data as a "test dataset" for validation, and assigns the remaining (K−1) (9-divided) data as training dataset (S108, S110).

Then, discriminator generator 3008 executes an under-sampling process and a sub-sampling process on the training dataset (S112).

Here, the "under-sampling process" means a process executed to even out the numbers of data corresponding to the (two or more) specific attribute data to be classified to when their numbers are different. Here, in the training dataset, the number of subjects of the MDD patient cohort is not equal to the number of subjects of healthy control cohort and, therefore, the process to equalize is executed.

Further, the "sub-sampling process" means a process of extracting a prescribed number of random samples from the training dataset. Specifically, in the cross validation repeated K times through steps S108 to S118 and S122, in each cross validation, under-sampling is done for building the classifier since the numbers of the MDD patients and the healthy control HC are imbalanced in the training dataset and, in addition, a prescribed number, for example, 130, of the MDD patients and the same number of healthy people are sampled at random from the training dataset as the sub-sampling process.

The number "130" is not limiting, and it is determined appropriately to enable the above-described under-sampling, in accordance with the amount of data in the training dataset (683 in the first dataset), the fold number K (here, K=10) and the degree of imbalance of the numbers of data respectively corresponding to specific attributes as the objects of classification.

Sub-sampling such as described above is executed, since under-sampling is disadvantageous in that the removed data cannot be used in training the classifier. Random sampling (or sub-sampling) is repeated M times (M=natural number, for example, M=10) to avoid the disadvantage.

Thereafter, discriminator generator 3008 executes a process for adjusting hyper parameters for each of the sub-samples 1 to 10 that have been sub-sampled (S114.1 to S114.10).

Here, by using the following logistic function on each subsample, a classifier sub-model is generated. The logistic function is used for defining the possibility of a participant in the subsamples belonging to the MDD class as follows.

$$P_{sub}(y_{sub} = 1 \mid c_{sub}; w) = \frac{1}{1 + \exp(-w^T c_{sub})}$$

Here, $y_{sub}$ represents a class label of the participant (MDD, y=1; HC, y=0), $c_{sub}$ represents an FC vector for a given participant, and w represents a weight vector. The weight vector is determined to minimize the following evaluation function (cost function) (LASSO calculation).

$$J(w) = -\frac{1}{n_{sub}} \sum_{j=1}^{n_{sub}} \log P_j(y_j = 1 \mid c_j; w) + \lambda \|w\|_1$$

$$\|w\|_1 = \sum_{i=1}^{N} |w_i|$$

In the LASSO calculation, the sum (L1 norm) of absolute values (1st order) of elements of the weight vector exists as the second term in the cost function. Here, λ represents a hyper parameter and it controls the amount of shrinkage used for the evaluation.

In each subsample, though not limiting, discriminator generator 3008 uses a prescribed number of data as hyper parameter adjusting data and uses the remaining data (for example, n=250 or data of 248 participants) to determine the weight vector w. Though not specifically limiting, here, discriminator generator 3008 assumes that the hyper parameter λ is 0<λ≤1.0, divides this range equally by P (P: natural number), for example, by 25, and using each of the resulting λ values, determines the weight vector w by the LASSO calculation mentioned above.

Here, as the "Nested Cross Validation" as described above, hyper parameter adjustment is done as the "internal cross validation." In the internal cross validation, the "test dataset" of the external cross validation is not used.

Then, discriminator generator 3008 compares the discrimination performance of the hyper parameter adjusting data using a logistic function corresponding to each generated λ value, and determines the logistic function that corresponds to λ attaining the highest discrimination performance (hyper parameter adjustment process).

Thereafter, discriminator generator 3008 sets a "classifier sub-model" that outputs an average of output values of the logistic function corresponding to the subsamples generated in the current loop of cross validation (S116).

Using the test dataset prepared at step S110 as an input, discriminator generator 3008 executes the validation of the classifier sub-model generated in the current loop of cross validation (S118).

As the method of generating subsamples by under-sampling and sub-sampling, the executing feature selection in each subsample and thereby generating a classifier sub-model, sparse modeling methods may be used other than the methods of using the LASSO method and the hyper parameter adjustment described above.

If it is determined that the K-th (here, 10th) cross validation loop has not yet been finished (N at S122), discriminator generator 3008 selects a sub-dataset of the K-divided data which is different from those used in past loops as the test dataset, and assigns the remaining sub-datasets as the training dataset (S108, S110), and repeats the process.

On the other hand, if it is determined that the K-th (here, 10th) cross validation loop is finished (Y at S122), discriminator generator 3008 generates a classifier model for the MDD (MDD classifier) (S120) that outputs an average of outputs of K×M (here, 10×10=100) logistic functions (classifiers) for the input data.

When the output of the MDD classifier (probability of diagnosis) exceeds 0.5, it can be regarded as an index pointing to an MDD patient.

In the present embodiment also, as indexes for evaluating the performance of the MDD classifier generated in the above-described manner, Matthews correlation coefficients (MCC), AUC (area under the curve) of ROC (Receiver Operating Characteristic curve), accuracy, sensitivity and specificity are used.

The method of generating a classifier of an object disease (for example, MDD) by using a selected feature (here, elements of the correlation matrix after the harmonization of the measurement biases) selected at each subsample is not limited to the process of averaging outputs of a plurality of classifier sub-models as described above. Such a classifier may be generated by using other modeling methods, particularly other sparse modeling methods, on the selected features.

Figure 33:
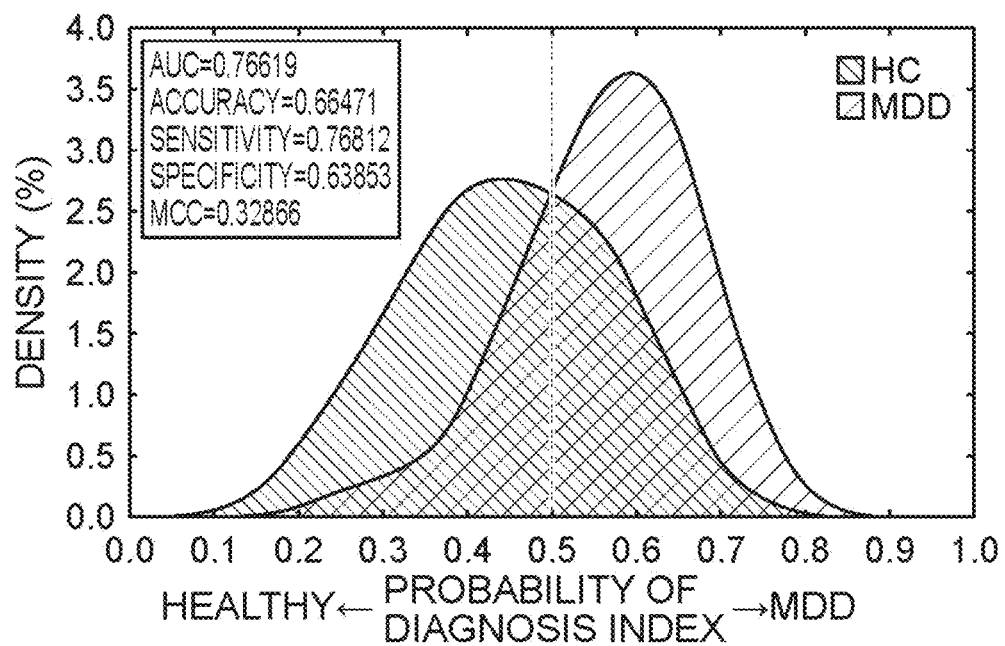
FIG. 33 shows the prediction performance (output probability distribution) of MDD on the training dataset for all imaging sites.

FIG. 33 shows the prediction performance (output probability distribution) of MDD on the training dataset for all imaging sites. In the outputs from a classifier model for the training dataset, probability distributions of two diagnoses corresponding to the groups of the MDD patients and the healthy people are clearly separated to right (MDD) and left (HC) at the threshold value of 0.5.

The classifier model separates the MDD patients from the HC cohort with the accuracy of 66%. The corresponding AUC is 0.77, showing a high discriminating ability. The MCC is about 0.33.

Figure 34:
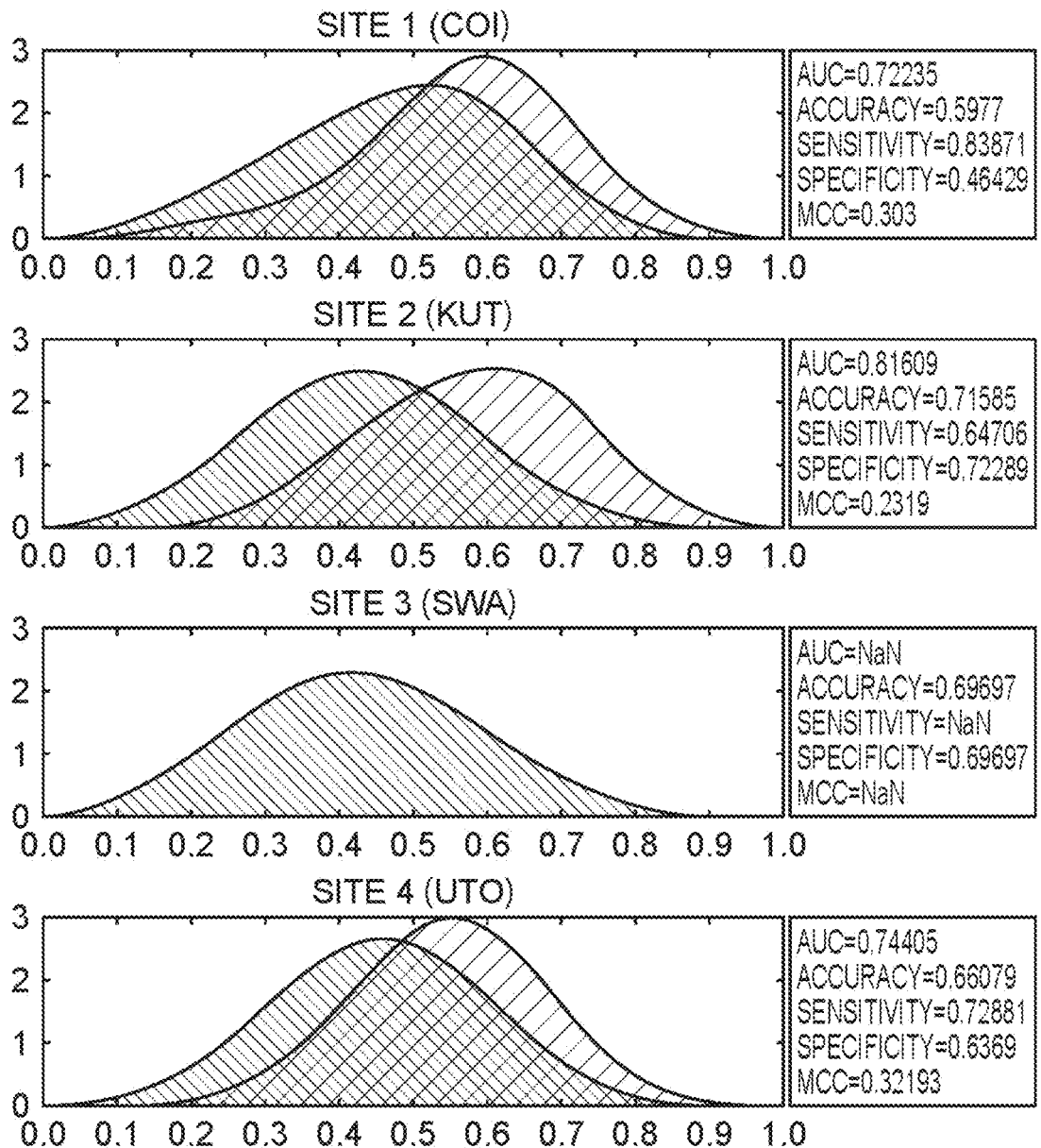
FIG. 34 shows the prediction performance (classifier output probability distribution) of the MDD on the training dataset for each imaging site.

FIG. 34 shows the prediction performance (classifier output probability distribution) of MDD on the training dataset for each imaging site. It can be seen from FIG. 34 that not only for the entire dataset but for respective datasets of the three imaging sites (site 1, site 2, site 4), almost equally high classification accuracies could be attained.

It is noted that in the dataset of site 3 (SWA), only a healthy control cohort exists. Its probability distribution, however, corresponds to that of the healthy controls of other sites.

(Classifier Generalization Capability)

Figure 35:
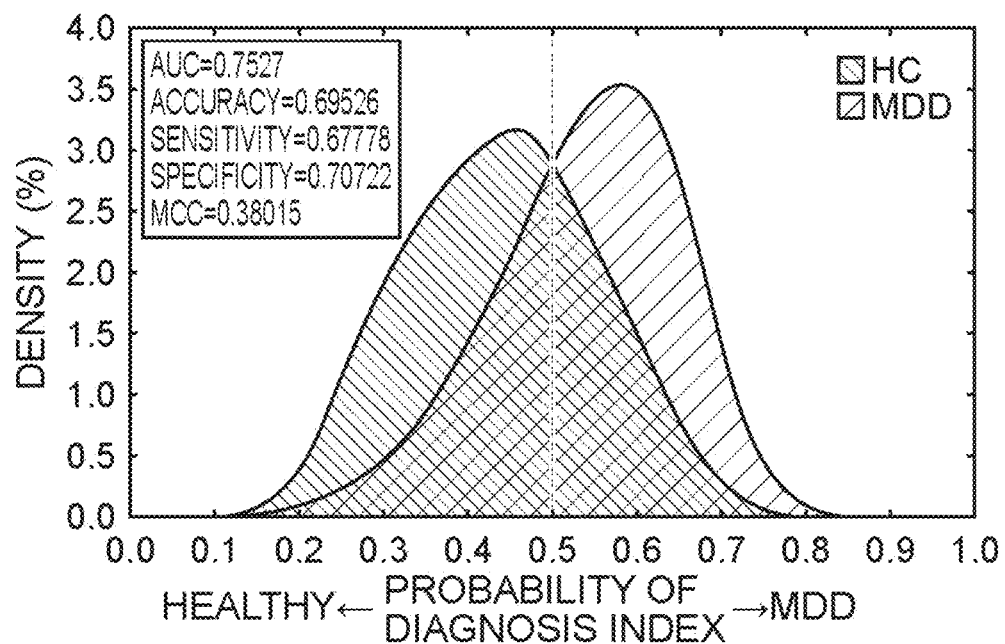
FIG. 35 shows classifier output probability distributions of the MDD on the independent validation dataset.

FIG. 35 shows the classifier output probability distribution of the MDD on the independent validation dataset. Specifically, the generalization capability of the classifier models is tested using an independent validation dataset.

Regarding MDD, in the process shown in FIG. 32, 100 (10-fold×10 sub-samplings) the logistic function classifiers are generated by machine learning. An independent validation dataset is input to each of the generated 100 classifiers (classifier models as a set of classifiers). For each participant, an average of outputs from 100 classifiers (probability of diagnosis) is calculated. If the averaged probability of diagnosis is >0.5, it is determined that the diagnosis label assigned to the corresponding participant is major depressive disorder.

In the independent validation dataset, the generated classifier models separate the MDD sample group from the HC sample group with the accuracy of about 70%. The corresponding AUC is 0.75, indicating a performance attaining high discrimination capability (permutation test p<0.01).

For the independent validation dataset, by the threshold value of 0.5, the probability distribution of outputs from the classifier models are clearly separated into two diagnoses corresponding to the groups of the MDD patients and the healthy people, that is, to the right (MDD) and to the left (HC). Sensitivity is 68% and specificity is 71%, which leads to a high MCC value of 0.38 (permutation test p<0.01).

Figure 36:
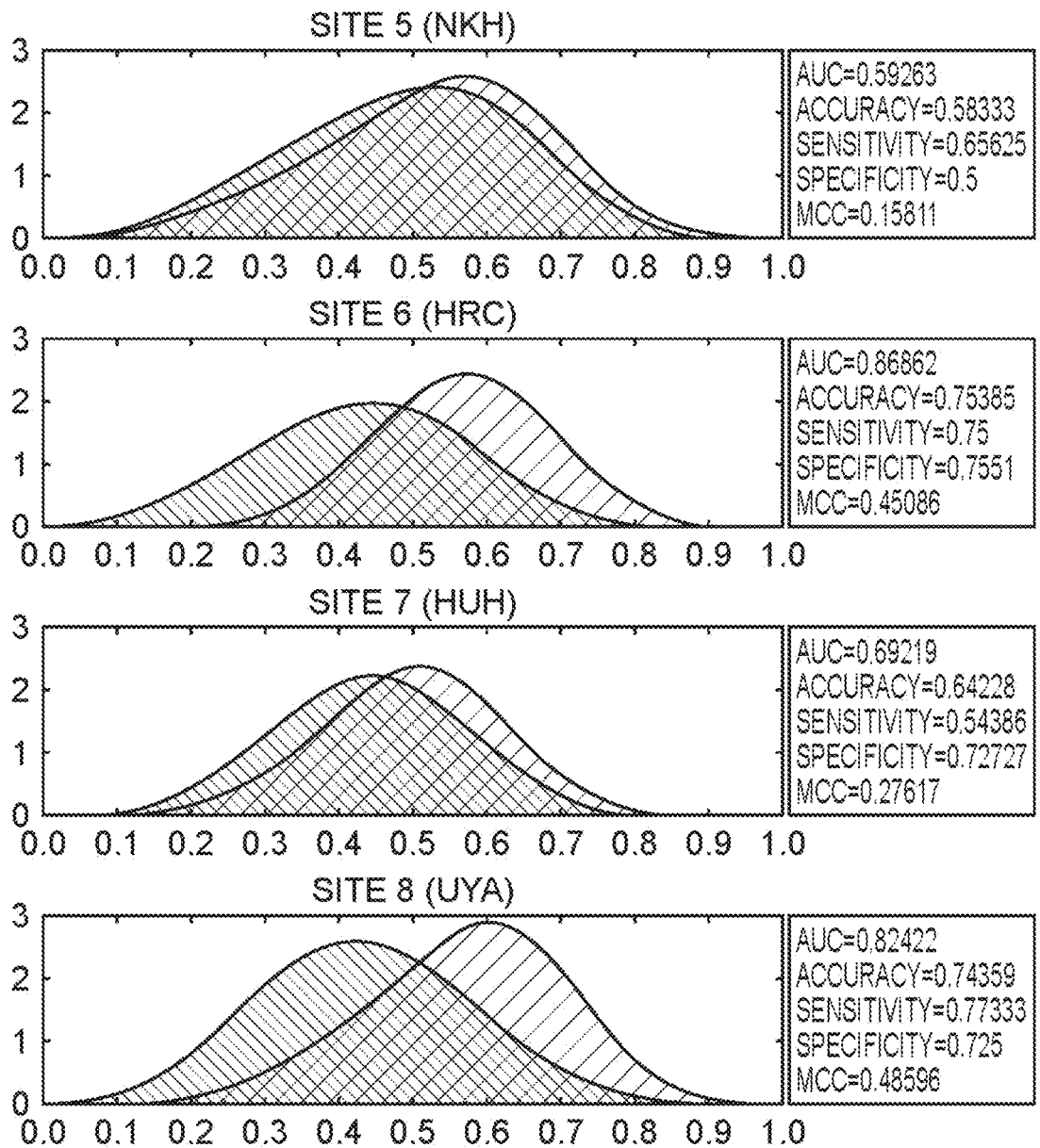
FIG. 36 shows classifier output probability distributions of the MDD with respect to the independent validation dataset for each imaging site.

FIG. 36 shows the classifier output probability distribution of the MDD with respect to the independent validation dataset for each imaging site. It can be seen that a high classification accuracy can be attained not only for the whole dataset of the four imaging sites but also for the individual dataset.

In the foregoing, an example has been described in which an average of outputs of the K×M logistic functions (classifiers) generated in accordance with the flowchart of FIG. 32 becomes the classifier model (MDD classifier). By such an arrangement, it becomes possible to generate a classifier capable of classifying a group of healthy people and a group of patients with a sufficiently high generalization capability, based on the brain activity information (time-sequential resting state fMRI images) measured by the different measurement devices at a plurality of the measurement sites.

It is noted, however, that the procedure to form an MDD classifier after the harmonization process is not limited to the one described above. By way of example, an MDD classifier corresponding to the "diagnosis label" may be generated by the "sparse modeling" method such as disclosed in Reference 16 or 17 below. Disclosures of References 16 and 17 are incorporated herein by reference in their entirety.

Reference 16: JP patent No. 6341513
Reference 17: JP patent No. 6195329

For example, according to JP patent No. 6195329, from the resting state functional connectivity MRI data measured for the groups of healthy people and patients, a correlation matrix of degrees of activities between the prescribed brain regions is derived. By the Sparse Canonical Correlation Analysis (SCCA) on the correlation matrix and on the attributes of subjects including the diagnosis labels of the subjects, elements of the correlation matrix connected to a canonical variable that corresponds only to the diagnosis label are extracted. On a first sum set of the elements of the correlation matrix obtained by feature extraction by the Sparse Canonical Correlation Analysis, the sparse logistic regression with leave-one-out cross validation is conducted to extract a second sum set of elements of the correlation matrix. By the discriminate analysis using the sparse logistic regression on the second sum set, a classifier is generated.

The sparse logistic regression refers to a method of a logistic regression analysis expanded to a Bayes' estimation scheme, in which the dimensionality reduction of a feature vector is performed concurrently with the weight estimation for discrimination. This is useful when the feature vector is in a very large dimension and includes many unnecessary feature elements. For the unnecessary feature elements, weight parameters in the linear discrimination analysis will be set to zeros (that is, feature selection is done), so that only a limited number of feature elements related to the discrimination are extracted (sparseness).

In the sparse logistic regression, the probability p of the obtained feature data belonging to a class is calculated for each class, and the feature data is classified to the class corresponding to the highest output value. The value p is output by a logistic regression equation. The weight estimation is done by the ARD (Automatic Relevance Determination), and feature elements with little contribution to class determination are removed from the calculation as its weight approaches zero.

References 18 and 19 below disclose the sparse logistic regression as such. Disclosures of References 18 and 19 are incorporated herein by reference in their entirety.

Reference 18: Okito Yamashita, Masaaki Sato, Taku Yoshioka, Frank Tong, and Yukiyasu Kamitani. "Sparse Estimation automatically selects voxels relevant for the decoding of fMRI activity patterns." NeuroImage, Vol. 42, No. 4, pp. 1414-1429, 2008.

Reference 19: Kazuhiko SAGARA, Yasuto TANAKA, Hiroshige TAKEICHI, Okito YAMASHITA, Ryohei HASEGAWA, Tatsuya OKABE and Taro MAEDA, "Brain Communication—Nou to shakai no tsuushin shudan" (Brain Communication—Communication Means between Brain and Society), edited by IEICE (Institute of Electronics, Information and Communication Engineers), Corona-sha, Apr. 25, 2011, 1st edition, 1st issue (Extraction of functional brain connectivity common to diagnosis and symptoms)

Conventionally, as disclosed in Reference 20 below, when a biomarker is to be built for identifying a group of healthy controls (HCs) and a group of MDD patients based on the resting state functional connectivity, the MDD diagnosis (in accordance with conventional symptom-based method used by doctors) is used as a basis. Disclosure of Reference 20 is incorporated herein by reference in its entirety.

Reference 20: Ichikawa, N., Lisi, G., Yahata, N., Okada, G., Takamura, M., Yamada, M., et al. (2017). Identifying melancholic depression biomarker using whole-brain functional connectivity. arXiv.

In many studies, however, it has been pointed out that clear relation is difficult to find between existing clinical diagnosis categories and neurobiological abnormalities. This difficulty is believed to originate in the fact that each patient's diagnosis is based on information of a complex mixture of symptoms, epidemiological study and the doctor's experience. Pathologic states caused by the concomitant medical problems including structural, functional and genetic abnormalities related to a plurality of diseases makes this problem more difficult.

Against this background, for the diagnosis and treatment of MDD based on neuro-scientific understanding, it is necessary to compare functional connectivity related to the MDD diagnosis with the resting state functional connectivity related to depressive symptoms and to examine the functional connectivity related to such symptoms.

Therefore, in the following, we describe a machine learning algorithm that automatically and objectively identifies a resting state functional connectivity FC related to diagnosis and symptoms.

Figure 37:
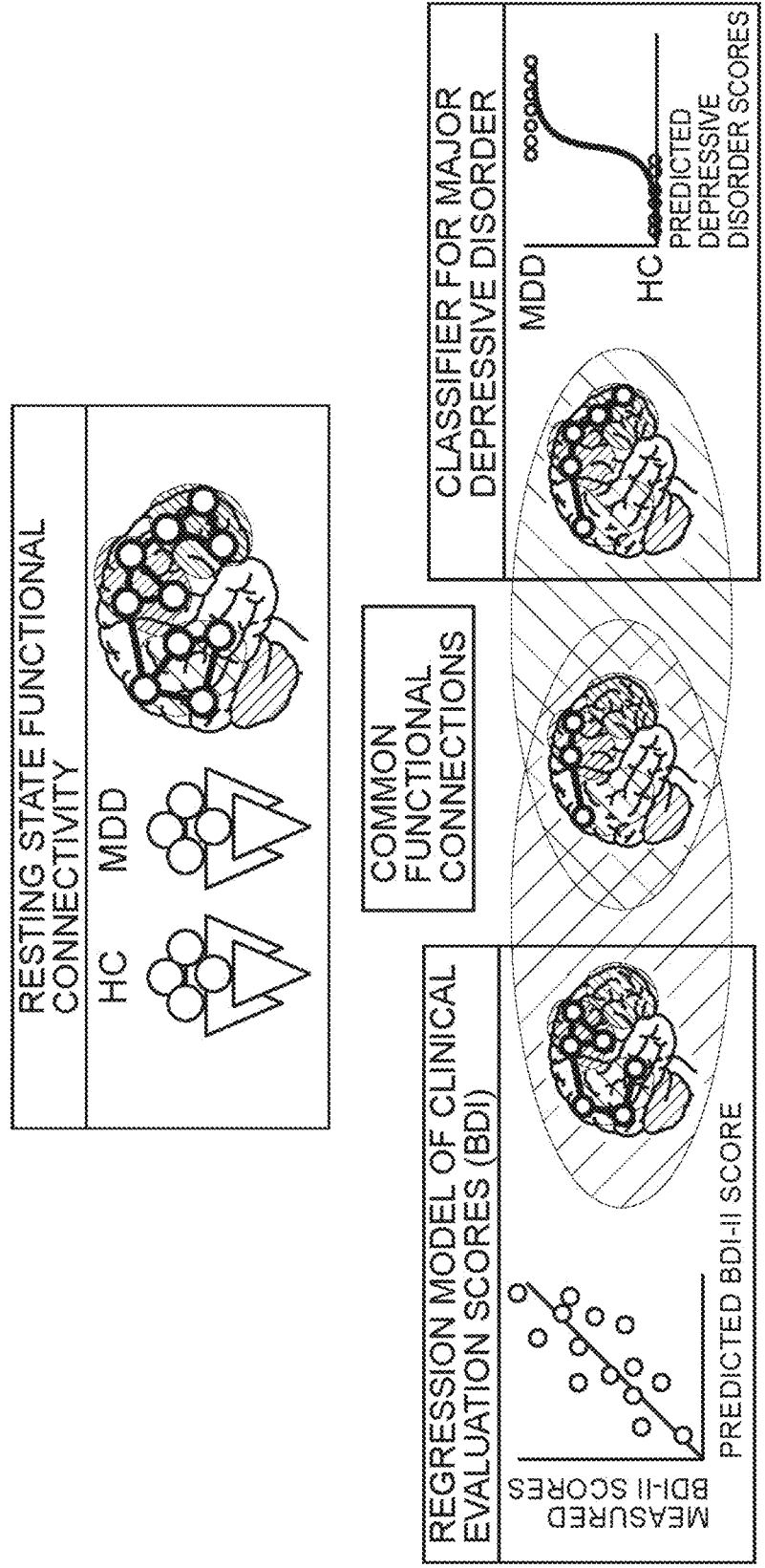
FIG. 37 illustrates a procedure for deriving brain functional connectivity common to diagnosis and symptoms of mental disease (for example, major depressive disorder).

FIG. 37 illustrates a procedure for deriving the brain functional connectivity common to diagnosis and symptoms of mental disease (for example, major depressive disorder). Specifically, as described heretofore, we generate a classifier that discriminates a group of healthy controls (HCs) and a group of patients (for example, MDD patient cohort) based on the resting state brain functional connectivity. On the other hand, as will be described later, we build a regression model of an evaluation measure of symptoms (for example, Beck Depression Inventory II) based on the resting state functional connectivity. Thereafter, we extract any common part between the brain functional connectivity related to diagnosis and the brain functional connectivity related to symptoms.

Figure 38:
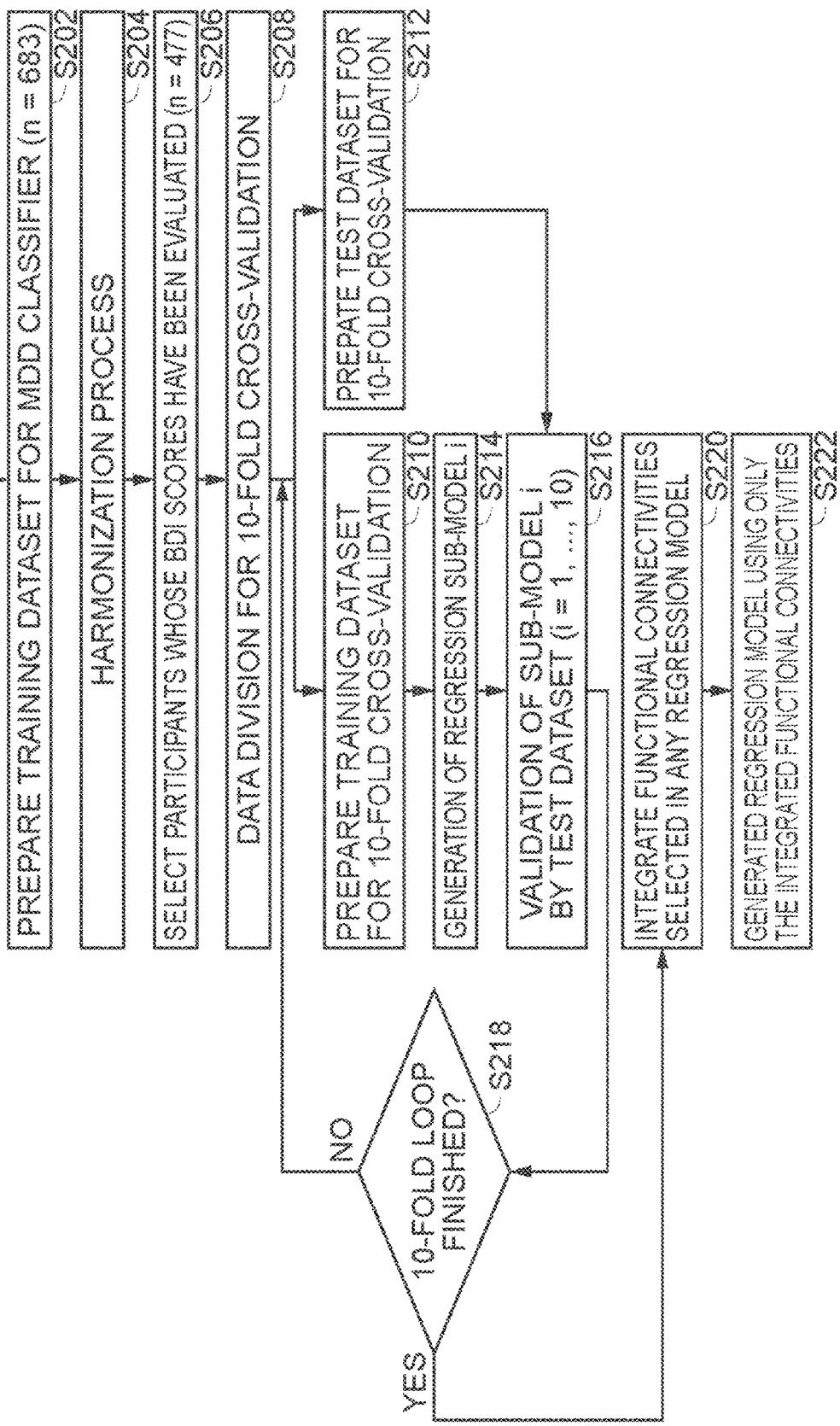
FIG. 38 is a flowchart showing a procedure for generating a regression model that may predicts symptom evaluation measure (for example, Beck Depression Inventory II).

FIG. 38 is a flowchart showing a procedure for generating a regression model that predicts the symptom evaluation measure (for example, Beck Depression Inventory II).

Referring to FIG. 38, when a learning process of evaluation measure regression model starts (S200), using a pre-prepared (and stored in storage device 2080') training dataset (S202), correlation matrix calculating unit 3002 calculates elements of the connectivity matrix.

Thereafter, harmonization calculating unit 3020 calculates the measurement bias and executes the harmonization process (S204). As described above, the method utilizing the traveling subjects is preferred for the harmonization process. Any other method, however, may be used.

Then, discriminator generator 3008 obtains, as the training dataset, data of participants that have already obtained the symptom evaluation measure (for example, BDI score), from the dataset after harmonization (S206).

Thereafter, discriminator generator 3008 performs a so-called "K-fold cross validation" on the training data and thereby generates a regression model of the evaluation measure.

First, in order to execute the learning process using the "K-fold cross validation" on the training data, discriminator generator 3008 sets K to 10, for example, and divides the training data into ten sub-datasets. Specifically, discriminator generator 3008 uses one sub-dataset of the K-divided data (one of 10-divided data), as a "test dataset" for validation and assigns the remaining (K−1) (9 of 10-divided) data as the training dataset (S210, S212).

Then, discriminator generator 3008 builds a linear regression model for predicting the BDI score using the training dataset based on the values of 71,631 functional connections FC, as represented by the equation below. Specifically, in order to build a linear regression model, using LASSO, discriminator generator 3008 generates regression sub-models i (i=1 to K) by linear regression, as given below (S214).

(predicted $BDI_{sub}$)=$w^T c_{sub}$

Here, the predicted $BDI_{sub}$ represents a BDI score of a participant, and $c_{sub}$ represents the functional connectivity FC vector of the participant. Further, w represents a weight vector of linear regression. The regression model is not limited to a linear regression model, and other functional regression models may be used.

Thereafter, the regression sub-model i is validated using the test dataset (S216).

Then, if it is determined that the K-th (10) loop of cross-validation has not yet been finished (N at S218), discriminator generator 3008 sets that sub-dataset of the K-divided data which is different from those used in the past as the test dataset, and assigns the remaining sub-datasets as the training dataset (S210, S212), and repeats the process.

On the other hand, if the K-th (10th) loop of cross-validation is finished (Y at S218), discriminator generator 3008 extracts, from the 10-divided training dataset, a subset of brain functional connectivity integrating functional connectivity FC selected for generating a sub-model (S220), and builds a regression model using such a subset of brain functional connectivity as explanatory variables (S222).

This procedure, however, may possibly cause information leak among divisions and the result of learning of the training dataset may lead to over-fitting. Therefore, as described in the following, by applying the regression model to an independent validation dataset, the generalization capability is also confirmed.

Figure 39:
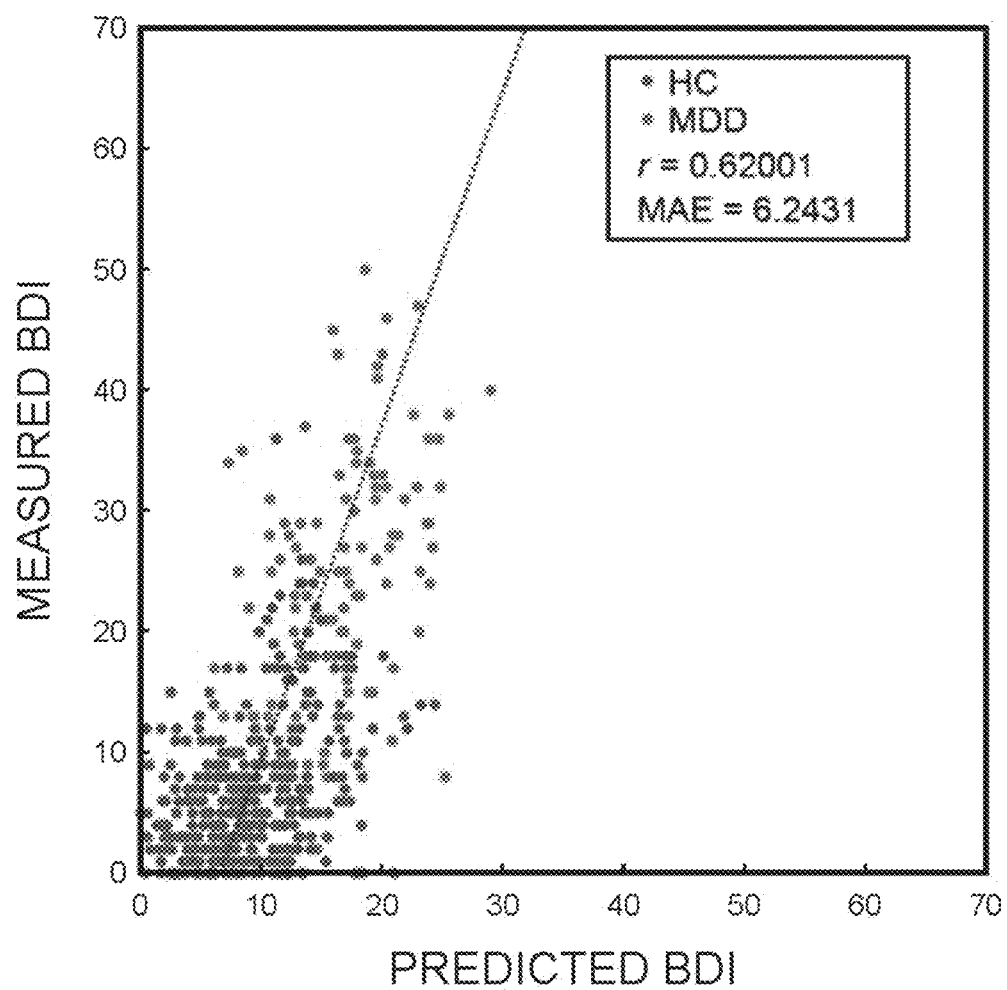
FIG. 39 shows the prediction performance of a regression model generated based on the training dataset.

FIG. 39 shows the prediction performance of a regression model generated based on the training dataset. As shown in FIG. 39, Pearson's correlation coefficient r and mean absolute error (MAE) between the BDI score predicted by the regression model and the actually measured BDI score are also shown.

Referring to FIG. 39, it can be seen that by this regression model, the BDI scores can be well predicted with statistically significant correlation (r=0.62 and p=5.3×10$^{-52}$; mean absolute error=6.24).

Figure 40:
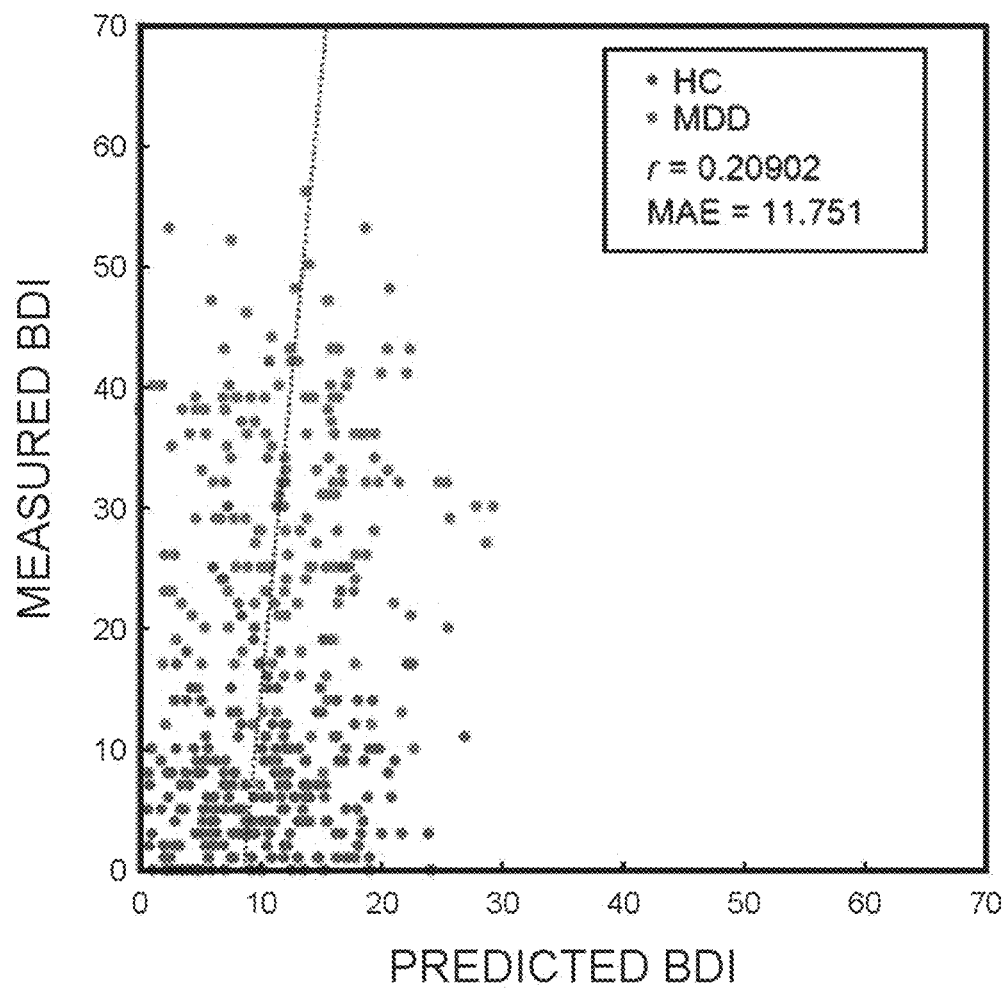
FIG. 40 shows the performance of a regression model for the BDI scores for the independent validation dataset.

FIG. 40 shows the performance of a regression model for the BDI scores for the independent validation dataset. FIG. 40 is a scatter diagram showing the measured BDI and predicted BDI.

Here again, it can be seen that by this regression model, the BDI scores can be well predicted with statistically significant correlation (r=0.21 and p=9.1×10$^{-6}$; mean absolute error=11.8).

FIG. 41 shows spatial distribution of seven brain functional connections FC common in building the MDD classifier and the BDI regression model. In FIG. 41, the functional connectivity common to diagnosis and symptoms is shown as views from behind, left, right and above. The interhemicerebral connection is shown only in the views from behind and in the plan view.

FIG. 42 shows a list indicating the characteristics of the common seven brain function connections FC shown in FIG. 41. FIG. 42 shows the common functional connectivity and the weights in the regression model of the BDI scores.

For extracting the common functional connections FC shown in FIGS. 41 and 42, first, important functional connectivity related to diagnosis from the MDD classifier and important functional connectivity related to symptoms from the BDI regression models are extracted by discriminator generator 3008.

Specifically, discriminator generator 3008 counts the number of each functional connection FC selected by the LASSO calculation during the 10-fold cross-validation. If any count is determined to be significantly higher than chance by binomial test, the corresponding functional connectivity is determined to be important.

In the specific example described above, the number of functional connections FC used by an MDD classifier per one cross-validation was 329.1 in average (this number of FCs represents the number that it was selected to at least once in 10 sub-samplings). As regards FCs related to diagnosis, the binominal distribution of the number of counts is assumed with B (10, 329/71,631). Then, after the Bonferroni correction, significance level is determined as 0.05/71,631.

In the specific example above, discriminator generator 3008 determines that any FC that is selected three times or more in the 10-fold cross-validation is an important FC related to diagnosis.

Similarly, as regards FCs related to symptoms, the number of functional connections FC used in a BDI regression model was 3.4 in average per 1-division cross-validation, and the binominal distribution of the number of counts is assumed with B (10, 3/71,631). In the specific example above, discriminator generator 3008 determines that any FC that is selected once or more in the 10-fold cross-validation is an important FC related to symptoms.

By a machine learning algorithm, from the data of the BDI score regression model and the classifier between the MDD patients and the healthy controls HCs, 340 functional connections FC related to diagnosis and 21 functional connections FC related to symptoms are specified automatically and objectively.

Among the 340 functional connections FC and the 21 functional connections FC, seven functional connections FC were common.

Figure 43:
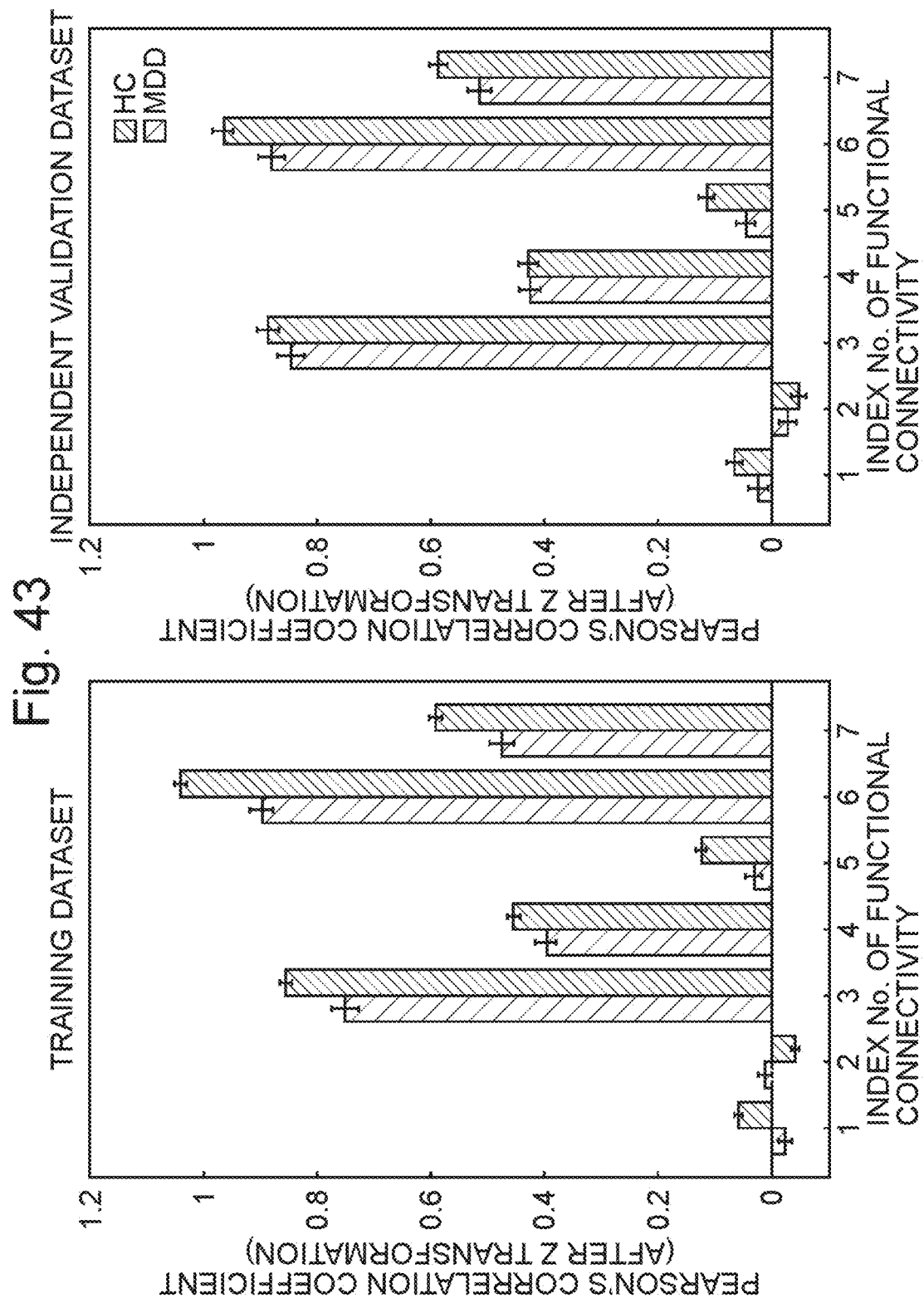
FIG. 43 shows values of functional connections FC between the training dataset and the independent validation dataset of common functional connectivity FC.

FIG. 43 shows the values of functional connections FC between the training dataset and the independent validation dataset of common functional connectivity. As shown in FIG. 43, the average values of functional connectivity of the seven common functional connections FC were very close between the training dataset and the independent validation dataset. This result suggests that the seven functional connections FC are reliable in characterizing neural basis of MDD and depressive disorder.

Therefore, by the method described above, it is possible to build a reliable BDI regression model and the MDD classifier based on brain imaging, by using whole brain pattern of functional connections FC, using the resting state fMRI data of the MDD patient cohorts and the healthy control cohorts HCs collected at a plurality of sites.

The MDD classifier attained highly generalized prediction performances ACU and MCC with respect to the independent validation data. Further, the highly generalized prediction performance can be attained not only on the entire dataset of independent validation data but also individually on the datasets of four imaging sites. These validation datasets are not included in the training dataset. Further, the imaging protocols of the independent validation dataset were, strictly speaking, different from those of the training dataset, whereas the generalization could be attained. This means that an MDD classifier generalized to the independent validation data could be successfully built based on the brain functional connectivity FC and, in addition, the generalized classification for MDD not having any MDD sub-type limitations was successfully attained.

Further, the machine learning algorithm as described above enables the reliable extraction of an important functional connectivity FC common to a disease classifier (for example, the MDD) and to a regression model of symptoms evaluation measure (for example, the BDI scores).

Further, regarding the MDD, as characteristics of seven functional connections FC common to the diagnosis and symptoms, the following points are noted.

First, regarding the strength of the functional connectivity FC, seven FCs all indicate hypoconnectivity in the group of MDD samples (specifically, the strength of the functional connectivity FC becomes closer to zero in the group of MDD samples than in the group of HC samples).

Second, regarding contribution to the internal functional networks, the seven functional connections are closely related to the default mode network and to the salience network.

Of thirteen brain regions including these seven functional connections, five portions belong to the default mode network and five portions belong to the salience network.

Further, six functional connections FC have a node (ROI) either in the default mode network or the salience network. Two of the seven functional connections were between the two networks. Two functional connections were in the default mode network, and one was in the salience network. The default mode network and the salience network have been conventionally reported to have a relation to a depressive state and the results above do not contradict such reports.

While biomarkers are developed for the purpose of patients' diagnosis, studies are increasingly focused on the identification of biomarkers that determine the goals of treatment (specifically, biomarkers that join diagnosis and treatment together), which enables a larger number of individualized treatment approaches. The common functional connections FC extracted through the above-described procedure relate not only to MDD diagnosis but also to depressive symptoms and, therefore, the seven functional connections FC are promising candidates of a biomarker that joins the diagnosis and the treatment of MDD. Therefore, in order to alleviate depressive symptoms, it becomes possible to use a method of intervening functional connectivity such as the functional connectivity neurofeedback training, on the functional connectivity using such a method as described, for example, in Reference 21 below. The disclosure of Reference 21 is incorporated herein by reference in its entirety.

Reference 21: Yamada, T., Hashimoto, R. I., Yahata, N., Ichikawa, N., Yoshihara, Y., Okamoto, Y., et al. (2017). Resting-State Functional Connectivity-Based Biomarkers and Functional MRI-Based Neurofeedback for Psychiatric Disorders: A Challenge for Developing Theranostic Biomarkers. Int J Neuropsychopharmacol 20(10), 769-781. doi: 10.1093/ijnp/pyx059.

The embodiments as have been described here are mere examples and should not be interpreted as restrictive. The scope of the present invention is determined by each of the claims with appropriate consideration of the written description of the embodiments and embraces modifications within the meaning of, and equivalent to, the languages in the claims.

REFERENCE SIGNS LIST

2 subject, 6 display, 10 MRI device, 11 magnetic field applying mechanism, 12 static magnetic field generating coil, 14 magnetic field gradient generating coil, 16 RF irradiating unit, 18 bed, 20 receiving coil, 21 driving unit, 22 static magnetic field power source, 24 magnetic field gradient power source, 26 signal transmitting unit, 28 signal receiving unit, 30 bed driving unit, 32 data processing unit, 36 storage unit, 38 display unit, 40 input unit, 42 control unit, 44 interface unit, 46 data collecting unit, 48 image processing unit, 50 network interface

The invention claimed is:

1. An adjustment system for correcting a brain functional connectivity correlation value of an object, comprising:
   a plurality of brain activity measurement devices provided respectively at a plurality of measurement sites, for time-sequentially measuring brain functions of a plurality of subjects; and
   a computing system for correcting said brain functional connectivity correlation value;
   said computing system includes
   a storage device for storing data, said storage device storing results of measurements of brain activities of a predetermined plurality of brain regions of each of a plurality of subjects including
   a plurality of traveling subjects who are common objects of measurements at each of said plurality of measurement sites, a plurality of healthy subjects who are objects of measurement at one or more of the plurality of measurement sites, and a plurality of patient subjects who are objects of measurement at one or more of the plurality of measurement sites; and a processor and a memory, wherein said memory stores instructions, which when executed by said processor, performs a process comprising:

calculating prescribed elements of said brain functional connectivity matrix for each of said plurality of subjects, using a regression model of a functional connectivity vector to define a generalized linear mixed model to include a linear predictor having a plurality of factors at each of the plurality of measurement sites as fixed-effect coefficients, the generalized linear mixed model being defined so that each of the plurality of factors has a fixed effect average of zero across the plurality of measurement sites, wherein the plurality of factors are calculated separately and include measurement bias, sampling bias of healthy subjects exclusive of patient subjects of one or more diseases, and sampling bias of patient subjects of one or more diseases exclusive of the healthy subjects, and wherein the generalized linear mixed model is further defined to include a link function connecting the linear predictor to each element of the brain functional connectivity matrix;

applying said generalized linear mixed model to calculate the fixed effect of measurement bias for each element of said brain functional connectivity matrix at each of said plurality of measurement sites with respect to an average of the corresponding element across said plurality of measurement sites and across said plurality of subjects, and using the fixed effect of measurement bias at each of said plurality of measurement sites, correcting said brain functional connectivity correlation value as the prescribed elements of said brain functional connectivity matrix of each of the plurality of subjects measured at the corresponding measurement site and thereby obtaining an adjusted value, wherein the generalized linear mixed model is applied using a regression model of a functional connectivity vector comprising a plurality of correlation values among brain areas defined as follows:

$$\text{Connectivity} = x_m^T m + x_{Shc}^T S_{hc} + x_{Sdis}^T S_{dis} + x_d^T d + x_p^T p + \text{const} + e, \text{ and}$$

$$\Sigma_i^{N_{ts}} p_i = 0, \Sigma_k^{N_s} m_k = 0, \Sigma_k^{Nsh} S_{hc\ k} = 0, \Sigma_k^{Nsd} S_{dis\ k} = 0, d_1(HC) = 0,$$

where $N_{ts}$ is the number of the plurality of traveling subjects, p is a participant factor of a particular traveling subject i, $N_s$ is the number of the plurality of measurement sites, m is the measurement bias and $m_k$ being the measurement bias at a particular measurement site k of the Ns measurement sites, $S_{hc}$ is the sampling bias of healthy subjects with $S_{hc\ k}$ being the sampling bias of healthy subjects at the particular site k, $S_{hc}$ is the sampling bias of healthy subjects with $S_{dis\ k}$ being the sampling bias of patient subjects at the particular site k, and dis a disease factor evaluated as a deviation from a healthy cohort HC, const is a constant, e represents noise, T represents a transpose of a vector, and $x^T$ represents a row vector, wherein, after a regression calculation is performed on the regression model, b-th connectivity of a subject is given as $$\text{Connectivity} = x_m^{aT} m^b + x_{Shc}^{aT} S_{hc}^b + x_{Sdis}^{aT} S_{dis}^b + x_d^{aT} d^b + x_p^{aT} p^b + \text{const} + e.$$

2. A system for harmonizing a brain activity classifier to execute a process of classification of at least one attribute based on a result of brain activity measurement of objects, comprising:

a plurality of brain activity measurement devices provided respectively at a plurality of measurement sites, for time-sequentially measuring brain functions of a plurality of subjects;

a computing system for correcting a brain functional connectivity correlation value as prescribed elements of a brain functional connectivity matrix representing temporal correlation of brain activities of the subjects as objects of training data; wherein said computing system includes a storage device for storing data, said storage device storing results of said measurements of said brain activities of a predetermined plurality of brain regions of each of a plurality of subjects including a plurality of traveling subjects who are common objects of measurements at each of said plurality of measurement sites, a plurality of healthy subjects who are objects of measurement at one or more of the plurality of measurement sites, and a plurality of patient subjects who are objects of measurement at one or more of the plurality of measurement sites; and said computing system further includes a processor and a memory; wherein said memory stores instructions which, when executed by said processor, performs a process comprising:

calculating prescribed elements of said brain functional connectivity matrix for each of said plurality of subjects, defining a generalized linear mixed model to include a linear predictor having a plurality of factors at each of the plurality of measurement sites as fixed-effect coefficients, the generalized linear mixed model being defined so that each of the plurality of factors has a fixed effect average of zero across the plurality of measurement sites, wherein the plurality of factors are calculated separately and include measurement bias, sampling bias of healthy subjects exclusive of patient subjects of one or more diseases, and sampling bias of patient subjects of one or more diseases exclusive of the healthy subjects, and wherein the generalized linear mixed model is further defined to include a link function connecting the linear predictor to each element of the brain functional connectivity matrix applying said generalized linear mixed model to calculate the fixed effect of measurement bias for each element of said brain functional connectivity matrix at each of said plurality of measurement sites with respect to an average of the corresponding element across said plurality of measurement sites and across said plurality of subjects, and using said fixed effect of measurement bias at each of the plurality of measurement sites, correcting said brain functional connectivity correlation value as the prescribed elements of said brain functional connectivity matrix of each of the plurality of subjects measured at the corresponding measurement site and thereby obtaining an adjusted value; and training said brain activity classifier for said attribute through machine learning with feature selection, based on said adjusted value, wherein the generalized linear mixed model is applied using a regression model of a functional connectivity vector comprising a plurality of correlation values among brain areas defined as follows:

Connectivity=$x_m^T m + x_{Shc}^T S_{hc} + x_{Sdis}^T S_{dis} + x_d^T d + x_p^T p +$ const+$e$, and $\Sigma_i^{Nts} p_i = 0, \Sigma_k^{Ns} m_k = 0, \Sigma_k^{Nsh} S_{hc\ k} = 0, \Sigma_k^{Nsd} S_{dis\ k} = 0, d_1(HC) = 0,$ where $N_{ts}$ is the number of the plurality of traveling subjects, p is a participant factor of a particular traveling subject i, $N_s$ is the number of the plurality of measurement sites, m is the measurement bias and $m_k$ being the measurement bias at a particular measurement site k of the Ns measurement sites, $S_{hc}$ is the sampling bias of healthy subjects with $S_{hc\ k}$ being the sampling bias of healthy subjects at the particular site k, $S_{hc}$ is the sampling bias of healthy subjects with $S_{dis\ k}$ being the sampling bias of patient subjects at the particular site k, and d is a disease factor evaluated as a deviation from a healthy cohort HC, const is a constant, e represents noise, T represents a transpose of a vector, and $x^T$ represents a row vector, wherein, after a regression calculation is performed on the regression model, b-th connectivity of a subject is given as Connectivity=$x_m^{aT} m^b + x_{Shc}^{aT} S_{hc}^b + x_{Sdis}^{aT} S_{dis}^b + x_d^{aT} d^b + x_p^{aT} p^b +$const+$e$.

3. The system for harmonizing a brain activity classifier according to claim 2, wherein said plurality of subjects as objects of training data subjected to measurements of brain activities at each of the plurality of measurement sites include a first group of subjects having said attribute and a second group of subjects not having said attribute; and in calculating said measurement bias, said processor calculates, using said generalized linear mixed model, the measurement bias, a sampling bias of said first group and a sampling bias of said second group, for each element of said brain functional connectivity matrix, as a fixed effect at each measurement site with respect to an average of the corresponding element across said plurality of measurement sites and across said plurality of traveling subjects.

4. The system for harmonizing a brain activity classifier according to claim 2, wherein in said generalized linear mixed model, the measurement bias is calculated by the least square regression by L2 normalization.

5. The system for harmonizing a brain activity classifier according to claim 2, wherein said machine learning with feature selection is a logistics regression analysis using LASSO.

6. A method comprising:

obtaining results of measurements of brain activities of a predetermined plurality of brain regions of each of a plurality of subjects including a plurality of traveling subjects for whom brain activities of a predetermined plurality of brain regions of each of said traveling subjects have been measured as common objects of measurements at each of a plurality of measurement sites, a plurality of healthy subjects who are objects of measurement at one or more of the plurality of measurement sites, and a plurality of patient subjects who are objects of measurement at one or more of the plurality of measurement sites;

for each of said plurality of subjects, calculating prescribed elements of a brain functional connectivity matrix representing temporal correlation of said brain activities of said predetermined plurality of brain regions;

defining a generalized linear mixed model to include a linear predictor having a plurality of factors at each of the plurality of measurement sites as fixed-effect coefficients, the generalized linear mixed model being defined so that each of the plurality of factors has a fixed effect average of zero across the plurality of measurement sites, wherein the plurality of factors are calculated separately and include measurement bias, sampling bias of healthy subjects exclusive of patient subjects of one or more diseases, and sampling bias of patient subjects of one or more diseases exclusive of the healthy subjects, and wherein the generalized linear mixed model is further defined to include a link function connecting the linear predictor to each element of the brain functional connectivity matrix;

applying the generalized linear mixed model to calculate the fixed effect of measurement bias for each element of said brain functional connectivity matrix at each of the plurality of measurement sites with respect to an average of the corresponding element across said plurality of measurement sites and across said plurality of subjects; and using said fixed effect of measurement bias at each of the plurality of measurement sites, correcting a brain functional connectivity correlation value as the prescribed elements of said brain functional connectivity matrix of each of the plurality of subjects measured at the corresponding measurement site and thereby obtaining an adjusted value, wherein the generalized linear mixed model is applied using a regression model of a functional connectivity vector comprising a plurality of correlation values among brain areas defined as follows:

Connectivity=$x_m^T m + x_{Shc}^T S_{hc} + x_{Sdis}^T S_{dis} + x_d^T d + x_p^T p +$ const+$e$, and $\Sigma_i^{Nts} p_i = 0, \Sigma_k^{Ns} m_k = 0, \Sigma_k^{Nsh} S_{hc\ k} = 0, \Sigma_k^{Nsd} S_{dis\ k} = 0, d_1(HC) = 0,$ where $N_{ts}$ is the number of the plurality of traveling subjects, p is a participant factor of a particular traveling subject i, $N_s$ is the number of the plurality of measurement sites, m is the measurement bias and $m_k$ being the measurement bias at a particular measurement site k of the Ns measurement sites, $S_{hc}$ is the sampling bias of healthy subjects with $S_{hc\ k}$ being the sampling bias of healthy subjects at the particular site k, $S_{hc}$ is the sampling bias of healthy subjects with $S_{dis\ k}$ being the sampling bias of patient subjects at the particular site k, and dis a disease factor evaluated as a deviation from a healthy cohort HC, const is a constant, e represents noise, T represents a transpose of a vector, and $x^T$ represents a row vector, wherein, after a regression calculation is performed on the regression model, b-th connectivity of a subject is given as $$\text{Connectivity} = x_m^{aT} m^b + x_{Shc}^{aT} S_{hc}^b + x_{Sdis}^{aT} S_{dis}^b + x_d^{aT} d^b + x_p^{aT} p^b + \text{const} + e.$$

7. The method according to claim 6, wherein said method harmonizes a brain activity classifier for executing a process of classification of an attribute of subjects measured at one or more of said plurality of measurement sites, and further comprises the step of:

generating a classifier for said attribute through machine learning with feature selection, based on said adjusted value.

8. The method according to claim 7, wherein said method adjusts a brain functional connectivity correlation value of one of said plurality of traveling subjects measured at said plurality of measurement sites, and further comprises the step of:

measuring said brain activities of said predetermined plurality of brain regions of each of said traveling subjects.

9. The method of harmonizing a brain activity classifier according to claim 7, wherein said plurality of subjects as objects of training data subjected to measurements of brain activities at each of the plurality of measurement sites include a first group of subjects having said attribute and a second group of subjects not having said attribute;

said step of calculating measurement bias includes the step of using said generalized linear mixed model, calculating the measurement bias, sampling bias of said first group and sampling bias of said second group, for each element of said brain functional connectivity matrix, as fixed effects at each measurement site with respect to an average of the corresponding element across said plurality of measurement sites and across said plurality of traveling subjects.

10. The method of harmonizing a brain activity classifier according to claim 7, wherein in said generalized linear mixed model, the measurement bias is calculated by the least square regression by L2 normalization.

11. The method of harmonizing a brain activity classifier according to claim 7, wherein said machine learning with feature selection is a logistics regression analysis using LASSO (least absolute shrinkage and selection operator).

* * * * *